(12) United States Patent
Hughey et al.

(10) Patent No.: US 10,335,375 B2
(45) Date of Patent: Jul. 2, 2019

(54) ANTI-OVERINGESTION ABUSE DETERRENT COMPOSITIONS

(71) Applicant: PATHEON SOFTGELS INC, High Point, NC (US)

(72) Inventors: Justin Hughey, Asheboro, NC (US); Jason Vaughn, Browns Summit, NC (US)

(73) Assignee: Patheon Softgels, Inc., High Point, NC (US)

( * ) Notice: Subject to any disclaimer, the term of this patent is extended or adjusted under 35 U.S.C. 154(b) by 40 days.

(21) Appl. No.: 15/990,885

(22) Filed: May 29, 2018

(65) Prior Publication Data

US 2018/0344651 A1    Dec. 6, 2018

Related U.S. Application Data

(60) Provisional application No. 62/512,446, filed on May 30, 2017.

(51) Int. Cl.
*A61K 9/48* (2006.01)
*A61K 31/485* (2006.01)

(52) U.S. Cl.
CPC .......... *A61K 9/4866* (2013.01); *A61K 9/4858* (2013.01); *A61K 31/485* (2013.01); *A61K 9/4891* (2013.01)

(58) Field of Classification Search
CPC .................................................. A61K 9/4866
USPC ........................................................ 514/252
See application file for complete search history.

(56) References Cited

U.S. PATENT DOCUMENTS

| | | | |
|---|---|---|---|
| 4,459,278 A | 7/1984 | Porter | |
| 4,529,583 A | 7/1985 | Porter | |
| 4,828,836 A | 5/1989 | Elger | |
| 4,861,598 A | 8/1989 | Oshlack | |
| 4,970,075 A | 11/1990 | Oshlack | |
| 5,266,331 A | 11/1993 | Oshlack | |
| 5,273,760 A | 12/1993 | Oshlack | |
| 5,286,493 A | 2/1994 | Oshlack | |
| 5,472,943 A | 12/1995 | Crain | |
| 5,478,577 A | 12/1995 | Sackler | |
| 5,529,787 A | 6/1996 | Merrill | |
| 5,549,912 A | 8/1996 | Oshlack | |
| 5,656,295 A | 8/1997 | Oshlack | |
| 5,672,360 A | 9/1997 | Sackler | |
| 5,702,725 A | 12/1997 | Merrill | |
| 5,914,131 A | 6/1999 | Merrill | |
| 5,958,452 A | 9/1999 | Oshlack | |
| 5,965,161 A | 10/1999 | Oshlack | |
| 6,228,863 B1 | 5/2001 | Palermo | |
| 6,261,599 B1 | 7/2001 | Oshlack | |
| 6,277,384 B1 | 8/2001 | Kaiko | |
| 6,335,033 B2 | 1/2002 | Oshlack | |
| 6,375,957 B1 | 4/2002 | Kaiko | |
| 6,383,736 B1 | 5/2002 | Titmas | |
| 6,475,494 B2 | 11/2002 | Kaiko | |
| 6,488,963 B1 | 12/2002 | McGinity | |
| 6,514,531 B1 | 2/2003 | Alaux | |
| 6,627,635 B2 | 9/2003 | Palermo | |
| 6,685,964 B1 | 2/2004 | Bartholomaeus | |
| 6,696,066 B2 | 2/2004 | Kaiko | |
| 6,696,088 B2 | 2/2004 | Oshlack | |
| 6,706,281 B2 | 3/2004 | Oshlack | |
| 6,713,488 B2 | 3/2004 | Sadee et al. | |
| 6,733,783 B2 | 5/2004 | Oshlack | |
| 6,734,188 B1 | 5/2004 | Rhodes | |
| 6,743,442 B2 | 6/2004 | Oshlack | |
| 6,893,661 B1 | 5/2005 | Odidi | |
| 7,129,248 B2 | 10/2006 | Chapman | |
| 7,141,250 B2 | 11/2006 | Oshlack | |
| 7,144,587 B2 | 12/2006 | Oshlack | |
| 7,157,100 B2 | 1/2007 | Doshi | |
| 7,157,103 B2 | 1/2007 | Sackler | |
| 7,160,559 B1 | 1/2007 | McGee | |
| 7,172,767 B2 | 2/2007 | Kaiko | |
| 7,201,920 B2 | 4/2007 | Kumar | |
| 7,276,250 B2 | 10/2007 | Baichwal | |
| 7,332,182 B2 | 2/2008 | Sackler | |
| 7,384,653 B2 | 6/2008 | Wright, IV | |
| 7,399,488 B2 | 7/2008 | Hirsh | |
| 7,419,686 B2 | 9/2008 | Kaiko | |
| 7,476,402 B2 | 1/2009 | Kumar | |
| 7,510,726 B2 | 3/2009 | Kumar | |
| 7,510,727 B2 | 3/2009 | Oshlack | |
| 7,514,100 B2 | 4/2009 | Oshlack | |
| 7,632,921 B2 | 12/2009 | Pan | |
| 7,674,798 B2 | 3/2010 | Chapman | |
| 7,674,799 B2 | 3/2010 | Chapman | |
| 7,674,800 B2 | 3/2010 | Chapman | |
| 7,682,633 B2 | 3/2010 | Matthews | |
| 7,682,634 B2 | 3/2010 | Matthews | |
| 7,683,072 B2 | 3/2010 | Chapman | |
| 7,691,877 B2 | 4/2010 | Jones | |
| 7,696,208 B2 | 4/2010 | Kyle | |

(Continued)

OTHER PUBLICATIONS

US 8,975,271 B2, 03/2015, Oshlack (withdrawn)
US 9,005,659 B2, 04/2015, Wright (withdrawn)
US 9,023,796 B2, 05/2015, Lu (withdrawn)
Shah et al. "Complexation between risperidone and amberlite resin by various methods of preparation and binding study," Drug Development and Industrial Pharmacy 35(12): 1409-1418 (2009).
SenGupta, Ion Exchange and Solvent Extraction: A series of Advances, CRC Press 18:127-130 (2007).

(Continued)

*Primary Examiner* — Raymond J Henley, III
(74) *Attorney, Agent, or Firm* — Brinks Gilson & Lione

(57) ABSTRACT

Described herein are abuse deterrent oral pharmaceutical compositions, methods for making the same, and methods of treatment using such compositions. In particular, oral pharmaceutical compositions that mitigate the risk of overingestion of one or more active pharmaceutical ingredients are described.

20 Claims, 3 Drawing Sheets

(56) References Cited

U.S. PATENT DOCUMENTS

| | | |
|---|---|---|
| 7,727,557 B2 | 6/2010 | Sackler |
| 7,740,881 B1 | 6/2010 | Sackler |
| 7,749,542 B2 | 7/2010 | Kaiko |
| 7,749,954 B2 | 7/2010 | Azria |
| 7,771,707 B2 | 8/2010 | Hirsh |
| 7,776,314 B2 | 8/2010 | Bartholomäus |
| 7,776,861 B2 | 8/2010 | Sun |
| 7,790,201 B2 | 9/2010 | Raman |
| 7,790,215 B2 | 9/2010 | Sackler |
| 7,815,934 B2 | 10/2010 | Boehm |
| 7,842,307 B2 | 11/2010 | Oshlack |
| 7,842,311 B2 | 11/2010 | Oshlack |
| 7,846,476 B2 | 12/2010 | Oshlack |
| 7,858,119 B1 | 12/2010 | Odidi |
| 7,858,609 B2 | 12/2010 | Shaw |
| 7,862,833 B2 | 1/2011 | Moe |
| 7,906,141 B2 | 3/2011 | Ziegler |
| 7,914,818 B2 | 3/2011 | Breder |
| 7,943,173 B2 | 5/2011 | Breder |
| 7,943,174 B2 | 5/2011 | Oshlack |
| 7,955,619 B2 | 6/2011 | Shah |
| 7,981,439 B2 | 7/2011 | Kumar |
| 8,017,148 B2 | 9/2011 | Sackler |
| 8,022,054 B2 | 9/2011 | Shaw |
| 8,030,310 B2 | 10/2011 | Kyle |
| 8,062,667 B2 | 11/2011 | Mehta |
| 8,075,872 B2 | 12/2011 | Arkenau-Maric |
| 8,101,630 B2 | 1/2012 | Kumar |
| 8,105,631 B2 | 1/2012 | Kaiko |
| 8,114,383 B2 | 2/2012 | Bartholomäus |
| 8,114,384 B2 | 2/2012 | Arkenau |
| 8,124,126 B2 | 2/2012 | Bosse |
| 8,142,811 B2 | 3/2012 | Oshlack |
| 8,153,590 B2 | 4/2012 | Lu |
| 8,158,156 B2 | 4/2012 | Matthews |
| 8,178,560 B2 | 5/2012 | Sun |
| 8,182,836 B2 | 5/2012 | Mehta |
| 8,192,722 B2 | 6/2012 | Arkenau-Maric |
| 8,202,537 B2 | 6/2012 | Mehta |
| 8,202,542 B1 | 6/2012 | Mehta |
| 8,231,898 B2 | 7/2012 | Oshlack |
| 8,231,901 B2 | 7/2012 | Breder |
| 8,236,328 B2 | 8/2012 | Babcock |
| 8,236,351 B2 | 8/2012 | Oshlack |
| 8,236,353 B2 | 8/2012 | Checot |
| 8,267,452 B2 | 9/2012 | Weber |
| 8,268,783 B2 | 9/2012 | Sinha |
| 8,298,577 B2 | 10/2012 | Moe |
| 8,298,579 B2 | 10/2012 | Abreu |
| 8,309,060 B2 | 11/2012 | Bartholomaus |
| 8,309,122 B2 | 11/2012 | Kao |
| 8,318,714 B2 | 11/2012 | Shaw |
| 8,323,889 B2 | 12/2012 | Arkenau-Maric |
| 8,329,216 B2 | 12/2012 | Kao |
| 8,337,888 B2 | 12/2012 | Wright |
| 8,337,890 B2 | 12/2012 | Mehta |
| 8,357,399 B2 | 1/2013 | Oshlack |
| 8,361,499 B2 | 1/2013 | Oshlack |
| 8,367,651 B2 | 2/2013 | Shaw |
| 8,377,480 B2 | 2/2013 | Raman |
| 8,383,152 B2 | 2/2013 | Jans |
| 8,389,007 B2 | 3/2013 | Wright |
| 8,409,616 B2 | 4/2013 | Kumar |
| 8,420,056 B2 | 4/2013 | Arkenau-Maric |
| 8,425,933 B2 | 4/2013 | Mehta |
| 8,445,018 B2 | 5/2013 | Habib |
| 8,445,023 B2 | 5/2013 | Guimberteau |
| 8,449,909 B2 | 5/2013 | Hirsh |
| 8,455,439 B2 | 6/2013 | Lu |
| 8,455,441 B2 | 6/2013 | Lu |
| 8,465,774 B2 | 6/2013 | Breder |
| 8,486,448 B2 | 7/2013 | Rahmouni |
| 8,486,449 B2 | 7/2013 | Rahmouni |
| 8,491,935 B2 | 7/2013 | Mehta |
| 8,518,443 B2 | 8/2013 | Breder |
| 8,524,275 B2 | 9/2013 | Oshlack |
| 8,529,948 B1 | 9/2013 | Wright |
| 8,551,520 B2 | 10/2013 | Oshlack |
| 8,557,291 B2 | 10/2013 | Rariy |
| 8,586,088 B2 | 11/2013 | Oshlack |
| 8,597,681 B2 | 12/2013 | Park |
| 8,597,684 B2 | 12/2013 | Mehta |
| 8,603,526 B2 | 12/2013 | Tygesen |
| 8,609,683 B2 | 12/2013 | Wright |
| 8,618,087 B2 | 12/2013 | Shaw |
| 8,623,418 B2 | 1/2014 | Liang |
| 8,637,540 B2 | 1/2014 | Kumar |
| 8,637,548 B2 | 1/2014 | Sun |
| 8,647,667 B2 | 2/2014 | Oshlack |
| 8,652,497 B2 | 2/2014 | Sackler |
| 8,652,515 B2 | 2/2014 | Sackler |
| 8,652,529 B2 | 2/2014 | Guimberteau |
| 8,658,631 B1 | 2/2014 | Devarakonda |
| 8,673,355 B2 | 3/2014 | Kaiko |
| 8,685,443 B2 | 4/2014 | Boehm |
| 8,685,444 B2 | 4/2014 | Boehm |
| 8,685,447 B2 | 4/2014 | Rahmouni |
| 8,691,270 B2 | 4/2014 | Rahmouni |
| 8,703,186 B2 | 4/2014 | Mehta |
| 8,703,196 B2 | 4/2014 | Babcock |
| 8,715,721 B2 | 5/2014 | Oshlack |
| 8,741,885 B1 | 6/2014 | Devarakonda |
| 8,747,902 B2 | 6/2014 | Mehta |
| 8,758,813 B2 | 6/2014 | Hirsh |
| 8,758,825 B2 | 6/2014 | Breder |
| 8,765,675 B2 | 7/2014 | Azria |
| 8,771,730 B2 | 7/2014 | Navon |
| 8,790,694 B2 | 7/2014 | Devarakonda |
| 8,790,700 B2 | 7/2014 | Mehta |
| 8,808,737 B2 | 8/2014 | Ahdieh |
| 8,808,740 B2 | 8/2014 | Huang |
| 8,808,741 B2 | 8/2014 | McKenna |
| 8,815,287 B2 | 8/2014 | Breder |
| 8,815,289 B2 | 8/2014 | McKenna |
| 8,821,929 B2 | 9/2014 | McKenna |
| 8,822,487 B2 | 9/2014 | Kaiko |
| 8,822,489 B2 | 9/2014 | Kumar |
| 8,822,687 B2 | 9/2014 | Chapman |
| 8,834,925 B2 | 9/2014 | McKenna |
| 8,840,928 B2 | 9/2014 | Rariy |
| 8,846,086 B2 | 9/2014 | McKenna |
| 8,846,090 B2 | 9/2014 | Brägmann |
| 8,846,091 B2 | 9/2014 | Brägmann |
| 8,846,104 B2 | 9/2014 | Matthews |
| 8,858,963 B1 | 10/2014 | Devarakonda |
| 8,871,265 B2 | 10/2014 | Wright |
| 8,877,247 B2 | 11/2014 | Matthews |
| 8,883,204 B2 | 11/2014 | Flath |
| 8,883,217 B2 | 11/2014 | Mehta |
| 8,889,129 B2 | 11/2014 | Lu |
| 8,894,987 B2 | 11/2014 | McKenna |
| 8,894,988 B2 | 11/2014 | McKenna |
| 8,901,113 B2 | 12/2014 | Leech |
| 8,911,719 B2 | 12/2014 | McKenna |
| 8,916,588 B2 | 12/2014 | Lickrish |
| 8,920,833 B2 | 12/2014 | Rahmouni |
| 8,920,834 B2 | 12/2014 | Rahmouni |
| 8,920,836 B2 | 12/2014 | Hayes |
| 8,927,010 B2 | 1/2015 | Lickrish |
| 8,927,013 B2 | 1/2015 | Rahmouni |
| 8,927,014 B2 | 1/2015 | Rahmouni |
| 8,932,630 B1 | 1/2015 | Kaiko |
| 8,936,808 B1 | 1/2015 | Kaiko |
| 8,936,812 B2 | 1/2015 | Oshlack |
| 8,951,555 B1 | 2/2015 | Oshlack |
| 8,969,369 B2 | 3/2015 | Caruso |
| 8,975,273 B2 | 3/2015 | Oshlack |
| 8,980,291 B2 | 3/2015 | Oshlack |
| 8,980,319 B2 | 3/2015 | Park |
| 8,992,975 B2 | 3/2015 | Devarakonda |
| 8,999,961 B2 | 4/2015 | Wright |
| 9,005,660 B2 | 4/2015 | Tygesen |
| 9,023,389 B1 | 5/2015 | Lickrish |
| 9,023,401 B1 | 5/2015 | Oshlack |

(56) References Cited

U.S. PATENT DOCUMENTS

| | | |
|---|---|---|
| 9,028,868 B2 | 5/2015 | Lickrish |
| 9,029,355 B2 | 5/2015 | Shaw |
| 9,034,376 B2 | 5/2015 | Wright |
| 9,034,377 B2 | 5/2015 | Wright |
| 9,034,902 B2 | 5/2015 | Lickrish |
| 9,040,084 B2 | 5/2015 | Wright |
| 9,044,398 B2 | 6/2015 | Hirsh |
| 9,044,402 B2 | 6/2015 | Tygesen |
| 9,044,435 B2 | 6/2015 | Wright |
| 9,050,335 B1 | 6/2015 | Devarakonda |
| 9,056,051 B2 | 6/2015 | Caruso |
| 9,056,052 B1 | 6/2015 | Oshlack |
| 9,056,054 B2 | 6/2015 | Dick |
| 9,056,107 B1 | 6/2015 | Oshlack |
| 9,056,116 B2 | 6/2015 | Shaw |
| 9,060,940 B2 | 6/2015 | Oshlack |
| 9,060,976 B2 | 6/2015 | Wright |
| 9,062,298 B2 | 6/2015 | Lu |
| 9,072,663 B2 | 7/2015 | Navon |
| 9,073,933 B2 | 7/2015 | Chapman |
| 9,084,729 B2 | 7/2015 | Caruso |
| 9,084,816 B2 | 7/2015 | McKenna |
| 9,095,614 B2 | 8/2015 | McKenna |
| 9,095,615 B2 | 8/2015 | McKenna |
| 9,096,656 B2 | 8/2015 | Pan |
| 9,101,636 B2 | 8/2015 | Brzeczko |
| 9,101,661 B2 | 8/2015 | McKenna |
| 9,101,668 B2 | 8/2015 | Oshlack |
| 9,109,046 B2 | 8/2015 | Sinha |
| 9,119,809 B2 | 9/2015 | Lickrish |
| 9,149,436 B2 | 10/2015 | Oshlack |
| 9,149,533 B2 | 10/2015 | Guido |
| 9,155,717 B2 | 10/2015 | Sackler |
| 9,161,937 B2 | 10/2015 | Caruso |
| 9,168,228 B2 | 10/2015 | Tygesen |
| 9,168,252 B2 | 10/2015 | Caruso |
| RE45,822 E | 12/2015 | Wright, IV |
| 9,198,861 B2 | 12/2015 | Park |
| 9,198,863 B2 | 12/2015 | Oshlack |
| 9,198,864 B2 | 12/2015 | Mehta |
| 9,198,867 B2 | 12/2015 | Bosse |
| 9,205,055 B2 | 12/2015 | Oshlack |
| 9,205,056 B2 | 12/2015 | Oshlack |
| 9,205,082 B2 | 12/2015 | Kaiko |
| 9,211,292 B2 | 12/2015 | Howard |
| 9,216,176 B2 | 12/2015 | Habib |
| 9,226,901 B2 | 1/2016 | Bosse |
| 9,259,387 B2 | 2/2016 | Navon |
| 9,283,214 B2 | 3/2016 | Lickrish |
| 9,289,394 B2 | 3/2016 | Lickrish |
| 9,301,918 B2 | 4/2016 | Raman |
| 9,308,170 B2 | 4/2016 | Wright |
| 9,308,171 B2 | 4/2016 | Wright |
| 9,320,796 B2 | 4/2016 | Brzeczko |
| 9,326,954 B2 | 5/2016 | Sackler |
| 9,358,295 B2 | 6/2016 | Tygesen |
| 9,364,520 B2 | 6/2016 | Pan |
| 9,387,173 B2 | 7/2016 | Wright |
| 9,387,174 B2 | 7/2016 | Wright |
| 9,387,177 B2 | 7/2016 | Bosse |
| 9,388,401 B2 | 7/2016 | Lu |
| 9,433,582 B2 | 9/2016 | Devarakonda |
| 9,849,125 B1 | 12/2017 | Yang |
| 9,861,629 B1 | 1/2018 | Hughey |
| 9,943,513 B1 | 4/2018 | Hughey |
| 2001/0033865 A1 | 10/2001 | Oshlack |
| 2001/0036476 A1 | 11/2001 | Oshlack |
| 2001/0038856 A1 | 11/2001 | Merrill |
| 2002/0004509 A1 | 1/2002 | Palermo |
| 2002/0006438 A1 | 1/2002 | Oshlack |
| 2002/0013301 A1 | 1/2002 | Kaiko |
| 2002/0058050 A1 | 5/2002 | Sackler |
| 2002/0058673 A1 | 5/2002 | Kaiko |
| 2002/0192277 A1 | 12/2002 | Oshlack |
| 2003/0026839 A1 | 2/2003 | Oshlack |
| 2003/0031712 A1 | 2/2003 | Kaiko |
| 2003/0035837 A1 | 2/2003 | Sackler |
| 2003/0044458 A1 | 3/2003 | Wright |
| 2003/0044464 A1 | 3/2003 | Ziegler |
| 2003/0064099 A1 | 4/2003 | Oshlack |
| 2003/0065002 A1 | 4/2003 | Caruso |
| 2003/0068370 A1 | 4/2003 | Sackler |
| 2003/0068371 A1 | 4/2003 | Oshlack |
| 2003/0068375 A1 | 4/2003 | Wright |
| 2003/0068392 A1 | 4/2003 | Sackler |
| 2003/0069263 A1 | 4/2003 | Breder |
| 2003/0073714 A1 | 4/2003 | Breder |
| 2003/0104063 A1 | 6/2003 | Babcock |
| 2003/0124185 A1 | 7/2003 | Oshlack |
| 2003/0157167 A1 | 8/2003 | Kao |
| 2003/0157168 A1 | 8/2003 | Breder |
| 2003/0190358 A1 | 10/2003 | Oshlack |
| 2003/0190362 A1 | 10/2003 | Sackler |
| 2003/0232081 A1 | 12/2003 | Doshi |
| 2004/0047907 A1 | 3/2004 | Oshlack |
| 2004/0052731 A1 | 3/2004 | Hirsh |
| 2004/0058946 A1 | 3/2004 | Buchwald |
| 2004/0081694 A1 | 4/2004 | Oshlack |
| 2004/0086561 A1 | 5/2004 | Kaiko |
| 2004/0170680 A1 | 9/2004 | Oshlack |
| 2004/0185096 A1 | 9/2004 | Oshlack |
| 2004/0202717 A1 | 10/2004 | Mehta |
| 2004/0234600 A1 | 11/2004 | Merrill |
| 2004/0266807 A1 | 12/2004 | Oshlack |
| 2005/0031546 A1 | 2/2005 | Bartholomaus |
| 2005/0063909 A1 | 3/2005 | Wright |
| 2005/0089568 A1 | 4/2005 | Oshlack |
| 2005/0112067 A1 | 5/2005 | Kumar |
| 2005/0163856 A1 | 7/2005 | Maloney |
| 2005/0192309 A1 | 9/2005 | Palermo |
| 2005/0214368 A1 | 9/2005 | Kawakami |
| 2005/0222188 A1 | 10/2005 | Chapman |
| 2005/0236741 A1 | 10/2005 | Arkenau |
| 2005/0245483 A1 | 11/2005 | Brogmann |
| 2005/0245556 A1 | 11/2005 | Brogmann |
| 2005/0265955 A1 | 12/2005 | Raman |
| 2005/0281748 A1 | 12/2005 | Hirsh |
| 2006/0002859 A1 | 1/2006 | Arkenau |
| 2006/0062856 A1 | 3/2006 | McGee |
| 2006/0093671 A1 | 5/2006 | McGee |
| 2006/0115876 A1 | 6/2006 | Pan |
| 2006/0128717 A1 | 6/2006 | Sun |
| 2006/0173029 A1 | 8/2006 | Chapman |
| 2006/0182801 A1 | 8/2006 | Breder |
| 2006/0193782 A1 | 8/2006 | Bartholomaus |
| 2006/0193914 A1 | 8/2006 | Ashworth |
| 2006/0194722 A1 | 8/2006 | Azria |
| 2006/0258669 A1 | 11/2006 | Kyle |
| 2006/0269604 A1 | 11/2006 | Sackler |
| 2007/0003616 A1 | 1/2007 | Arkenau-Maric |
| 2007/0014732 A1 | 1/2007 | Sackler |
| 2007/0020188 A1 | 1/2007 | Sackler |
| 2007/0048228 A1 | 3/2007 | Arkenau-Maric |
| 2007/0117829 A1 | 5/2007 | Chapman |
| 2007/0117830 A1 | 5/2007 | Chapman |
| 2007/0117831 A1 | 5/2007 | Chapman |
| 2007/0122348 A1 | 5/2007 | Kaiko |
| 2007/0141161 A1 | 6/2007 | Shaw |
| 2007/0148252 A1 | 6/2007 | Shaw |
| 2007/0166234 A1 | 7/2007 | Kumar |
| 2007/0179169 A1 | 8/2007 | Chapman |
| 2007/0183979 A1 | 8/2007 | Arkenau-Maric |
| 2007/0183980 A1 | 8/2007 | Arkenau-Maric |
| 2007/0197478 A1 | 8/2007 | Jones |
| 2007/0202049 A1 | 8/2007 | Guimberteau |
| 2007/0207089 A1 | 9/2007 | Abreu |
| 2007/0215511 A1 | 9/2007 | Mehta |
| 2007/0237832 A1 | 10/2007 | Sackler |
| 2007/0237833 A1 | 10/2007 | Sackler |
| 2007/0259045 A1 | 11/2007 | Mannion |
| 2007/0264327 A1 | 11/2007 | Kumar |
| 2007/0298103 A1 | 12/2007 | Hayes |
| 2008/0031963 A1 | 2/2008 | Sackler |
| 2008/0069881 A1 | 3/2008 | Caruso |

(56) References Cited

U.S. PATENT DOCUMENTS

| | | |
|---|---|---|
| 2008/0132532 A1 | 6/2008 | Wright |
| 2008/0166405 A1 | 7/2008 | Mehta |
| 2008/0199530 A1 | 8/2008 | Hirsh |
| 2008/0233197 A1 | 9/2008 | Matthews |
| 2008/0247959 A1 | 10/2008 | Bartholomaus |
| 2008/0260819 A1 | 10/2008 | Fleming |
| 2008/0292694 A1 | 11/2008 | Kaiko |
| 2008/0292700 A1 | 11/2008 | Nghiem |
| 2008/0311049 A1 | 12/2008 | Arkenau-Maric |
| 2008/0311187 A1 | 12/2008 | Ashworth |
| 2008/0312264 A1 | 12/2008 | Arkenau-Maric |
| 2008/0317854 A1 | 12/2008 | Arkenau |
| 2009/0004292 A1 | 1/2009 | Kumar |
| 2009/0005408 A1 | 1/2009 | Arkenau-Maric |
| 2009/0011024 A1 | 1/2009 | Babcock |
| 2009/0011028 A1 | 1/2009 | Checot |
| 2009/0022790 A1 | 1/2009 | Flath |
| 2009/0081287 A1 | 3/2009 | Wright |
| 2009/0081290 A1 | 3/2009 | McKenna |
| 2009/0098119 A1 | 4/2009 | Lu |
| 2009/0148517 A1 | 6/2009 | Oshlack |
| 2009/0162450 A1 | 6/2009 | Matthews |
| 2009/0162451 A1 | 6/2009 | Matthews |
| 2009/0175937 A1 | 7/2009 | Rahmouni |
| 2009/0175939 A1 | 7/2009 | Bosse |
| 2009/0202629 A1 | 8/2009 | Oshlack |
| 2009/0202634 A1 | 8/2009 | Jans |
| 2009/0227615 A1 | 9/2009 | Chapman |
| 2009/0238868 A1 | 9/2009 | Mehta |
| 2009/0253730 A1 | 10/2009 | Kumar |
| 2009/0297617 A1 | 12/2009 | Rariy |
| 2010/0028389 A1 | 2/2010 | Merrill |
| 2010/0081615 A1 | 4/2010 | Pan |
| 2010/0098771 A1 | 4/2010 | Mehta |
| 2010/0125052 A1 | 5/2010 | Lu |
| 2010/0143483 A1 | 6/2010 | Matthews |
| 2010/0151028 A1 | 6/2010 | Ashworth |
| 2010/0152449 A1 | 6/2010 | Chapman |
| 2010/0166858 A1 | 7/2010 | Mehta |
| 2010/0168148 A1 | 7/2010 | Wright |
| 2010/0172974 A1 | 7/2010 | Oshlack |
| 2010/0203130 A1 | 8/2010 | Tygesen |
| 2010/0204259 A1 | 8/2010 | Tygesen |
| 2010/0209351 A1 | 8/2010 | Sackler |
| 2010/0209514 A1 | 8/2010 | Sackler |
| 2010/0216829 A2 | 8/2010 | Kumar |
| 2010/0225131 A1 | 9/2010 | Weber |
| 2010/0239662 A1 | 9/2010 | Rahmouni |
| 2010/0240675 A1 | 9/2010 | Kyle |
| 2010/0255000 A1 | 10/2010 | Sinha |
| 2010/0260834 A1 | 10/2010 | Hirsh |
| 2010/0261713 A1 | 10/2010 | Sackler |
| 2010/0273730 A1 | 10/2010 | Hsu |
| 2010/0278881 A1 | 11/2010 | Azria |
| 2010/0291203 A1 | 11/2010 | Kaiko |
| 2010/0331369 A1 | 12/2010 | Sun |
| 2011/0002985 A1 | 1/2011 | Shah |
| 2011/0038927 A1 | 2/2011 | Oshlack |
| 2011/0071192 A1 | 3/2011 | Sun |
| 2011/0076325 A1 | 3/2011 | Shah |
| 2011/0077238 A1 | 3/2011 | Leech |
| 2011/0091542 A1 | 4/2011 | Navon |
| 2011/0104214 A1 | 5/2011 | Oshlack |
| 2011/0117192 A1 | 5/2011 | Navon |
| 2011/0142943 A1 | 6/2011 | Rariy |
| 2011/0150969 A1 | 6/2011 | Shah |
| 2011/0150970 A1 | 6/2011 | Shah |
| 2011/0150971 A1 | 6/2011 | Shah |
| 2011/0150989 A1 | 6/2011 | Park |
| 2011/0150990 A1 | 6/2011 | Shah |
| 2011/0150991 A1 | 6/2011 | Shah |
| 2011/0159089 A1 | 6/2011 | Shah |
| 2011/0159090 A1 | 6/2011 | Shah |
| 2011/0184007 A1 | 7/2011 | Shah |
| 2011/0207762 A1 | 8/2011 | Chapman |
| 2011/0230510 A1 | 9/2011 | Oshlack |
| 2011/0236487 A1 | 9/2011 | Shaw |
| 2011/0256226 A1 | 10/2011 | Breder |
| 2011/0262532 A1 | 10/2011 | Oshlack |
| 2011/0287095 A1 | 11/2011 | Park |
| 2011/0300217 A1 | 12/2011 | Merrill |
| 2012/0015030 A1 | 1/2012 | Mehta |
| 2012/0021051 A1 | 1/2012 | Masri |
| 2012/0034171 A1 | 2/2012 | Arkenau-Maric |
| 2012/0052098 A1 | 3/2012 | Shaw |
| 2012/0087982 A1 | 4/2012 | Kumar |
| 2012/0088786 A1 | 4/2012 | Dadagher |
| 2012/0107250 A1 | 5/2012 | Bartholomäus |
| 2012/0108621 A1 | 5/2012 | Brä-gmann |
| 2012/0108622 A1 | 5/2012 | Wright |
| 2012/0135077 A1 | 5/2012 | Mehta |
| 2012/0141583 A1 | 6/2012 | Mannion |
| 2012/0148672 A1 | 6/2012 | Mehta |
| 2012/0156277 A1 | 6/2012 | Shah |
| 2012/0164209 A1 | 6/2012 | Shah |
| 2012/0164220 A1 | 6/2012 | Huang |
| 2012/0165359 A1 | 6/2012 | Kaiko |
| 2012/0183612 A1 | 7/2012 | Brägmann |
| 2012/0189705 A1 | 7/2012 | Matthews |
| 2012/0201761 A1 | 8/2012 | Sackler |
| 2012/0201888 A1 | 8/2012 | Bosse |
| 2012/0201895 A1 | 8/2012 | Matthews |
| 2012/0225901 A1 | 9/2012 | Leyendecker |
| 2012/0251637 A1 | 10/2012 | Bartholomäus |
| 2012/0252832 A1 | 10/2012 | Caruso |
| 2012/0263788 A1 | 10/2012 | Oshlack |
| 2012/0269788 A1 | 10/2012 | Lu |
| 2012/0276017 A1 | 11/2012 | Lickrish |
| 2012/0288567 A1 | 11/2012 | Breder |
| 2012/0295988 A1 | 11/2012 | Babcock |
| 2013/0004575 A1 | 1/2013 | Nghiem |
| 2013/0005977 A1 | 1/2013 | Chapman |
| 2013/0017255 A1 | 1/2013 | Osvaldo |
| 2013/0034503 A1 | 2/2013 | Howard |
| 2013/0045960 A1 | 2/2013 | Hirsh |
| 2013/0059007 A1 | 3/2013 | Mehta |
| 2013/0084333 A1 | 4/2013 | Dick |
| 2013/0090349 A1 | 4/2013 | Geiäÿler |
| 2013/0122087 A1 | 5/2013 | Habib |
| 2013/0122101 A1 | 5/2013 | Habib |
| 2013/0129693 A1 | 5/2013 | Sinha |
| 2013/0136797 A1 | 5/2013 | Mehta |
| 2013/0156821 A1 | 6/2013 | Shaw |
| 2013/0158061 A1 | 6/2013 | Oshlack |
| 2013/0165418 A1 | 6/2013 | Kaiko |
| 2013/0171075 A1 | 7/2013 | Arkenau-Maric |
| 2013/0171257 A1 | 7/2013 | Kumar |
| 2013/0172382 A1 | 7/2013 | Caruso |
| 2013/0209560 A1 | 8/2013 | Hamed |
| 2013/0217716 A1 | 8/2013 | Wright |
| 2013/0230596 A1 | 9/2013 | Mehta |
| 2013/0245055 A1 | 9/2013 | Wright |
| 2013/0251759 A1 | 9/2013 | Jans |
| 2013/0251796 A1 | 9/2013 | McKenna |
| 2013/0251797 A1 | 9/2013 | McKenna |
| 2013/0251798 A1 | 9/2013 | McKenna |
| 2013/0251799 A1 | 9/2013 | McKenna |
| 2013/0251800 A1 | 9/2013 | McKenna |
| 2013/0251801 A1 | 9/2013 | McKenna |
| 2013/0251802 A1 | 9/2013 | McKenna |
| 2013/0251812 A1 | 9/2013 | Breder |
| 2013/0259938 A1 | 10/2013 | McKenna |
| 2013/0259939 A1 | 10/2013 | McKenna |
| 2013/0259940 A1 | 10/2013 | McKenna |
| 2013/0260015 A1 | 10/2013 | McKenna |
| 2013/0261143 A1 | 10/2013 | Wright |
| 2013/0261144 A1 | 10/2013 | Wright |
| 2013/0261145 A1 | 10/2013 | Wright |
| 2013/0273153 A1 | 10/2013 | Park |
| 2013/0274445 A1 | 10/2013 | Pan |
| 2013/0280176 A1 | 10/2013 | Diezi |
| 2013/0280177 A1 | 10/2013 | Raman |
| 2013/0287851 A1 | 10/2013 | Shaw |
| 2013/0289062 A1 | 10/2013 | Kumar |

(56) References Cited

U.S. PATENT DOCUMENTS

| | | |
|---|---|---|
| 2013/0295177 A1 | 11/2013 | Oshlack |
| 2013/0302418 A1 | 11/2013 | Oshlack |
| 2013/0303494 A1 | 11/2013 | Wright |
| 2013/0309303 A1 | 11/2013 | Breder |
| 2013/0310413 A1 | 11/2013 | Hirsh |
| 2013/0317051 A1 | 11/2013 | Oshlack |
| 2013/0320592 A1 | 12/2013 | Arkenau-Maric |
| 2013/0344142 A1 | 12/2013 | Rahmouni |
| 2014/0004191 A1 | 1/2014 | Rahmouni |
| 2014/0010873 A1 | 1/2014 | Tygesen |
| 2014/0010875 A1 | 1/2014 | Huang |
| 2014/0011832 A1 | 1/2014 | Huang |
| 2014/0017310 A1 | 1/2014 | Gower |
| 2014/0024669 A1 | 1/2014 | McKenna |
| 2014/0030322 A1 | 1/2014 | Bosse |
| 2014/0030327 A1 | 1/2014 | McKenna |
| 2014/0030334 A1 | 1/2014 | Mehta |
| 2014/0031381 A1 | 1/2014 | McKenna |
| 2014/0031382 A1 | 1/2014 | Leyendecker |
| 2014/0044773 A1 | 2/2014 | Lu |
| 2014/0045877 A1 | 2/2014 | Brägmann |
| 2014/0045878 A1 | 2/2014 | Brägmann |
| 2014/0050787 A1 | 2/2014 | Tygesen |
| 2014/0056984 A1 | 2/2014 | Mehta |
| 2014/0079684 A1 | 3/2014 | Lu |
| 2014/0079780 A1 | 3/2014 | Arkenau Maric |
| 2014/0080858 A1 | 3/2014 | Bartholomäus |
| 2014/0080915 A1 | 3/2014 | Bartholomäus |
| 2014/0086847 A1 | 3/2014 | Arkenau Maric |
| 2014/0086987 A1 | 3/2014 | Park |
| 2014/0099376 A2 | 4/2014 | Breder |
| 2014/0105830 A1 | 4/2014 | Bartholomäus |
| 2014/0105977 A1 | 4/2014 | Devarakonda |
| 2014/0105987 A1 | 4/2014 | Rariy |
| 2014/0107146 A1 | 4/2014 | Caruso |
| 2014/0112981 A1 | 4/2014 | Oshlack |
| 2014/0112984 A1 | 4/2014 | Arkenau-Maric |
| 2014/0113926 A1 | 4/2014 | Maric |
| 2014/0121232 A1 | 5/2014 | Hirsh |
| 2014/0127306 A1 | 5/2014 | Mehta |
| 2014/0134151 A1 | 5/2014 | Lu |
| 2014/0135355 A1 | 5/2014 | Caruso |
| 2014/0154309 A1 | 6/2014 | Shaw |
| 2014/0155388 A1 | 6/2014 | Brzeczko |
| 2014/0155425 A1 | 6/2014 | Sackler |
| 2014/0155426 A1 | 6/2014 | Sackler |
| 2014/0155489 A1 | 6/2014 | Arkenau-Maric |
| 2014/0170079 A1 | 6/2014 | Arkenau Maric |
| 2014/0170217 A1 | 6/2014 | Devarakonda |
| 2014/0187572 A1 | 7/2014 | Wright |
| 2014/0193494 A1 | 7/2014 | Rahmouni |
| 2014/0194456 A1 | 7/2014 | Caruso |
| 2014/0199394 A1 | 7/2014 | Oshlack |
| 2014/0200236 A1 | 7/2014 | Kaiko |
| 2014/0212461 A1 | 7/2014 | Lickrish |
| 2014/0212483 A1 | 7/2014 | Lickrish |
| 2014/0213606 A1 | 7/2014 | Wright |
| 2014/0220126 A1 | 8/2014 | Tygesen |
| 2014/0221416 A1 | 8/2014 | Guido |
| 2014/0227197 A1 | 8/2014 | Lickrish |
| 2014/0228390 A1 | 8/2014 | Wright |
| 2014/0248343 A1 | 9/2014 | Shah |
| 2014/0248344 A1 | 9/2014 | Shah |
| 2014/0248346 A1 | 9/2014 | Rahmouni |
| 2014/0249185 A1 | 9/2014 | Sun |
| 2014/0256764 A1 | 9/2014 | Abreu |
| 2014/0271735 A1 | 9/2014 | Azria |
| 2014/0271840 A1 | 9/2014 | Oshlack |
| 2014/0271849 A1 | 9/2014 | Raman |
| 2014/0275143 A1 | 9/2014 | Devarakonda |
| 2014/0288113 A1 | 9/2014 | Devarakonda |
| 2014/0294953 A1 | 10/2014 | Hamed |
| 2014/0294954 A1 | 10/2014 | Rahmouni |
| 2014/0294955 A1 | 10/2014 | Rahmouni |
| 2014/0294956 A1 | 10/2014 | Devarakonda |
| 2014/0296276 A1 | 10/2014 | Breder |
| 2014/0296277 A1 | 10/2014 | Brägmann |
| 2014/0314842 A1 | 10/2014 | Navon |
| 2014/0322311 A1 | 10/2014 | Ashworth |
| 2014/0322323 A1 | 10/2014 | Jans |
| 2014/0329847 A1 | 11/2014 | Ahdieh |
| 2014/0336213 A1 | 11/2014 | Kumar |
| 2014/0356294 A1 | 12/2014 | Arkenau-Maric |
| 2014/0357657 A1 | 12/2014 | Wright |
| 2014/0357658 A1 | 12/2014 | Kaiko |
| 2014/0371257 A1 | 12/2014 | Wright |
| 2014/0377348 A1 | 12/2014 | Oshlack |
| 2014/0377352 A1 | 12/2014 | Shah |
| 2014/0378498 A1 | 12/2014 | Devarakonda |
| 2015/0004244 A1 | 1/2015 | Rariy |
| 2015/0005331 A1 | 1/2015 | Wright |
| 2015/0005332 A1 | 1/2015 | Rariy |
| 2015/0005333 A1 | 1/2015 | Wright |
| 2015/0005335 A1 | 1/2015 | Brägmann |
| 2015/0005336 A1 | 1/2015 | Kaiko |
| 2015/0010624 A1 | 1/2015 | Navon |
| 2015/0024058 A1 | 1/2015 | Matthews |
| 2015/0024059 A1 | 1/2015 | Mehta |
| 2015/0025101 A1 | 1/2015 | Kaiko |
| 2015/0028512 A1 | 1/2015 | McKenna |
| 2015/0031718 A1 | 1/2015 | Wright |
| 2015/0037409 A1 | 2/2015 | Oshlack |
| 2015/0037411 A1 | 2/2015 | McKenna |
| 2015/0037412 A1 | 2/2015 | McKenna |
| 2015/0037413 A1 | 2/2015 | McKenna |
| 2015/0044282 A1 | 2/2015 | Shah |
| 2015/0057228 A1 | 2/2015 | Lu |
| 2015/0064245 A1 | 3/2015 | Shah |
| 2015/0064246 A1 | 3/2015 | Shah |
| 2015/0064247 A1 | 3/2015 | Shah |
| 2015/0064248 A1 | 3/2015 | Shah |
| 2015/0071995 A1 | 3/2015 | Shah |
| 2015/0071998 A1 | 3/2015 | Shah |
| 2015/0080384 A1 | 3/2015 | Leech |
| 2015/0110868 A1 | 4/2015 | Lickrish |
| 2015/0110870 A1 | 4/2015 | Oshlack |
| 2015/0110879 A1 | 4/2015 | Breder |
| 2015/0118302 A1 | 4/2015 | Haswani |
| 2015/0118303 A1 | 4/2015 | Haswani |
| 2015/0125521 A1 | 5/2015 | Lickrish |
| 2015/0140083 A1 | 5/2015 | Wright |
| 2015/0140086 A1 | 5/2015 | Flath |
| 2015/0140095 A1 | 5/2015 | Oshlack |
| 2015/0147391 A1 | 5/2015 | Wright |
| 2015/0148319 A1 | 5/2015 | Wright |
| 2015/0148366 A1 | 5/2015 | Hayes |
| 2015/0148367 A1 | 5/2015 | Oshlack |
| 2015/0150978 A1 | 6/2015 | Arkenau-Maric |
| 2015/0164808 A1 | 6/2015 | Devarakonda |
| 2015/0164811 A1 | 6/2015 | Arkenau-Maric |
| 2015/0174121 A1 | 6/2015 | Oshlack |
| 2015/0182464 A1 | 7/2015 | Arkenau Maric |
| 2015/0182465 A1 | 7/2015 | Arkenau Maric |
| 2015/0182467 A1 | 7/2015 | Oshlack |
| 2015/0182628 A1 | 7/2015 | Wright |
| 2015/0196555 A1 | 7/2015 | Guido |
| 2015/0196556 A1 | 7/2015 | Guido |
| 2015/0196557 A1 | 7/2015 | Guido |
| 2015/0202300 A1 | 7/2015 | Guido |
| 2015/0216809 A1 | 8/2015 | Oshlack |
| 2015/0216810 A1 | 8/2015 | Oshlack |
| 2015/0231086 A1 | 8/2015 | Oshlack |
| 2015/0231125 A1 | 8/2015 | Lickrish |
| 2015/0231131 A1 | 8/2015 | Oshlack |
| 2015/0238418 A1 | 8/2015 | Oshlack |
| 2015/0238443 A1 | 8/2015 | Lickrish |
| 2015/0238481 A1 | 8/2015 | Wright |
| 2015/0246034 A1 | 9/2015 | Devarakonda |
| 2015/0250732 A1 | 9/2015 | Dick |
| 2015/0250781 A1 | 9/2015 | Habib |
| 2015/0258086 A1 | 9/2015 | Chapman |
| 2015/0258087 A1 | 9/2015 | Caruso |
| 2015/0258088 A1 | 9/2015 | Caruso |
| 2015/0258089 A1 | 9/2015 | Oshlack |

(56) References Cited

U.S. PATENT DOCUMENTS

| | | |
|---|---|---|
| 2015/0258090 A1 | 9/2015 | Oshlack |
| 2015/0265537 A1 | 9/2015 | Oshlack |
| 2015/0265596 A1 | 9/2015 | Hirsh |
| 2015/0265597 A1 | 9/2015 | Chapman |
| 2015/0265598 A1 | 9/2015 | Chapman |
| 2015/0265599 A1 | 9/2015 | McKenna |
| 2015/0265600 A1 | 9/2015 | McKenna |
| 2015/0265601 A1 | 9/2015 | McKenna |
| 2015/0265602 A1 | 9/2015 | Wright |
| 2015/0265603 A1 | 9/2015 | Wright |
| 2015/0265604 A1 | 9/2015 | Wright |
| 2015/0265605 A1 | 9/2015 | Wright |
| 2015/0265606 A1 | 9/2015 | Wright |
| 2015/0265607 A1 | 9/2015 | Wright |
| 2015/0272888 A1 | 10/2015 | Rahmouni |
| 2015/0272890 A1 | 10/2015 | Rahmouni |
| 2015/0272893 A1 | 10/2015 | Mehta |
| 2015/0273064 A1 | 10/2015 | Wright |
| 2015/0273065 A1 | 10/2015 | Wright |
| 2015/0283087 A1 | 10/2015 | Vamvakas |
| 2015/0283088 A1 | 10/2015 | Gosangari |
| 2015/0283128 A1 | 10/2015 | Wright |
| 2015/0283129 A1 | 10/2015 | Wright |
| 2015/0283130 A1 | 10/2015 | Wright |
| 2015/0283250 A1 | 10/2015 | Wright |
| 2015/0290138 A1 | 10/2015 | Arkenau-Maric |
| 2015/0297525 A1 | 10/2015 | Bosse |
| 2015/0297527 A1 | 10/2015 | Liang |
| 2015/0306040 A1 | 10/2015 | Bosse |
| 2015/0313843 A1 | 11/2015 | Shaw |
| 2015/0313849 A1 | 11/2015 | Lickrish |
| 2015/0313997 A1 | 11/2015 | Tygesen |
| 2015/0320685 A1 | 11/2015 | Bosse |
| 2015/0335580 A1 | 11/2015 | McKenna |
| 2015/0335582 A1 | 11/2015 | McKenna |
| 2015/0335583 A1 | 11/2015 | McKenna |
| 2015/0335584 A1 | 11/2015 | McKenna |
| 2015/0335585 A1 | 11/2015 | McKenna |
| 2015/0366816 A1 | 12/2015 | Lickrish |
| 2015/0366832 A1 | 12/2015 | Navon |
| 2015/0366861 A1 | 12/2015 | Sackler |
| 2015/0374628 A1 | 12/2015 | Wright |
| 2015/0374631 A1 | 12/2015 | Wright |
| 2015/0374821 A1 | 12/2015 | Brzeczko |
| 2016/0000703 A1 | 1/2016 | Micka |
| 2016/0000712 A1 | 1/2016 | Wright |
| 2016/0000717 A1 | 1/2016 | Wright |
| 2016/0000718 A1 | 1/2016 | Wright |
| 2016/0000719 A1 | 1/2016 | Wright |
| 2016/0000723 A1 | 1/2016 | Wright |
| 2016/0000776 A1 | 1/2016 | Wright |
| 2016/0002617 A1 | 1/2016 | Sinha |
| 2016/0008350 A1 | 1/2016 | Oshlack |
| 2016/0045449 A1 | 2/2016 | Lamson |
| 2016/0051474 A1 | 2/2016 | Bosse |
| 2016/0051633 A1 | 2/2016 | Pan |
| 2016/0058716 A1 | 3/2016 | Wright |
| 2016/0074332 A1 | 3/2016 | Tygesen |
| 2016/0106755 A1 | 4/2016 | Bosse |
| 2016/0136152 A1 | 5/2016 | Kao |
| 2016/0151277 A1 | 6/2016 | Wright |
| 2016/0151289 A1 | 6/2016 | Wright |
| 2016/0151290 A1 | 6/2016 | Wright |
| 2016/0151291 A1 | 6/2016 | Wright |
| 2016/0151297 A1 | 6/2016 | Wright |
| 2016/0151355 A1 | 6/2016 | Wright |
| 2016/0151356 A1 | 6/2016 | Wright |
| 2016/0151357 A1 | 6/2016 | Wright |
| 2016/0151358 A1 | 6/2016 | Wright |
| 2016/0151360 A1 | 6/2016 | Wright |
| 2016/0151499 A1 | 6/2016 | Wright |
| 2016/0151502 A1 | 6/2016 | Wright |
| 2016/0158373 A1 | 6/2016 | Mehta |
| 2016/0184299 A1 | 6/2016 | Devarakonda |
| 2016/0193156 A1 | 7/2016 | Lickrish |
| 2016/0199300 A1 | 7/2016 | Navon |
| 2016/0199312 A1 | 7/2016 | Lickrish |
| 2016/0199368 A1 | 7/2016 | Gosangari |
| 2016/0199388 A1 | 7/2016 | Brzeczko |
| 2016/0243041 A1 | 8/2016 | Devarakonda |
| 2016/0250203 A1 | 9/2016 | Haswani |
| 2016/0256392 A1 | 9/2016 | Haswani |
| 2018/0055837 A1 | 3/2018 | Hughey |
| 2018/0071278 A1 | 3/2018 | Yang |

OTHER PUBLICATIONS

DOW Amberlite and Duolite Ion Exchange Resident Excipients, Handling and Use Guide, Introduction and Ion Exchange Principles, (Mar. 2013), pp. 109.

ANTI-OVERINGESTION ABUSE DETERRENT COMPOSITIONS

CROSS REFERENCE TO RELATED APPLICATIONS

This application claims priority to U.S. Provisional Patent Application No. 62/512,446, that was filed on May 30, 2017 and which is in incorporated herein in its entirety by express reference thereto.

TECHNICAL FIELD

Described herein are abuse deterrent oral pharmaceutical compositions, methods for making the same, and methods of treatment using such compositions. In particular, oral abuse-deterrent pharmaceutical compositions that mitigate the risk of overingestion of one or more active pharmaceutical ingredients are described.

BACKGROUND

Increased attention has been drawn to the recreational use and abuse of prescription pharmaceutical compositions. The abuse, or non-medicinal use, of prescription pharmaceutical compositions is an increasing problem. Accordingly, preventing the abuse of prescription pharmaceuticals through the development of abuse-deterrent pharmaceutical compositions has become a high public health priority for the U.S. Food and Drug Administration (FDA). Prescription pharmaceutical compositions that are typically misused or abused fall, primarily, into three groups: (1) opioids prescribed for pain; (2) Central Nervous System (CNS) depressants prescribed for anxiety or sleep problems; and (3) stimulants, prescribed, for example, for attention deficit hyperactivity, narcolepsy, or obesity.

Methods for abusing prescription pharmaceutical compositions are varied and can include, for example, extraction, boiling, melting, volatilization, physical tampering (e.g., grinding, grating, crushing, etc.), or direct administration. For purposes of abuse, methods of administering active drug substances obtained from prescription pharmaceutical compositions or of the pharmaceutical compositions themselves are similarly diverse and include, for example, injection, smoking, snorting, swallowing, sublingual or buccal administration, chewing, or administration as an anal or vaginal suppository. Alcohol-induced "dose dumping," i.e., the rapid release of active pharmaceutical ingredients in the presence of a solvent such as ethanol, is also an abuse concern and a safety issue. Other methods include rapid extraction under aqueous boiling conditions.

There are a number of strategies for preventing the abuse of pharmaceuticals. Physical and chemical barriers can prevent the extraction of the drug or change the form of the drug making it less likely to be abused. Combinations of agonists and antagonists can be used, wherein the antagonist is only released upon product manipulation or tampering. Another strategy is to use aversive compounds that produce an unpleasant effect when the dosage form is tampered with. In addition, prodrugs can be used, which are only changed into the active form of the drug in the gastrointestinal tract. The pharmaceutical industry is utilizing these strategies to develop abuse-deterrent pharmaceutical compositions in order to reduce the potential for misuse of prescription pharmaceutical compositions.

Accordingly, there is a need for abuse-deterrent pharmaceutical compositions that have controlled release properties.

SUMMARY

One embodiment described herein is an oral pharmaceutical composition comprising: a release modifier, a flowability enhancer, one or more active pharmaceutical ingredients (API), and an ion exchanger, wherein a portion of the API is in a free form and a portion of the API is bound to the ion exchanger. In one aspect, the composition forms an abuse deterrent elastic semi-solid composition after being heated at a temperature of about 50° C. to about 80° C. for a time period of about 10 min to about 180 min and then cooling the composition to room temperature. In another aspect, a greater quantity of API is adsorbed by the ion exchanger when a plurality of dosage forms are simultaneously ingested or successively ingested over about a 4-hour period. In another aspect, the plurality of doses is 2 or greater. In another aspect, the plurality of doses is from 2 to 30. In another aspect, the portion of API bound to the ion exchanger is about 25% to about 90% of the total mass of API. In another aspect, the portion of API bound to the ion exchanger is about 50% to about 90%. In another aspect, the portion of API bound to the ion exchanger is about 70% to about 90%. In another aspect, the portion of API bound to the ion exchanger is about 70% to abou 85%. In another aspect, the portion of API bound to the ion exchanger is about 70% or about 85%. In another aspect, the portion of API bound to the ion exchanger is about 70%. In another aspect, the portion of API bound to the ion exchanger is about 85%. In another aspect, following ingestion of the composition by a subject, the one or more ion exchanger adsorbs a quantity of the one or more API and impedes its release into the subject's systemic circulation. In another aspect, the API comprises oxycodone or a pharmaceutically acceptable salt thereof. In another aspect, the API comprises oxycodone hydrochloride comprising >25 ppm of 14-hydroxycodeinone. In another aspect, the composition comprises: (a) about 35% to about 80% by mass of one or more flowability enhancers; (b) about 10% to about 50% by mass of one or more release modifiers; and (c) about 1% to 50% by mass ion exchanger; and (d) about 1% to about 30% by mass of an active pharmaceutical ingredient or salt thereof. In another aspect, the composition comprises: (a) about 35% to about 80% by mass of glyceryl monolinoleate; (b) about 10% to about 50% by mass of polyethylene oxide; (c) about 1% to 50% ion exchanger; and (d) about 1% to about 30% by mass of oxycodone hydrochloride. The composition of claim 1, further comprising: (a) about 0.1% to about 0.4% by mass of BHA; and (b) about 0.05% to about 0.1% by mass of BHT. In another aspect, the composition comprises: (a) about 50% to about 70% by mass of glyceryl monolinoleate; (b) about 2% to 50% ion exchanger; (c) about 25% to about 40% by mass of polyethylene oxide; (d) about 0.05% to about 0.4% by mass of BHA; (e) about 0.05% to about 0.1% by mass of BHT; and (f) about 1% to about 20% of by mass of oxycodone hydrochloride. In another aspect, the composition comprises: (a) about 1% to about 30% API; and (b) about 20% to 50% ion exchanger. In another aspect, the composition comprises: about 20% oxycodone; and about 80% polystyrene sulfonate or a salt thereof. In another aspect, the composition comprises: (a) about 2% to about 10% API; and (b) about 5% to about 50% ion exchanger; and (c) one or more pharmaceutically acceptable excipients. In another aspect, the composition is capable of achieving one or more of the following pharmacokinetic parameters: (a) a lower $C_{max}$ for the API as compared to an equivalent API dose lacking an ion exchanger; (b) a delayed $T_{max}$ for the API as compared to an equivalent API dose lacking an ion exchanger; (c) a similar plasma AUC for the API as compared to an equivalent API dose lacking an ion exchanger; (d) an extended absorption time for the API as compared to an equivalent API dose lacking an ion exchanger; or (e) an extended clearance time for the API as compared to an equivalent API dose lacking an ion exchanger. In another aspect, the composition exhibits an in vitro disintegration or dissolution rate comprises about 10% after about 60 min, about 20% after about 90 minutes, about 50% after about 120 min, about 70% after about 240 min, about 85% after about 480 minutes in simulated gastric fluid (pH 1.2) in an USP Apparatus III. In another aspect, the composition exhibits an in vitro disintegration or dissolution rate comprises about 50% after about 120 minutes in simulated gastric fluid (pH 1.2) in an USP Apparatus III. In another aspect, the composition is a non-layered semi-solid composition. In another aspect, the API comprises about 5 mg, about 10 mg, about 15 mg, about 20 mg, about 30 mg, about 40 mg, about 50 mg, about 60 mg, about 70 mg, about 80 mg, about 90 mg, about 100 mg, about 110 mg, or about 120 mg of oxycodone hydrochloride. In another aspect, the API comprises about 5 mg to about 120 mg of oxycodone hydrochloride. In another aspect, the composition comprises one or more antioxidants. In another aspect, the antioxidant comprises alpha-tocopherol, beta-tocopherol, gamma-tocopherol, delta-tocopherol, butylated hydroxyanisole (BHA), butylated hydroxytoluene (BHT), citric acid, ascorbic acid, carnosic acid, carnosol, rosmanol, epirosmanol, isorosmanol, methyl carnosate, rosmarinic acid, eugenol, eugenyl acetate, clove bud extract, methanolic extract, epigallocatechin gallate, epicatechin gallate, epigallocatechin, epicatechin, or a combination thereof. In another aspect, the antioxidant comprises butylated hydroxyanisole (BHA), butylated hydroxytoluene (BHT), or a combination thereof. In another aspect, the one or more antioxidants comprise about 0.05% to about 1% of the composition by mass. In another aspect, the composition further comprises one or more viscosity modifiers. In another aspect, the viscosity modifier comprises about 0.5% to about 10% of the composition by mass. In another aspect, the viscosity modifier comprises polyvinyl pyrrolidone, ethylcellulose, or a combination thereof. In another aspect, the composition comprises an API to ion exchanger mass ratio of about 1:1 to about 1:8. In another aspect, the composition comprises an API to ion exchanger mass ratio of about 1:2 to about 1:5. In another aspect, the wherein the composition comprises an API to ion exchanger mass ratio of about 1:2 to about 1:3. In another aspect, the ion exchanger comprises one or more cation exchange polymers or salts thereof. In another aspect, the ion exchanger comprises a sulfonated styrene and divinylbenzene copolymer or a salt thereof. In another aspect, the ion exchanger comprises polystyrene sulfonate or a salt thereof. In another aspect, the flowability enhancer comprises a non-ionic surfactant, an anionic surfactant, a zwitterionic surfactant, a cationic surfactant, or a combination thereof. In another aspect, the flowability enhancer comprises a non-ionic surfactant. In another aspect, the flowability enhancer comprises a hydrophilic lipophilic balance of less than about 5. In another aspect, the flowability enhancer comprises medium chain triglycerides, monoglycerides, diglycerides and triglycerides, polyethylene glycol, glyceryl monooleate, glyceryl monostearate, glyceryl monolinoleate, oleic acid, glyceryl monocaprylate, polyglyceryl-3-dioleate, oleoyl macrogol-6 glycerides, linoleoyl macrogol-6 glyceride or a combination thereof. In another aspect, the flowability enhancer comprises a medium chain mono-, di-, or tri-glyceride; or a liquid lipophilic vehicle. In another aspect, the flowability enhancer comprises glyceryl monolinoleate. In another aspect, the flowability enhancer comprises about 35% to about 80% of the composition by mass. In another aspect, the release modifier comprises polyethylene oxide, a carboxyvinyl polymer, or a combination thereof. In another aspect, the release modifier comprises a polyethylene oxide having a molecular weight ($M_v$) of about 1,000,000; about 2,000,000; about 3,000,000; about 4,000,000; about 5,000,000; about 6,000,000; about 7,000,000; about 8,000,000; about 9,000,000; or about 10,000,000. In another aspect, the release modifier comprises a polyethylene oxide having a molecular weight ($M_v$) of about 1,00,000 to about 7,000,000. In another aspect, the release modifier comprises a polyethylene oxide having a molecular weight ($M_v$) of about 4,000,000. In another aspect, the release modifier comprises about 10% to about 50% of the composition by mass. In another aspect, the API comprises about 0.5% to about 35% of the composition by mass. In another aspect, a ratio of the API mass to the composition mass comprises a range of about 1:1000 to about 1:2. In another aspect, a ratio of release modifier to flowability enhancer is about 1:8. In another aspect, a ratio of the API to release modifier comprises a range of about 1:1 to about 1:20. In another aspect, a ratio of the release modifier to glyceryl monolinoleate is about 1:8. In another aspect, the glyceryl monolinoleate comprises about 35% to about 80% of the composition by mass. In another aspect, the polyethylene oxide comprises about 10% to about 50% of the composition by mass. In another aspect, the composition is encapsulated in a capsule.

Another embodiment described herein is an oral pharmaceutical composition comprising: a release modifier, a flowability enhancer, a viscosity modifier, one or more of antioxidants, one or more active pharmaceutical ingredients (API), an ion exchanger, wherein a portion of the API is in a free form and a portion of the API is bound to the one or more ion exchanger, and following ingestion of the composition by a subject, the ion exchanger adsorbs a quantity of the API and impedes its release into the subject's systemic circulation.

Another embodiment described herein is an oral abuse deterrent controlled release dosage form comprising a capsule encapsulating: (a) about 50% to about 70% by mass glyceryl monolinoleate; (b) about 25% to about 40% by mass polyethylene oxide comprising an average molecular weight ($M_v$) of about 4,000,000; (c) about 20% to 90% of one or more ion exchanger; and (d) about 1% to about 20% by mass of oxycodone hydrochloride, wherein a portion of oxycodone hydrochloride is in a free form and a portion of oxycodone hydrochloride is bound to the one or more ion exchanger; and wherein upon ingestion of more than one dosage form by a subject, the ion exchanger adsorbs a quantity of the API and impedes its absorption into the subject's systemic circulation. In one aspect, the dosage form has been heated to about 50° C. to about 80° C. for about 10 min to about 180 min, and cooled to room temperature by reducing the temperature at a rate of about 2° C. to about 10° C. over about 5 to about 15 minutes.

Another embodiment described herein is an oral abuse deterrent controlled release dosage form comprising a capsule encapsulating: about 35% to about 80% by mass of one or more flowability enhancers; about 10% to about 50% by mass of one or more release modifiers; about 1% to 50% of one or more ion exchanger; and about 1% to about 30% by mass of one or more API, wherein a portion of the API is in a free form and a portion of API is bound to the one or more ion exchanger; and the dosage form having been heated to about 50° C. to about 80° C. for about 10 min to about 180 min, and cooled to room temperature. In one aspect, upon ingestion of more than one dosage form by a subject, the one or more ion exchanger adsorbs a quantity of the API and impedes its absorption into the subject's systemic circulation. In another aspect, the dosage form having been heated to about 50° C. to about 80° C. for about 10 min to about 180 min, and cooled to room temperature by reducing the temperature at a rate of about 2° C. to about 10° C. over about 5 to about 15 minutes. In another aspect, wherein the API comprises oxycodone, hydrocodone, oxymorphone, hydromorphone, morphine, codeine, methadone, fentanyl, tapentadol, tramadol, meperidine, propoxyphene, flunitrazepam, barbiturates, amytal, nembutal, seconal, phenobarbital; benzodiazepines, zolpidem, zaleplon, eszopiclone, amphetamines, methylphenidate, a salt thereof, or a combination thereof. In another aspect, wherein a capsule encapsulating comprising: about 50% to about 70% by mass glyceryl monolinoleate; about 25% to about 40% by mass polyethylene oxide comprising an average molecular weight ($M_v$) of about 4,000,000; about 20% to about 90% of one or more ion exchanger; and about 1% to about 20% by mass of oxycodone or a pharmaceutically acceptable salt thereof. In another aspect, comprising about 5 mg of oxycodone hydrochloride, about 10 mg of oxycodone hydrochloride, about 15 mg of oxycodone hydrochloride, about 20 mg of oxycodone hydrochloride, about 30 mg of oxycodone hydrochloride, about 40 mg of oxycodone hydrochloride, about 50 mg of oxycodone hydrochloride, about 60 mg of oxycodone hydrochloride, about 70 mg of oxycodone hydrochloride, about 80 mg of oxycodone hydrochloride, about 90 mg of oxycodone hydrochloride, about 100 mg of oxycodone hydrochloride, about 110 mg of oxycodone hydrochloride, about 120 mg of oxycodone hydrochloride, about 130 mg of oxycodone hydrochloride, about 140 mg of oxycodone hydrochloride, about 150 mg of oxycodone hydrochloride, about 160 mg of oxycodone hydrochloride, or about 170 mg of oxycodone hydrochloride. In another aspect, wherein the capsule is coated with a polyvinyl alcohol coating. In another aspect, wherein the dosage form exhibits an in vitro disintegration or dissolution rate comprises about 50% after about 120 min in simulated gastric fluid (pH 1.2) in an USP Apparatus III. In another aspect, wherein a greater quantity of API is adsorbed by the ion exchanger when a plurality of dosage forms are simultaneously ingested or successively ingested over about a 4-hour period. In another aspect, wherein the plurality of doses is 2 or greater. In another aspect, wherein the plurality of doses is from 2 to 30.

Another embodiment described herein is a method for manufacturing an abuse deterrent dosage form comprising: ing a release modifier, a flowability enhancer, one or more active pharmaceutical ingredients (API), and an ion exchanger, wherein a portion of the API is in a free form and a portion of the API is bound to the ion exchanger; encapsulating the combination in soft capsules using rotary die encapsulation; incubating the capsules at an elevated temperature for a period of time; and cooling the capsules to room temperature. In another aspect, the capsules produced in step (b) are coated with a coating prior to the incubating of step (c). In another aspect, the capsules are incubated in step (c) at about 50° C. to about 80° C. for about 10 min to about 180 min. In another aspect, the capsules are cooled in step (d) by reducing the temperature at a rate of about 2° C. to about 10° C. over about 5 to about 15 min (e.g., a decrease of about 5° C. every 10 min). In another aspect, the API comprises oxycodone or a pharmaceutically acceptable salt thereof. In another aspect, the flowability enhancer comprises glyceryl monolinoleate. In another aspect, the one or more of a release modifier of step (a) comprises polyethylene oxide, a carboxyvinyl polymer, or a combination thereof. In another aspect, the one or more of a release modifier of step (a) comprises one or more polyethylene oxides. In another aspect, the one or more pharmaceutically acceptable excipients of step (a), comprises one or more antioxidants.

A method for treating pain, comprising administering to a subject a pharmaceutical dosage form as described herein, the method capable of achieving one or more of the following pharmacokinetic parameters: (a) a mean plasma oxycodone $T_{max}$ of about 4.5 hours to about 5.0 hours; (b) a mean plasma oxycodone $C_{max}$ of about 40 ng/mL to about 65 ng/mL; (c) a mean plasma oxycodone $AUC_{0 \to \tau}$ of about 400 h·ng/mL to about 500 h·ng/mL; (d) a mean plasma oxycodone $AUC_{0 \to \tau}$ of about 400·h·ng/mL to about 500 h·ng/mL; (e) a mean oxycodone half-life ($t_{1/2}$) of about 4.4 hours to about 4.6 hours; or (f) a mean oxycodone overall elimination rate constant ($\lambda_z$) of about 0.14 h-1 to about 0.17 h-1.

Another embodiment described herein is a method for treating pain while mitigating the risk of overingestion, the method comprising administering to a subject in need thereof an oral abuse-deterrent controlled release pharmaceutical dosage form comprising one or more of an API, one or more of an ion exchanger wherein a portion of the API is in a free from and a portion of the API is bound to the one or more ion exchanger, one or more of a flowability enhancer, one or more of a release modifier, and optionally, one or more pharmaceutically acceptable excipients; the dosage form having been heated to about 50° C. to about 80° C. for about 10 min to about 180 min, and cooled to room temperature, and following ingestion of at least one dose by a subject, the ion exchanger adsorbs a quantity of the API and impedes its release into the subject's systemic circulation. In another aspect, the API to ion exchanger mass ratio is about 1:1 to about 1:3. In another aspect, the portion of API bound to the one or more ion exchangers is about 70% to about 90%. In another aspect, a greater quantity of API is adsorbed by the one or more ion exchangers when a plurality of doses of the composition are simultaneously ingested or successively ingested over about a 4-hour period. In another aspect, the plurality of doses is 2 or greater. In another aspect, the plurality of doses is from 2 to 30. In another aspect, the composition is capable of achieving one or more of the following pharmacokinetic parameters: (a) a lower $C_{max}$ for the API as compared to an equivalent API dose lacking an ion exchanger; (b) a delayed $T_{max}$ for the API as compared to an equivalent API dose lacking an ion exchanger; (c) a similar plasma AUC for the API as compared to an equivalent API dose lacking an ion exchanger; (d) an extended absorption time for the API as compared to an equivalent API dose lacking an ion exchanger; or (e) an extended clearance time for the API as compared to an equivalent API dose lacking an ion exchanger. In another aspect, the API comprises oxycodone or a pharmaceutically acceptable salt thereof. In another aspect, the ion exchanger comprises one or more ion exchange polymers. In another aspect, the composition comprises: (a) about 35% to about 80% by mass of one or more flowability enhancers; (b) about 1% to 50% ion exchanger; (c) about 10% to about 50% by mass of one or more release modifiers; and (d) about 1% to about 30% by mass of an API. In another aspect, the composition comprises: (a) about 35% to about 80% by mass of glyceryl monolinoleate; (b) about 1% to 50% ion exchanger; (c) about 10% to about 50% by mass of polyethylene oxide; and (d) about 1% to about 30% by mass of oxycodone hydrochloride. In another aspect, the composition further comprises: (a) about 0.1% to about 0.4% by mass of BHA; and (b) about 0.05% to about 0.1% by mass of BHT. In another aspect, the composition comprises: (a) about 50% to about 70% by mass of glyceryl monolinoleate; (b) about 2% to 50% ion exchanger; (c) about 25% to about 40% by mass of polyethylene oxide; (d) about 0.05% to about 0.4% by mass of BHA; (e) about 0.05% to about 0.1% by mass of BHT; and (f) about 1% to about 20% of by mass of oxycodone hydrochloride. In another aspect, the composition is encapsulated in a capsule. In another aspect, the composition exhibits an in vitro disintegration or dissolution rate comprising about 50% disintegration or dissolution after about 1 minute to about 15 minutes in simulated gastric fluid (pH 1.2) in a USP Apparatus III. In another aspect, the pain arises from one or more of diabetic neuropathy, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, granuloma annulare, trauma, cancer, or a combination thereof.

Another embodiment described herein is a method for treating pain while mitigating the risk of overingestion, the method comprising administering to a subject in need thereof an oral abuse-deterrent controlled release pharmaceutical dosage form comprising one or more API, one or more ion exchangers wherein a portion of the API is in a free from and a portion of the API is bound to the one or more ion exchanger, one or more of a flowability enhancer, one or more of a release modifier, and optionally, one or more pharmaceutically acceptable excipients; the dosage form having been heated to about 50° C. to about 80° C. for about 10 min to about 180 min, and cooled to room temperature by reducing the temperature at a rate of about 2° C. to about 10° C. for about 5 to about 15 min, and following ingestion of at least one dose by a subject, the ion exchanger adsorbs a quantity of the API and impedes its release into the subject's systemic circulation.

Another embodiment described herein is a method for inhibiting extraction of oxycodone from a pharmaceutical composition, the method comprising: providing the dosage form of claim 65, wherein the dosage form is resistant to crushing, grating, grinding, cutting, solvation, or dissolution in water or alcohol.

Another embodiment described herein is a kit comprising one or more dosage forms comprising one or more oral immediate release pharmaceutical composition, and one or more of a controlled release pharmaceutical composition comprising one or more API, one or more ion exchangers, one or more of a flowability enhancer, one or more of a release modifier, wherein a portion of the API is in a free from and a portion of the API is bound to the one or more ion exchanger, wherein the composition forms an abuse deterrent elastic semi-solid composition after being heated at a temperature of about 50° C. to about 80° C. for a time period of about 10 min to about 180 min and then cooling the composition to room temperature. In one aspect, following ingestion of at least one dose by a subject, the ion exchanger adsorbs a quantity of the API and impedes its release into systemic circulation. In another aspect, the kit further comprises one or more moisture proof dispensing receptacles; and optionally an insert comprising instructions, prescribing information, contraindications, or warnings. In another aspect, the dosage form is abuse deterrent.

Another embodiment described herein is a method for regulating the concentration of an API in a subject's systemic circulation, the method comprising administering to a subject one or more oral abuse-deterrent controlled release pharmaceutical dosage form comprising one or more API, one or more of an ion exchanger, one or more of a flowability enhancer, one or more of a release modifier and optionally, one or more pharmaceutically acceptable excipients, wherein the composition forms an abuse deterrent elastic semi-solid composition after being heated at a temperature of about 50° C. to about 80° C. for a time period of about 10 min to about 180 min and then cooling the composition to room temperature, wherein a portion of the API is in a free from and a portion of the API is bound to the one or more ion exchanger, and following ingestion of at least one dose by a subject, the ion exchanger adsorbs a quantity of the API and impedes its release into the subject's systemic circulation. In another aspect, the portion of API bound to the one or more ion exchangers is about 5% to about 90%. In another aspect, the API to ion exchanger mass ratio is about 1:1 to about 1:8. In another aspect, the quantity of the API adsorbed by the ion exchanger is about 0.1% to about 10%. In another aspect, the quantity of the API adsorbed by the ion exchanger is about 0.5% to about 4%. In another aspect, the quantity of the API adsorbed by the ion exchanger is about 0.5% to about 3%. In another aspect, a greater quantity of API is adsorbed by the ion exchanger when a plurality of doses of the composition are simultaneously ingested or successively ingested over about a 4-hour period. In another aspect, the plurality of doses is 2 or greater. In another aspect, the plurality of doses is from 2 to 30. In another aspect, the composition is capable of achieving one or more of the following pharmacokinetic parameters: (a) a lower $C_{max}$ for the API as compared to an equivalent API dose lacking an ion exchanger; (b) a delayed $T_{max}$ for the API as compared to an equivalent API dose lacking an ion exchanger; (c) a similar plasma AUC for the API as compared to an equivalent API dose lacking an ion exchanger; (d) an extended absorption time for the API as compared to an equivalent API dose lacking an ion exchanger; or (e) an extended clearance time for the API as compared to an equivalent API dose lacking an ion exchanger. In another aspect, the composition comprises: (a) about 35% to about 80% by mass of one or more flowability enhancers; (b) about 1% to 50% ion exchanger; (c) about 10% to about 50% by mass of one or more release modifiers; and (d) about 1% to about 30% by mass of an API or salt thereof. In another aspect, the composition comprises: (a) about 35% to about 80% by mass of glyceryl monolinoleate; (b) about 1% to 50% ion exchanger; (c) about 10% to about 50% by mass of polyethylene oxide; and (d) about 1% to about 30% by mass of oxycodone hydrochloride. In another aspect, the method further comprises: (a) about 0.1% to about 0.4% by mass of BHA; and (b) about 0.05% to about 0.1% by mass of BHT. In another aspect, the composition comprises: (a) about 50% to about 70% by mass of glyceryl monolinoleate; (b) about 2% to 50% ion exchanger; (c) about 25% to about 40% by mass of polyethylene oxide; (d) about 0.05% to about 0.4% by mass of BHA; (d) about 0.05% to about 0.1% by mass of BHT; and (e) about 1% to about 20% of by mass of oxycodone hydrochloride. In another aspect, the composition is encapsulated in a capsule or formed as a tablet. In another aspect, the composition exhibits an in vitro disintegration or dissolution rate comprising about 50% disintegration or dissolution after about 120 minutes in simulated gastric fluid (pH 1.2) in an USP Apparatus III. In another aspect, the method further comprises: (a) acquiring a bodily fluid from the subject; (b) measuring the concentration of the API in the subject's circulation; and (c) according to the measured API concentration and a desired optimal opioid therapeutic concentration, and (d) administering one or more doses of the composition comprising the API and an ion exchanger; or (e) administering an equivalent dose of the API comprising a composition lacking an ion exchanger; or (f) administering either one or more doses of the composition comprising the API and an ion exchanger or administering an equivalent dose of the API comprising a composition lacking an ion exchanger after a period of about 30 min to about 12 hours.

DETAILED DESCRIPTION

Figure 1:
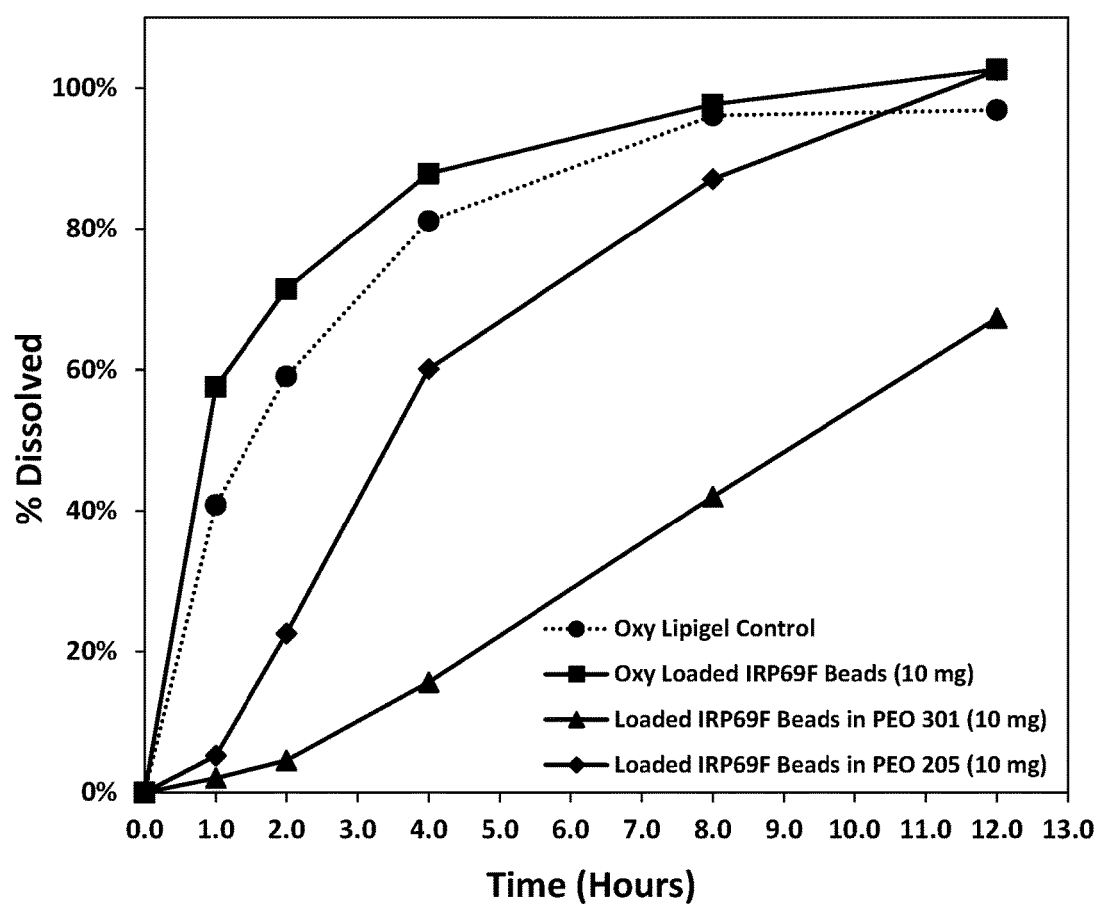
FIG. 1. Percent release of oxycodone from an annealed test abuse-deterrent pharmaceutical compositions Formulation 1 and Formulation 2 are compared to the percent release of oxycodone from reference abuse deterrent pharmaceutical compositions; Formulation 3 (non-annealed) and Formulation 4 (lacking ion exchanger) in fasted state simulated gastric fluid FaSSGF and fasted state simulated intestinal fluid FaSSIF buffer.

The term "abuse-deterrent," or "tamper resistant" as used herein, refers to a pharmaceutical composition that is resistant to tampering or accessing the active pharmaceutical ingredient for recreational drug use or drug abuse.

The phrase "recreational drug use," as used herein, refers to the voluntary use of an active pharmaceutical agent or drug for a non-medical purpose to induce an effect, such as pleasure, satisfaction, euphoria, dissociation, or to enhance an experience.

The term "drug abuse," as use herein, refers to the habitual, compulsive, or recurrent use of an active pharmaceutical agent or drug, often despite negative consequences.

The term "tampering," as used herein, refers to any kind of actual or attempted physical manipulation or interference that may result in particle size reduction of a pharmaceutical composition. Tampering, as used herein also includes any actual or attempted dissolution or extraction of active pharmaceutical ingredients using solvents. Compositions that are resistant to physical tampering are formulated in such a way that the composition cannot readily reduced to a form that is suitable for abuse, such as, for example, injection or snorting, because the tablet cannot easily be ground, grated, dissolved, extracted, and the like at any temperature. Examples of physical tampering include, but are not limited to, crushing, grinding, grating, cutting, crisping, and other methods of particle size reduction. Dissolution tampering includes actual or attempted actions to dissolve or extract active pharmaceutical ingredients using aqueous or organic solvents such as water, ethanol, isopropanol, ethyl acetate, acetone, ether, or the like, at any temperature including boiling. Tampering, as used herein, includes "dose dumping."

The term "dose dumping" or "dumping" as used herein refers to the rapid release of the entire amount or a significant fraction of an active pharmaceutical ingredient or drug. Drug abusers often intentionally pursue dumping of a drug from the dosage form.

The terms "drug", "active ingredient," "active pharmaceutical ingredient," or "active pharmaceutical agent" as used herein refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The terms "dosage" or "dose" or "dosage form" denote any form of the active ingredient formulation that contains an amount sufficient to produce a therapeutic effect with a single administration. The dosage form used herein is for oral administration. The oral dosage forms are soft capsules, enteric soft capsules, hard capsules, enteric hard capsules, or tablets.

The term "annealed" as used herein refers to a pharmaceutical composition that has been heated to an elevated temperature (e.g., 60° C. to 80° C.) for a time period (e.g., from 10 min to 180 min) and then slowly cooled (e.g., to room temperature) at a specific rate (e.g., 2° C. per 10 min) to form an annealed dosage form. In some aspects, pharmaceutical compositions comprising a capsule shell encapsulating a fill composition as described herein may be annealed at a temperature from about 50° C. to about 90° C. for about 0.1 hours to about 5 hours, including all integers within the specified ranges of temperature and time. In some aspects described herein, pharmaceutical compositions comprising a soft or hard capsule shell encapsulating a matrix fill as described herein may be annealed at a temperature of about 70° C. from about 20 min to about 90 min, including all integers within the specified range. In some aspects described herein, pharmaceutical compositions comprising a soft or hard capsule shell encapsulating a matrix fill as described herein may be annealed at a temperature of about 70° C. for about 1 hour. In some aspects, after annealing, the dosage form is slowly cooled to room temperature at a cooling rate of about 2° C. to about 10° C. per about 5 min to about 20 min (e.g., 2-10° C./5-20 min). In some aspects described herein, a capsule is coated prior to the annealing step.

The term "non-annealed" refers to a pharmaceutical composition comprising a soft or hard capsule shell encapsulating a matrix fill described herein that has not been heated following encapsulation.

The terms "active pharmaceutical ingredient load" or "drug load" as used herein refers to the quantity (mass) of the active pharmaceutical ingredient comprised in a single soft or hard capsule fill.

The term "loading" of the drug to the ion exchanger as used herein refers to the binding of the drug to an ion exchanger to form an ion exchanger-API complex prior to ingestion by a subject. The term "loading" is used interchangeably with "binding" or "pre-binding" of the drug in the pharmaceutical composition prior to ingestion by a subject.

The term "adsorption" as used herein refers to the holding or accumulation of the drug on the external or internal surfaces of the ion exchanger following ingestion of the dosage form by a subject, impeding release of the drug into the subject's systemic circulation.

The term "formulation" or "composition" as used herein refers to the active pharmaceutical ingredient or drug in combination with pharmaceutically acceptable excipients. This includes orally administrable formulations as well as formulations administrable by other means.

The term "titration" as used herein refers to the incremental increase in drug dosage to a level that provides the optimal therapeutic effect.

The term "controlled release" as used herein encompasses the terms "immediate release," "modified release," "sustained release," "extended release," and "delayed release."

The terms "extended release" or "sustained release" as used herein refers to a composition that releases an active ingredient according to a desired profile over an extended period under physiological conditions or in an in vitro test. By "extended period" it is meant a continuous period of time of at least about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically, over a period of about 18 hours under physiological conditions or in an in vitro assay.

The term "modified release" as used herein refers to a composition that releases an active ingredient at a slower rate than does an immediate release formulation under physiological conditions or in an in vitro test.

The term "delayed" release" as used herein refers to a composition that releases an active ingredient after a period of time, for example minutes or hours, such that the active ingredient is not released initially. A delayed release composition may provide, for example, the release of a drug or active ingredient from a dosage form, after a certain period, under physiological conditions or in an in vitro test.

As used herein, the phrase "abuse-deterrent controlled release" refers to a pharmaceutical composition comprising components or a formulation that prevents liberation of the active pharmaceutical ingredient(s) from the composition for potential abuse or dose dumping and the composition provides controlled release delivery of the active pharmaceutical ingredient upon ingestion of the composition by a subject.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{last}$" as used herein refers to the area under the blood (plasma, serum, or whole blood) concentration versus time curve at the last measurable concentration of the analyte, and is expressed in units of h·mg/L (or h·ng/mL) for at least one or more doses of the pharmaceutical compositions described herein.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The phrase "room temperature" as used herein refers to about 25° C. at standard atmospheric pressure.

The term "about" as used herein refers to any values, including both integers and fractional components that are within a variation of up to ±10% of the value modified by the term "about."

As used herein, "a" or "an" means one or more unless otherwise specified.

Terms such as "include," "including," "contain," "containing," "has," or "having," and the like, mean "comprising."

The term "or" can be conjunctive or disjunctive.

Described herein are pharmaceutical compositions comprising abuse-deterrent matrices comprising active pharmaceutical ingredients. The composition is structured to prevent extraction of the active pharmaceutical ingredients and the composition comprises one or more ion exchangers that limit the amount of API systemically absorbed when a plurality of dosage forms are consumed proximately in time (i.e., prior to gastric emptying, ~4 hours).

One embodiment described herein is an oral abuse-deterrent controlled release pharmaceutical composition that releases one or more active pharmaceutical ingredients (API) over a period of about 12 hours. In one aspect, the composition comprises an API that is bound to one or more ion exchangers. In another aspect, a portion of the API is in the free form and another portion is bound to the ion exchanger. In another aspect, the ion exchanger is a resin or a polyelectrolytic compound.

In some embodiments, the pharmaceutical composition described herein comprises a soft or hard capsule comprising an abuse-deterrent controlled release composition comprising an active pharmaceutical ingredient and one or more ion exchangers. In one embodiment, the active pharmaceutical ingredient is an analgesic. In another embodiment, the active pharmaceutical ingredient is an opioid agonist. In another embodiment, the active pharmaceutical ingredient is an opioid analgesic.

In other embodiments, the pharmaceutical composition described herein comprises abuse-deterrent properties. These abuse-deterrent properties reduce the likelihood that the active pharmaceutical ingredient can be extracted from the composition through mechanisms, including but not limited to crushing, grating, grinding, or cutting of the capsule to expose the matrix thereby facilitating solvation or extraction of the API. Exemplary and non-limiting abuse-deterrent matrices useful in the pharmaceutical composition described herein may be those found in International Application No. PCT/US2015/024464; U.S. patent application Ser. No. 14/679,233; PCT International Application No. PCT/US2015/054443; U.S. patent application Ser. No. 14/877,208, each of which is incorporated by reference herein in their entirety. In addition, the abuse-deterrent properties reduce the likelihood that the API can be extracted from the composition by dissolving or extracting in ethanol solutions, dissolving in solutions having pH values from about 1 to about 12, or dissolving in household chemical compositions, including water, coffee, vinegar, cola, milk, ethanol, isopropanol, acetone, ethyl acetate, or other common solvents. In addition, the abuse-deterrent properties further reduce the likelihood that the API can be extracted by boiling in water or ethanol solutions.

In other embodiments described herein, the composition comprises a lipid or lipophilic vehicle that provides a suspension or a solution of the API. In one aspect, a soft or hard capsule comprising an API provides controlled release of the API. In another aspect, a portion of the API is complexed with an ion exchanger. In another aspect, a portion of the API is not complexed with an ion exchanger, but is in the free form.

In other embodiments described herein, the pharmaceutical composition provides fills for the API, or derivatives thereof, based on lipids or lipophilic materials. The matrices described herein have a hydrophobic (lipophilic) surface in contact with a hydrophilic soft capsule shell to minimize any potential shell-fill interactions, such as when soft capsules are filled with hydrophilic materials. In one embodiment described herein are methods for manufacturing matrix fills comprising an abuse-deterrent controlled release matrix comprising an API in a soft capsule in the form of a suspension, where part or all of the API is suspended within the matrix. In one embodiment described herein is a soft capsule having a shell and an abuse-deterrent controlled release fill, wherein the fill composition includes an API suspended as particles within the matrix. In one aspect, the particles are free API. In another aspect, the particles are a resinate comprising an ion exchange resin and the API. In another aspect, the fill comprises both free API and a resinate comprising an ion exchange resin bound to a separate quantity of the API.

In one embodiment, the composition comprises one or more flowability enhancers. In one aspect, suitable flowability enhancers have surfactant like properties. Exemplary and non-limiting flowability enhancers shown in Table 1 may comprise partial triglyceride medium chain, monoglycerides, diglycerides and triglycerides, polyethylene glycol (molecular weight of about 200 or greater), medium chain triglycerides of caprylic/capric acid, glyceryl monooleate, glyceryl monostearate, glyceryl monolinoleate (e.g., Maisine™ 35-1), polyglyceryl-3-dioleate, oleoyl macrogol-6 glycerides, linoleoyl macrogol-6 glycerides. In one aspect, the flowability enhancer comprises a medium chain mono- and di-glycerides (e.g., glyceryl monocaprylate or Capmul® MCM). In another aspect, the flowability enhancer comprises oleic acid. In another aspect, the flowability enhancer comprises glyceryl monolinoleate (e.g., Maisine™ 35-1).

TABLE 1

Exemplary Abuse-deterrent Controlled Release Compositions

| Component | Exemplary Components | Mass Percent (%) |
| --- | --- | --- |
| Flowability Enhancer | Mono-, di-, tri-glycerides, glyceryl monocaprylate, oleic acid, glyceryl monolinoleate (e.g., Maisine ™ 35-1) | 35-80 |
| Release Modifier | Polyethylene oxide (PEO) (e.g., POLYOX ™) | 10-50 |
| Release Modifier 2 | Carboxyvinyl polymers (e.g., Carbopol ® polymers) | 0-10 |
| Viscosity Modifier | Polyvinylpyrrolidone, ethylcellulose | 0-10 |
| Ion Exchanger | Copolymers of acrylic acid, methacrylic acid, phenol-formaldehyde or dextran, styrene-divinyl benzene sulphonic acid resin (e.g., Amberlite ™ IRP 69, Amberlite ™ IRP 88) | 1-50 |
| Antioxidant | BHT, BHA | 0-1 |
| Active pharmaceutical ingredient(s) | Oxycodone, hydrocodone, tapentadol | 0.1-50 |

In another embodiment, the composition may comprise one or more surfactants as described herein. In one aspect, the flowability enhancer comprises a non-ionic surfactant, an anionic surfactant, a zwitterionic surfactant, or a cationic surfactant or a combination thereof. In another aspect, the flowability enhancer comprises a non-ionic surfactant. Exemplary and non-limiting surfactants that may be useful in the abuse-deterrent matrices described herein comprise Suitable surfactants include: Pluronic® 10R5, Pluronic® 17R2, Pluronic® 17R4, Pluronic® 25R2, Pluronic® 25R4, Pluronic® 31R1, Pluronic® F. 108, Pluronic® F. 108 NF, Pluronic® F. 108, Pluronic® F. 108NF, Poloxamer 338, Pluronic® F 127, Pluronic® F 127 NF, Pluronic® F 127 NF 500 BHT Prill, Pluronic® F 127 NF Prill, Poloxamer 407, Pluronic® F 38, Pluronic® F 38 Pastille, Pluronic® F 68, Pluronic® F 68 LF Pastille, Pluronic® F 68 NF, Pluronic® F 68 NF Prill, Poloxamer 188, Pluronic® F 68 Pastille, Pluronic® F 77, Pluronic® F 77 Micropastille, Pluronic® F 87, Pluronic® F 87 NF, Pluronic® F 87 NF Prill, Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen® 464, Alkanol® 6112, Brij® 52, Brij® 93, Brij® S2, Brij® S, Brij® 58, Brij® C10, Brij® L4, Brij® 010, Brij® 010, BRIJ® 020, Brij® S10, Brij® S20, ethylenediamine tetrakis(ethoxylate-block-propoxylate) tetrol, ethylenediamine tetrakis(ethoxylate-block-propoxylate) tetrol, ethylenediamine tetrakis(propoxylate-block-ethoxylate) tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly(ethylene glycol) sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, sodium lauryl sulfate, 2,4,7,9-tetramethyl-5-decyne-4,7-diol ethoxylate, Nonidet™ P-40, Triton™ N-101, Span® 80, Triton™ X-100, Triton™ X-114, Triton™ X-405, TWEEN® 20, TWEEN® 40, TWEEN® 60, TWEEN® 85, Zonyl® FS-300, or Zonyl® FSN.

Additional exemplary and non-limiting flowability enhancers may include higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, stearyl alcohol, and others known in the art.

In another embodiment, the flowability enhancer has a hydrophilic lipophilic balance (HLB) ranging from about 0 to about 20. In one aspect, the flowability enhancer has an HLB value of less than 10. In another aspect, the flowability enhancer has an HLB value of between 1 and 6. In another aspect, the flowability enhancer has an HLB value of less than 5. The HLB characteristic of surfactants and other compounds can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993).

In another embodiment, the composition comprises a lipid or lipophilic vehicles, such as olive oil, soybean oil, sunflower oil, canola oil, palmitoleic acid, oleic acid, myristoleic acid, linoleic acid, arachidonic acid, vegetable oil, corn oil, sun flower oil, coconut oil, cocoa oil, peanut oil, almond oil, cottonseed oil, persic oil, sesame oil, squalane oil, castor oil, fish oil, paraffin oil, or mineral oil.

In another embodiment, the composition comprises one or more release modifiers (Table 1). In one aspect, the release modifier comprises a high molecular weight polyethylene oxide or a carboxyvinyl polymer, or a combination thereof. As described herein, high molecular weight polyethylene oxide polymers have an approximate molecular weight based on viscosity or rheology ($M_v$) of at least about 600,000 to about 10,000,000 or greater. In one aspect, the release modifier may comprise a high molecular weight polyethylene oxide having a molecular weight ($M_v$) of about 600,000 to about 10,000,000, including each integer within the specified range. In another aspect, the release modifier may comprise a high molecular weight polyethylene oxide having a molecular weight ($M_v$) of about 5,000,000 to about 10,000,000, including each integer within the specified range. In another aspect, the release modifier may comprise a high molecular weight polyethylene oxide having a molecular weight ($M_v$) of about 4,000,000 to about 7,000,000, including each integer within the specified range. In another aspect, the release modifier may comprise a high molecular weight polyethylene oxide having a molecular weight ($M_v$) of about 600,000, about 700,000, about 800,000, about 900,000, about 1,000,000, about 2,000,000, about 3,000,000, about 4,000,000, about 5,000,000, about 6,000,000, about 7,000,000, about 8,000,000, about 9,000,000 or about 10,000,000. In another aspect, the release modifier may comprise a high molecular weight polyethylene oxide having a molecular weight ($M_v$) of about 4,000,000. In another aspect, the release modifier may comprise a high molecular weight polyethylene oxide having a molecular weight ($M_v$) of about 5,000,000. In another aspect, the release modifier may comprise a high molecular weight polyethylene oxide having a molecular weight ($M_v$) of about 7,000,000.

The molecular weight measurements of polyethylene oxide may be approximated using rheological measurements using a viscometer. For example, polyethylene oxide is considered to have an approximate molecular weight ($M_v$) of 600,000 when a 5% (by wt) aqueous solution of polyethylene oxide using a Brookfield viscometer Model RVF, spindle No. 2, at 2 rpm, at 25° C. shows a viscosity range of 30 to 50 mPa s (cP). Polyethylene oxide is considered to have an approximate molecular weight ($M_v$) of 1,000,000 when a 2% (by wt) aqueous solution of polyethylene oxide using a Brookfield viscometer Model RVF, spindle No. 1, at 10 rpm, at 25° C. shows a viscosity range of 400 to 800 mPa s (cP). Polyethylene oxide is considered to have an approximate molecular weight ($M_v$) of 2,000,000 when a 2% (by wt) aqueous solution of polyethylene oxide using a Brookfield viscometer Model RVF, spindle No. 3, at 10 rpm, at 25° C. shows a viscosity range of 2000 to 4000 mPa s (cP). Polyethylene oxide is considered to have an approximate molecular weight ($M_v$) of 4,000,000 when a 1% (by wt) aqueous solution of polyethylene oxide using a Brookfield viscometer Model RVF, spindle No. 2, at 2 rpm, at 25° C. shows a viscosity range of 1650 to 5500 mPa s (cP). Polyethylene oxide is considered to have an approximate molecular weight ($M_v$) of 5,000,000 when a 1% (by wt) aqueous solution of polyethylene oxide using a Brookfield viscometer Model RVF, spindle No. 2, at 2 rpm, at 25° C. shows a viscosity range of 5500 to 7500 mPa s (cP). Polyethylene oxide is considered to have an approximate molecular weight ($M_v$) of 7,000,000 when a 1% (by wt) aqueous solution of polyethylene oxide using a Brookfield viscometer Model RVF, spindle No. 2, at 2 rpm, at 25° C. shows a viscosity range of 7500 to 10,000 mPa s (cP). Polyethylene oxide is considered to have an approximate molecular weight ($M_v$) of 8,000,000 when a 1% (by wt) aqueous solution of polyethylene oxide using a Brookfield viscometer Model RVF, spindle No. 2, at 2 rpm, at 25° C. shows a viscosity range of 10,000 to 15,000 mPa s (cP). Suitable polyethylene oxide polymers with the above described viscosity and molecular weight values that are useful for the matrices described are, for example, POLYOX™ polymers, such as WSR-205, WSR-1105, WSR N-12K, WSRN-60K, WSR-301, WSR Coagulant, WSR-303, WSR 308, UCARFLOC Polymers 300, 302, 304, and 309 commercially available from Dow Chemical Company. In one aspect, the polyethylene oxide polymer is POLYOX™ WSR-301 ($M_v \approx 4,000,000$) or POLYOX™

WSR-303 ($M_v \approx 7,000,000$) (Dow Chemical Co.). In one aspect, the polyethylene oxide polymer is POLYOX™ WSR-301 ($M_v \approx 4,000,000$).

In another embodiment, the composition comprises one or more viscosity modifiers. Suitable and non-limiting viscosity modifiers that may be present in the matrices described herein comprise methylcellulose, ethylcellulose, hydroxypropylmethyl cellulose, hydroxypropyl cellulose, hydroxyethyl cellulose, hydroxymethyl cellulose, polymethylmethacrylate, polyhydroxyethylmethacrylate, polyvinylpyrrolidone, copovidone, polyvinyl alcohol, a copolymer of polyvinylpyrrolidone and polyvinyl acetate, or combinations thereof. For example, polymers commercially available as Methocel™ K 100M, Methocel™ A4M, Ethocel™, Premium LV CR, K4M Premium CR, K15M Premium CR, K100 Premium CR, E4M Premium CR, E10M Premium CR, or E4M Premium (Dow Chemical Co.), CELLOSIZE™, or WALOCEL™ CRT may be used in the abuse-deterrent matrices described herein. These viscosity modifiers may comprise a viscosity of about 50 cP to about 100,000 cP, including each integer within the specified range. For example, these additional release modifiers may comprise a viscosity of about 50 cP, about 100 cP, about 200 cP, about 300 cP, about 400 cP, about 500 cP, about 750 cP, about 1,000 cP, about 1,500 cP, about 2,000 cP, about 2,500 cP, about 3,000 cP, about 3,500 cP, about 4,000 cP, about 4,500 cP, about 5,000 cP, about 6,000 cP, about 7,000 cP, about 8,000 cP, about 9,000 cP, or about 10,000 cP, about 15,000 cP, about 20,000 cP, about 30,000 cP, about 40,000 cP, about 50,000 cP, about 60,000 cP, about 70,000 cP, about 80,000 cP, about 90,000 cP, about 100,000 cP, greater than 100,000 cP, or even greater. In one embodiment, the composition comprises hydroxylpropyl methylcellulose (e.g., Methocel™ K100M). In another embodiment, the composition comprises ethylcellulose (e.g., Ethocel™ 20 cP). In another embodiment, the composition comprises a polyvinylpyrrolidone (e.g., polyvinylpyrrolidone K90).

In one embodiment, the pharmaceutical composition comprises an API in complex with one or more ion exchangers. Suitable ion exchangers comprise water-insoluble and pharmacologically inert organic and/or inorganic matrices containing covalently bound functional groups that are ionic or capable of being ionized under appropriate pH conditions. The organic ion exchange composition comprises synthetic (e.g., polymers or copolymers of acrylic acid, methacrylic acid, sulfonated styrene, sulfonated divinylbenzene), or partially synthetic (e.g., modified cellulose and dextrans). The inorganic composition comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In one aspect, the ion exchange resin is a sulfonated styrene and divinylbenzene copolymer such as polystyrene sulfonate or a salt thereof (e.g., Amberlite™ IRP-69).

Exemplary ion exchangers for use in ion-exchange chromatography and for such applications as deionization of water are suitable for use in the compositions described herein. Suitable ion exchange resins are also sold under the trade names Amberlite™ and Dowex™. Both regularly and irregularly shaped particles may be used as resins. Regularly shaped particles are those particles that substantially conform to geometric shapes, such as spherical, elliptical, cylindrical and the like. Irregularly shaped ion exchangers of this type are exemplified by Amberlite™ IRP-69, which consists of irregularly-shaped particles with a size range of 47 microns to 149 microns. Such ion exchangers are described by H. F. Walton in "Principles of Ion Exchange" (pp. 312-343) and "Techniques and Applications of Ion-Exchange Chromatography" (pp. 344-361) in Chromatography. (E. Heftmann, editor), Van Nostrand Reinhold Company, New York (1975) and in U.S. Patent Application Publication No 2014/0127300, each of which is incorporated herein by reference for its teachings of ion exchange resins. Further exemplary ion exchanger are shown in Table 2.

TABLE 2

Exemplary Ion Exchangers

| Polymer | Exchanger type |
| --- | --- |
| Amberlite ™ IRP 69 | Strong Cation |
| Amberlite ™ 200/200C | Strong Cation |
| DOWEX ™ 50WX8H | Strong Cation |
| DOWEX ™ 88 | Strong Cation |
| Purolite ® C100HMR | Strong Cation |
| Purolite ® C100NaMR | Strong Cation |
| Purolite ® C100CaMR | Strong Cation |
| Lewatit K ® 1481 | Strong Cation |
| Lewasorb ® SW 12 | Strong Cation |
| Amberlite ™ IRP 64 | Weak Cation |
| Amberlite ™ IRP 88 | Weak Cation |
| Purolite ® C 115 K MR | Weak Cation |
| Purolite ® C 115 H MR | Weak Cation |
| Purolite ® C 108DR | Weak Cation |
| Lewatit ® CNP 105 | Weak Cation |
| PolyAMPs | Other |
| Polyvinylsulfonic acid (+derivatives) | Other |
| Polyvinylphosphonic acid (+derivatives) | Other |
| Poly acrylic acid (+derivatives) | Other |

Binding or loading of the APIs to the resins described herein may be accomplished using methods known in the art. For example, the general reactions may be used for a basic drug. These are: (a) resin (e.g., Na$^+$-form), and an ionic salt form of the drug being bound; (b) resin (e.g., Na$^+$-form) plus free base form of drug.

Analogous binding reactions can be carried out for binding an acidic drug, and an anion exchange resin. These are: (a) resin (e.g., Cl$^-$ form) plus the salt form of acidic drug to be bound; (b) resin (e.g., Cl$^-$ form) plus the free acid form of the drug to be bound; (c) resin (e.g., OH$^-$-form) plus salt form of drug to be bound; and (d) resin (e.g., OH$^-$-form) plus free acid form of drug to be bound.

Binding may be performed, for example, as a batch or column process, as is known in the art. The drug-resin complexes described herein may be prepared by a batch process that is based on reaction the exemplary reactions described herein. The drug to be loaded on the ion exchange resin may be dissolved in an aqueous medium or in a solvent miscible with water to make a solution. The drug-containing solution is then placed in a slurry of the resin or a column loaded with resin. The drug-resin resinate complex thus formed is collected by filtration and washed with deionized or purified water to ensure removal of any unbound drug.

In one embodiment described herein, the amount of drug loaded or bound onto the ion exchanger to form a resinate (i.e., a resin-drug complex) ranges from about 0.5% to about 85%, including each integer within the specified range. In one aspect, the amount of drug loaded onto the resin ranges from about 0.5% to about 70%, including each integer within the specified range. In another aspect, the amount of drug loaded onto the resin ranges from about 0.5% to about 50%, including each integer within the specified range. In another aspect, the amount of drug loaded onto the resin comprises about 70%. In another aspect, the amount of drug loaded onto the resin comprises about 60%. In another aspect, the amount of drug loaded onto the resin comprises about 50%. In another aspect, the amount of drug loaded onto the resin comprises about 40%. In another aspect, the amount of drug loaded onto the resin comprises about 30%. In another aspect, the amount of drug loaded onto the resin comprises about 20%. In another aspect, the amount of drug loaded onto the resin comprises about 10%. In another aspect, the amount of drug loaded onto the resin comprises about 0.5% to about 10%.

In another embodiment, the abuse-deterrent composition may optionally comprise one or more antioxidants. Suitable antioxidants comprise tocopherols (e.g., alpha-tocopherol, beta-tocopherol, gamma-tocopherol, or delta-tocopherol), butylated hydroxytoluene (BHT), butylated hydroxyanisole (BHA), citric acid, ascorbic acid, phenolic diterpenes (e.g., carnosic acid, carnosol, rosmanol, epirosmanol, isorosmanol, or methyl carnosate), rosmarinic acid, eugenol, eugenyl acetate, clove bud extract, methanolic extract, tea catechins (e.g., epigallocatechin gallate, epicatechin gallate, epigallocatechin, or epicatechin), or combinations thereof.

In one embodiment described herein, the abuse-deterrent composition may comprise one or more flowability enhancers, one or more release modifiers, one or more active pharmaceutical ingredients, one or more ion exchangers, optionally one or more antioxidants, optionally one or more viscosity modifiers, optionally one or more hydrophilic vehicles, and optionally one or more other pharmaceutically acceptable excipients in a weight percentage amount of the fill mass as further described herein.

In another embodiment, the one or more flowability enhancers comprises from about 35% to about 80% of the fill mass, including all integers within the specified range (Table 1). In one aspect, the one or more flowability enhancers comprises from about 50% to about 80% of the fill mass, including all integers within the specified range. In another aspect, the one or more flowability enhancers comprises from about 50% to about 60% of the fill mass, including all integers within the specified range In another aspect, the one or more flowability enhancers comprises from about 40%, about 45%, about 50%, about 55%, about 60%, about 65%, about 70%, about 75%, or about 80% of the fill mass.

In another embodiment, the one or more release modifiers comprises from about 10% to about 50% of the fill mass, including all integers within the specified range (Table 1). In one aspect, the one or more release modifiers comprises from about 25% to about 50% of the fill mass, including all integers within the specified range. In another aspect, the one or more release modifiers comprises from about 25% to about 40% of the fill mass, including all integers within the specified range. In another aspect, the one or more release modifiers comprises from about 25% to about 35% of the fill mass, including all integers within the specified range. In another aspect, the one or more release modifiers comprises about 20%, about 25%, about 30%, about 35%, about 40%, about 45%, or about 50% of the fill mass.

In another embodiment, the one or more viscosity modifiers may comprise from about 0% to about 10% of the fill mass, including all integers within the specified range (Table 1). In one aspect, the one or more viscosity modifiers may comprise from about 0.5% to about 5% of the fill mass, including all integers within the specified range. In another aspect, the one or more viscosity modifiers may comprise from about 0.5% to about 3% of the fill mass, including all integers within the specified range. In another aspect, the one or more viscosity modifiers may comprise from about 0.5% to about 2% of the fill mass, including all integers within the specified range. In another aspect, the one or more viscosity modifiers may comprise about 0.5%, about 0.75%, about 1%, about 2%, about 3%, about 4%, about 5%, about 6%, about 7%, or about 8%, of the fill mass. In another aspect, fill mass may not have any viscosity modifier.

In another embodiment, one or more antioxidants may comprise from about 0.1% to about 0.5% of the fill mass, including all integers within the specified range. In one aspect, the one or more antioxidants may comprise about 0.3%, 0.4%, or 0.5% of the fill mass.

In another embodiment, the one or more hydrophilic polymers comprises from about 1% to about 50% by weight of the fill mass, including all integers within the specified range. In one aspect, the one or more hydrophilic polymers comprises from about 1% to about 30% of the fill mass, including all integers within the specified range. In another aspect, the one or more hydrophilic polymers comprises from about 25% to about 40% of the fill mass, including all integers within the specified range. In another aspect, the one or more hydrophilic polymers comprises from about 25% to about 35% of the fill mass, including all integers within the specified range. In one aspect, the one or more hydrophilic polymers comprises from about 1% to about 10% of the fill mass, including all integers within the specified range. In another aspect, the one or more hydrophilic polymers comprises about 1%, about 5%, about 10% about, 20%, about 25%, about 30%, about 35%, about 40%, about 45%, or about 50% of the fill mass.

In another embodiment, the one or more API comprises from about 0.1% to about 50% of the fill mass, including all integers within the specified range. In another embodiment, the one or more API comprises from about 1% to about 50% of the fill mass, including all integers within the specified range. In another embodiment, the one or more API comprises from about 1% to about 25% of the fill mass, including all integers within the specified range. In one aspect, the API comprises about 5% of the fill mass. In one aspect, the API comprises about 7% of the fill mass. In one aspect, the API comprises about 10% of the fill mass. In one aspect, the API comprises about 20% of the fill mass. In one aspect, the API comprises about 25% of the fill mass.

In another embodiment, the weight percentage ratio of release modifier to flowability enhancer ranges from about 0.2:1 to about 1:1.5, including all iterations of ratios within the specified range. In one aspect, the weight percentage ratio of release modifier to flowability enhancer ranges from about 0.2:1 to about 0.75:1, including all iterations of ratios within the specified range. In one aspect, the weight percentage ratio of release modifier to flowability enhancer ranges from about 0.2:1 to about 0.5:1, including all iterations of ratios within the specified range. In one aspect, the weight percentage ratio of release modifier to flowability enhancer ranges from about 0.2:1, about 0.3:1, about 0.4:1, about 0.5:1, about 0.6:1, about 0.7:1, about 0.9:1, about 1:1, about 1.1:1, or about 1.2:1.

In another embodiment, the weight percentage ratio of API to the total fill mass ranges from about 1:1000 to about 1:3, including all iterations of ratios within the specified range. In another embodiment, the weight percentage ratio of API to the total fill mass ranges from about 1:100 to about 1:2, including all iterations of ratios within the specified range. In another embodiment, the weight percentage ratio of API to the total fill mass ranges from about 1:15 to about 1:2, including all iterations of ratios within the specified range. In one aspect, the weight percentage ratio of API to the total fill mass is about 1:100. In another aspect, the weight percentage ratio of API to the total is about 1:10. In another aspect, the weight percentage ratio of API to the total fill mass is about 1:7.5. In another aspect, the weight percentage ratio of API to the total fill mass is about 1:5. In another aspect, the weight percentage ratio of API to the total fill mass is about 1:3. In another aspect, the weight percentage ratio of API to the total fill mass is about 1:2.

It was found that the addition of one or more flowability enhancers such as mono- or di-glycerides (e.g., Capmul® MCM), oleic acid, and glyceryl monolinoleate (e.g., Maisine™ 35-1) increases the flowability of the one or more release modifiers (e.g., high molecular weight polyethylene oxide), and thus, provides for a flowable matrix suitable for encapsulation in the soft or hard capsule shells as described herein. For example, using a conventional hydrophilic vehicle, such as polyethylene glycol, it was demonstrated that a carrier comprising polyethylene glycol had a high degree of miscibility with the high molecular weight polyethylene oxide. The resulting mixtures of polyethylene oxide and polyethylene glycol became highly viscous at room temperature, which complicates further processing steps. Further, it was found that certain oils and lipophilic vehicles are not suitable as a flowability enhancer for the one or more release modifiers.

Thus, without being bound by any theory, it is believed that the flowable characteristics of the matrices described herein may be due to the limited miscibility of the one or more release modifiers and the one or more flowability enhancers described herein at room temperature. For example, it was found that mono- or di-glycerides (e.g., Capmul® MCM), oleic acid, or glyceryl monolinoleate (e.g., Maisine™ 35-1) allows adequate matrix flowability at room temperature due to solubilization of high molecular weight polyethylene oxide that allows standard encapsulation techniques to be employed. It was further found that matrix compositions comprising a flowability enhancer with surfactant-like properties, such as for example, mono- or di-glycerides (e.g., Capmul® MCM), oleic acid, or glyceryl monolinoleate (e.g., Maisine™ 35-1) and a high molecular weight polyethylene oxide had a fluid-like consistency at room temperature.

It was further demonstrated that the flowability enhancer and polyethylene oxide became more miscible after being heated to about 70° C. Surprisingly, it was discovered that these matrices having the flowability enhancers, such as mono- or di-glycerides (e.g., Capmul® MCM), oleic acid, or glyceryl monolinoleate (e.g., Maisine™ 35-1) when heated to an elevated temperature of about 70° C. and then cooled to room temperature, became an elastic, rubbery, semi-solid material having an increased Young's modulus. In contrast, it was also unexpectedly demonstrated that this solidifying effect did not occur for compositions having soybean oil as a flowability enhancer. Furthermore, it was surprisingly and advantageously found that the process of heating and cooling the matrices comprising polyethylene oxide and a suitable flow ability enhancer further allow for reduced levels of polyethylene oxide to be used, while exhibiting effective abuse-deterrent and controlled release properties, which has previously been unrealized.

Without being bound by any theory, it is thought that the release modifier is suspended in the flowability enhancer throughout the processing steps. During the annealing steps, the release modifier is believed to become molten. The two components, therefore, become miscible at this point. This appears to be a synergistic effect wherein the flowability enhancer reduces the melting point of the release modifier and also solubilizes the release modifier at the elevated annealing temperature (which is lower than the typical melting point of the release modifier by about 20-50° C.). When cooled, the release modifier and flowability enhancer recrystallizes and forms an elastic semi-solid composition enveloping the API. For example, high molecular weight polyethylene oxide is a semi-crystalline polymer known to melt at about 100° C. In the presence of a suitable flowability enhancer, such as mono- or di-glycerides (e.g., Capmul® MCM), oleic acid, or glyceryl monolinoleate (e.g., Maisine™ 35-1), polyethylene oxide becomes solubilized at about 50° C. to 80° C. After subsequent cooling, the polyethylene oxide and flowability enhancer mixture solidify to form an elastic, rubbery, semi-solid composition. Thus, the composition and annealing process described herein unexpectedly resulted in the formation of an elastic semi-solid composition with advantageous abuse-deterrent properties.

As described herein, the heated pharmaceutical compositions comprising the abuse-deterrent fills are in some embodiments annealed by heating the compositions. In some embodiments, the pharmaceutical compositions comprising a soft or hard capsule shell encapsulating a fill as described herein may be annealed at a temperature of about 70° C. for about 1 hour or less. These annealed elastic semi-solid matrices comprise advantageous abuse-deterrent characteristics.

A common method for extracting abuse prone drugs is by boiling the composition. It was found that the abuse-deterrent fills described herein further provide for abuse deterrence by reducing the percentage of released API released during boiling, suggesting that the matrices described herein maintain a semi-solid elastic material at high temperatures (e.g., in excess of 90-100° C.). Without wishing to be bound by any theory, it is thought that the lipophilic and solubilizing nature of the flowability enhancer in combination with high molecular weight polyethylene oxide provide abuse-deterrent characteristics following an annealing step. The semi-solid elastic characteristics of the abuse-deterrent fills described herein further prevent or reduce the likelihood for the extraction of active pharmaceutical ingredients through the additional means of crushing, grating, grinding, or cutting the dosage forms further described herein.

Another common method for extracting abuse prone drugs is through ethanol based extraction of the composition. It was found that the abuse-deterrent matrices described herein further reduce the extraction of one or more active pharmaceutical ingredients in high percentage ethanol solutions (e.g., 80%), while maintaining desired release rates in gastric-like environments. Thus, the presence of the components of the abuse-deterrent compositions described herein function to inhibit drug release from the pharmaceutical compositions described herein using common attempts of drug extraction. Thus, the compositions described herein have abuse-deterrent properties by preventing the liberation of the active ingredient for injection or insufflation and prevent solvation, dissolution, or extraction of the API by use of aqueous or organic solutions. Furthermore, the compositions also provide controlled release delivery of the API after ingestion by a subject.

In another embodiment, the matrix contains an API useful for the treatment of pain. In one embodiment, the API includes one or more of oxycodone, hydrocodone, oxymorphone, hydromorphone, morphine, codeine, methadone, fentanyl, tapentadol, tramadol, meperidine, propoxyphene, flunitrazepam, barbiturates, amytal, nembutal, seconal, phenobarbital; benzodiazepines, zolpidem, zaleplon, eszopiclone, amphetamines, methylphenidate, salts thereof, or a combination thereof.

In another embodiment, the matrix comprises one or more active pharmaceutical ingredients. In one aspect, the active pharmaceutical ingredient is useful in treating pain. In one aspect, the active pharmaceutical ingredient is oxycodone, hydrocodone, oxymorphone, hydromorphone, tapentadol, morphine, or codeine. In one aspect, the active pharmaceutical ingredient is oxycodone or hydrocodone. In one aspect, the active pharmaceutical ingredient is oxycodone.

In another embodiment, the pharmaceutical compositions disclosed herein includes an opioid, the opioid is selected from buprenorphine, codeine, dextromoramide, dihydrocodone, fentanyl, hydrocodone, hydromorphone, morphine, pentazocine, oxycodeine, oxycodone, oxymorphone, norhydrocodone, noroxycodone, morphine-6-glucuronode, tramadol, tapentadol, or dihydromorphine.

Where an opioid is used as an active drug substance, the opioid may be present in any of its crystalline, polymorphous, semi-crystalline, and amorphous or polyamorphous forms. Furthermore, in another embodiment, an opioid used as an active drug substance may be present in one or more forms selected from its crystalline, polymorphous, semi-crystalline, or amorphous or polyamorphous forms.

Some embodiments of the pharmaceutical compositions disclosed herein include an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts thereof, including oxycodone hydrochloride, hydrocodone bitartrate, hydromorphone hydrochloride or morphine sulphate pentahydrate.

In other embodiments, the pharmaceutical compositions as described herein are suitable for use with water soluble as well as slightly soluble or insoluble active drug substances.

In another embodiment, all of the above mentioned active drug substances may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the pharmaceutical compositions described herein may comprise pharmaceutically acceptable salts of any of the above mentioned active drug substances.

In another embodiment, the API is hydrocodone or oxycodone or a pharmaceutically acceptable salt form of either hydrocodone or oxycodone. Pharmaceutically acceptable salts forms are those formed by contacting hydrocodone or oxycodone free base with a suitable acid in a suitable solvent under suitable conditions that will form a form of hydrocodone or oxycodone acid addition salt. Suitable acids include hydrochloric acid, camphorsulfonic acid, hydrobromic acid, sulfuric acid, methanesulfonic acid, formic acid, acetic acid, oxalic acid, succinic acid, tartaric acid, mandelic acid, malic acid, salicylic acid, fumaric acid, lactic acid, citric acid, glutamic acid, and/or aspartic acid.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, pharmaceutically acceptable opioid salts can comprise sulphate salts, hydrochloride salts, and bitartrate salts.

The concentration of the API in the pharmaceutical composition described herein depends on the specific API substance, the disease to be treated, the condition of the patient, the age, and gender of the patient, etc. The API may be known and a person skilled in the art will be able to find information as to the dosage of each active drug substance and, accordingly, will know how to determine the amount of each active drug substance in the pharmaceutical composition.

The API may be a new chemical entity for which the amount of information is limited. In such cases, the dosage has to be evaluated based on available preclinical and/or clinical data.

In some embodiments described herein, the pharmaceutical composition comprises a dosage form comprising a soft capsule shell or a hard capsule shell comprising a fill that is liquid, semi-solid, or solid. Capsules prepared as described herein can contain a hydrophobic solution, suspension, or lipid or lipophilic vehicle comprising vegetable oils, shortening, or waxes, or combinations thereof. In some aspects described herein, the lipid or lipophilic vehicle may comprise one or more hydrophilic polymers, but as described herein, the vehicle is considered a lipid or lipophilic vehicle. The composition can be formulated to prevent interaction with the capsule shell components and release the pharmaceutical composition at a specified rate.

In one embodiment, the soft capsule shell has the composition of Table 3, including all possible iterations of the specified ranges that provide 100% for the total weight percentage, including or excluding the optional colorings, flavorings, or excipients.

TABLE 3

Exemplary Soft Capsule Composition

| Component | Exemplary Component | Weight Percentage (%) |
|---|---|---|
| Film-forming polymer | Gelatin | 20-45 |
| Plasticizer | Glycerol | 10-30 |
| Solvent | Water | 20-70 |
| Opacifier (optional) | Titanium dioxide | 0.5-1.5 |
| Coloring agent (optional) | Various | 0.05-0.1 |
| TOTAL | | 100% |

Film-former polymers that are useful for creating soft capsules are gelatin, hydroxypropylmethylcellulose (HPMC) or carrageenan (e.g., iota carrageenan and kappa carrageenan).

Plasticizers that are useful for creating soft capsules as described herein are glycerol, sorbitol, polyethylene glycols, or combinations thereof. The weight ratio between the film-forming polymer, plasticizer, and solvent is adjusted so that the gel mass is flowable and not too viscous, and can be made into soft capsules using rotary die encapsulation methods.

In one embodiment described herein, the soft capsule comprises about 43% of at least one film-forming polymer; about 20% of at least one plasticizer; about 36% water; optionally, about 0.7% titanium dioxide; and optionally, about 0.1% of at least one coloring agent.

In one embodiment, the weight percentage range of film-forming polymer of the soft capsule described herein is about 35% to about 45%, including all integers within the specified range. In one aspect, the film-forming polymer weight percentage is about 38%. In another aspect, the film-forming polymer weight percentage is about 42%. In another aspect, the film-forming polymer weight percentage is about 44%.

In one embodiment, the weight percentage range of film-forming polymer of the soft capsule described herein is about 3% to about 15%, including all integers within the specified range. In one aspect, the film-forming polymer weight percentage is about 3%. In one aspect, the film-forming polymer weight percentage is about 5%. In one aspect, the film-forming polymer weight percentage is about 7%. In one aspect, the film-forming polymer weight percentage is about 10%. In one aspect, the film-forming polymer weight percentage is about 12%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

In one aspect, soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing soft capsules comprising the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the soft capsule shell described herein, encapsulates a fill as described herein. In another embodiment described herein, the soft capsule shell and encapsulated fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See Remington's Essentials of Pharmaceutics, Pharmaceutical Press Publishing Company, London, UK, $1^{st}$ Edition, 2013, which is incorporated by reference herein for such teachings.

In another embodiment, the capsule shell is a hard capsule shell. In one aspect, the hard capsule shell may comprise the abuse-deterrent matrices described herein. Any hard capsule shell, for example hard capsule shells comprising gelatin, HPMC, or pullulan, including hard capsule shells exhibiting enteric properties, maybe used with the abuse-deterrent fills described herein. Hard capsule shells are known in the art and are described by Kathpalia et al., *J. Adv. Pharm. Edu. & Res.* 4(2): 165-177 (2014), which is incorporated by reference herein for the specific teachings related to hard capsules.

Another embodiment is a controlled release pharmaceutical composition comprising a capsule shell encapsulating a fill comprising one or more active pharmaceutical ingredients, wherein the capsule shell comprises one or more subcoatings, coatings, or topcoatings. Suitable coatings may be adherence coatings, enteric coatings, moisture barriers, air or gas barriers, polymer coatings, colorings, flavors, writings, or combinations thereof.

Exemplary polymers useful for coatings include cellulose acetate phthalate, hydroxypropylmethyl cellulose phthalate, hydroxypropyl methylcellulose acetate succinate, polyvinyl acetate phthalate, polyvinyl alcohols, cellulose acetate trimellitate, carboxymethylcellulose, methacrylic acid copolymers such as, Eudragit L (polymethacrylic acid, methylmethacrylate, 1:1 ratio), or Eudragit S (polymethacrylic acid, methylmethacrylate, 1:2 ratio), shellac, zein, or combinations thereof.

Suitable plasticizers include acetyl triethyl citrate, dibutyl phthalate, tributyl citrate, triethyl citrate, acetyl tributyl citrate, propylene glycol, triacetin, polyethylene glycol, diethyl phthalate, or combinations thereof.

Suitable solubilizers include sodium lauryl sulfate, sodium lauroyl sarcosinate sodium dodecyl sulfate, polysorbate 20, polysorbate 80, other detergents or surfactants, or combinations thereof.

Anti-adherent agents serve to prevent potential agglomeration in acid media. Suitable anti-adherents include talc, magnesium stearate, calcium stearate, stearic acid, hydrogenated vegetable oils, polyethylene glycols, fumed silica, silicon dioxide, or combinations thereof.

Many conventional coating excipients are described in the art. See e.g., Rowe et al., Eds. *Handbook of Pharmaceutical Excipients*, $7^{th}$ ed. Royal Pharmaceutical Society, UK (2012).

In one embodiment, adjusting the amount of coating and the ratio of polymer to other components allows for tuning the release profile of the dosage form.

Subcoats can be applied to the capsules prior to coating to prevent shell-coat interactions and improve coating adhesion to the capsule. Exemplary subcoatings can comprise polyvinylpyrrolidone, polyvinyl alcohols, hydroxypropyl methylcellulose, polyethylene glycol, oils, or combinations thereof.

Coatings, top coatings, or subcoatings are applied to the exterior of a capsules using various methods known in the art. The coatings are typically prepared as suspensions and sprayed on capsules in perforated coating pans through one or more spray nozzles at a specific temperature. Coating solutions or dispersion may be applied at spray rates between 100 and 400 g/min. The spray rate may be proportionately higher for coatings with higher solid content and lower for more dilute dispersions. In one embodiment, capsules are coated using a pan coater. After the coating suspension is applied, the coated capsules are dried in the pan coater for a specific period of time at a specific temperature.

Another embodiment described herein comprises a subcoating that is applied prior to applying a coating. In one embodiment, the subcoating comprises hydroxypropyl methylcellulose, methylcellulose, ethylcellulose, or a combination thereof.

Another embodiment described herein comprises a coating that is applied directly on the exterior of the capsule. In one embodiment, the coating comprises polyvinyl alcohol, polyvinyl acetate hydroxypropyl methylcellulose, methylcellulose, ethylcellulose, or a combination thereof.

Another embodiment described herein comprises a moisture barrier that is applied as a coating. The moisture barrier can be applied directly to the capsule or on top of a subcoating. In one embodiment the moisture barrier comprises one or more polyvinyl alcohols and appropriate pharmaceutically acceptable excipients. In one embodiment the moisture barrier comprises polyvinyl alcohol, sodium lauryl sulfate, glyceryl mono-caprylate-caprate, and talc. In one aspect, the moisture barrier aids in preserving the cosmetic appearance of the dosage forms by preventing dimpling, sticking, or other processing or storage induced blemishes. In one embodiment, the polyvinyl alcohol coating comprises Opadry® amb II, (Colorcon).

Without being bound by any theory, it is believed that a coating such as polyvinyl alcohol applied to achieve about 10% to about 15% weight gain of the dosage form permits the dosage form to be annealed at a temperature of about 60° C. to about 75° C. for about 10 min to about 90 min and slowly cooled to room temperature without causing cosmetic defects such as dimpling, flattening, sticking, or other defects. It is believed that the coating protects the soft gelatin capsule and prevents it from becoming molten or tacky during the annealing and cooling steps.

In one embodiment, a coating is applied to the capsule dosage form to achieve about a 10% to about 15% weight gain to the dosage form. In one aspect, the weight gain is about 10% to about 20%, including each integer within the specified range. In one aspect, the weight gain is about 8%, about 9%, about 10%, about 11%, about 12%, about 13%, about 14%, about 15%, about 16%, about 17%, about 18%, about 19%, or about 20%. In another embodiment, a first coating is applied to achieve about a 10% weight gain. In another embodiment, a second coating comprising one or more coloring agents is applied to the first coated dosage form to achieve about a 5% weight gain, for a total coating weight gain of about 12% to about 15%.

The pharmaceutical composition described herein can comprise a soft or hard capsule comprising a fill that is liquid, semi-solid, or solid. Capsules prepared as described herein can contain a hydrophobic solution, suspension, or lipid or lipophilic vehicle comprising vegetable oils, shortening, or waxes, or combinations thereof. In some aspects described herein, the lipid or lipophilic vehicle may comprise one or more hydrophilic polymers, but as described herein, the vehicle is considered a lipid or lipophilic vehicle. The composition can be formulated to prevent interaction with the capsule shell components and release the pharmaceutical composition at a specified rate.

Additional pharmaceutical excipients useful for the pharmaceutical composition as described herein include, for example, the following: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); alkalizing agents (ammonia solution, ammonium carbonate, diethanolamine, diisopropanolamine, potassium hydroxide, sodium bicarbonate, sodium borate, sodium carbonate, sodium hydroxide, trolamine); antifoaming agents (dimethicone, simethicone); antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); chelating agents (edetate disodium, ethylenediaminetetraacetic acid and salts, edetic acid); coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl alcohol, polyvinyl acetate phthalate, shellac, sucrose, titanium dioxide, carnauba wax, microcrystalline wax, zein); colorants (caramel, red, yellow, black or blends, ferric oxide); complexing agents (ethylenediaminetetraacetic acid and salts (EDTA), edetic acid, gentisic acid ethanolamide, oxyquinoline sulfate); desiccants (calcium chloride, calcium sulfate, silicon dioxide); emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); filtering aids (powdered cellulose, purified siliceous earth); flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); humectants (glycerol, hexylene glycol, sorbitol); plasticizers (e.g., castor oil, diacetylated monoglycerides, diethyl phthalate, glycerol, mono- and di-acetylated monoglycerides, propylene glycol, triacetin, triethyl citrate); polymers (e.g., cellulose acetate, alkyl celluloses, hydroxyalkyl, acrylic polymers and copolymers); solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); Sorbents (powdered cellulose, charcoal, purified siliceous earth); carbon dioxide sorbents (barium hydroxide lime, soda lime); stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); tonicity agent (dextrose, glycerol, mannitol, potassium chloride, sodium chloride); vehicle: flavored and/or sweetened (aromatic elixir, compound benzaldehyde elixir, iso-alcoholic elixir, peppermint water, sorbitol solution, syrup, tolu balsam syrup); vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); vehicle: solid carrier (sugar spheres); vehicle: sterile (bacteriostatic water for injection, bacteriostatic sodium chloride injection); viscosity-increasing (see suspending agent); water repelling agent (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein.

One embodiment described herein, is a pharmaceutical composition comprising any of the formulations shown in the Tables or Examples described herein. Any of the components of the formulations shown in the Tables or Examples can be increased, decreased, combined, recombined, switched, or removed to provide for a formulation comprising about 100% by weight.

Another embodiment described herein is a method for preparing abuse-deterrent pharmaceutical compositions comprising the abuse-deterrent controlled release matrix described herein comprising (a) mixing one or more optional viscosity modifiers, one or more release modifiers, and one or more antioxidants in one or more flowability enhancers to form a first mixture; (b) adding one or more API to the first mixture, and one or more ion exchangers to form a matrix fill mixture, wherein a portion of one or more API is in a free form and a portion of one or more API is bound to the one or more ion exchanger; (c) filling the matrix fill mixture into capsule shells using standard rotary die encapsulation techniques; and (d) annealing the capsules at an elevated temperature for a period of time. In one aspect, the flowability enhancer is heated to a first elevated temperature prior to mixing the viscosity modifier and/or release modifiers. In another aspect, the flowability enhancer or mixture comprising the flowability enhancer is cooled to a second temperature. In another aspect, the flowability enhancer or mixture comprising the flowability enhancer is cooled to a third temperature. In another aspect, the one or more viscosity modifiers are added to the heated flowability enhancer before adding the one or more release modifiers. In another aspect, the heated mixture is cooled to a second elevated temperature prior to adding the API and the one or more release modifiers. In another aspect, the API is added prior to adding the one or more release modifiers. In another aspect, one or more antioxidants are added prior to adding the one or more release modifiers. In another aspect, a first viscosity modifier is added to the flowability enhancer at a first temperature, followed by cooling the mixture to a second temperature and adding one or more antioxidants to the mixture, and cooling the mixture to a third temperature and adding the API and release modifier.

In another embodiment, the method for preparing the abuse-deterrent pharmaceutical compositions described herein comprise (a) heating one or more flowability enhancers to a first temperature; (b) adding one or more antioxidants and mixing; (c) adding one or more release modifiers to the mixture of b; (d) cooling the mixture to a second temperature; (e) adding one or more API, and one or more ion exchangers to the cooled mixture of step d, wherein a portion of one or more API is in a free form and a portion of one or more API is bound to the one or more ion exchanger; (f) deaerating the mixture of step e; (g) filling the deaerated mixture of step f into capsule shells using rotary die encapsulation techniques; (h) annealing the capsules at an elevated temperature for a period of time; and (i) slowly cooling the annealed capsules of h to room temperature in a controlled manner. In one aspect, the elevated annealing temperature of step h is from about 60° C. to about 80° C. and the period of time is from about 30 min to about 120 min. In one aspect, the controlled cooling of step i comprises cooling the capsules at a rate of about 5° C. per about 10 to about 15 min.

In another embodiment, the method for preparing the abuse-deterrent pharmaceutical compositions described herein comprise (a) heating one or more flowability enhancers to a first temperature; (b) adding one or more viscosity modifiers to the heated flowability enhancer and mixing; (c) cooling the mixture of step b to a second temperature; (d) adding one or more antioxidants to the mixture of step c and mixing; (e) cooling the mixture of step d to a third temperature; (f) adding one or more release modifiers, one or more ion exchangers, and one or more API to form a matrix fill mixture, to the cooled mixture of step e and mixing, wherein a portion of one or more API is in a free form and a portion of one or more API is bound to the one or more ion exchanger; (g) filling the matrix fill mixture into capsule shells using standard rotary die encapsulation techniques; (h) annealing the capsules at an elevated temperature for a period of time; and (i) cooling the capsules to room temperature in a controlled manner. In one aspect, the elevated annealing temperature of step h is from about 60° C. to about 80° C. and the period of time is from about 30 min to about 120 min. In one aspect, the controlled cooling comprises cooling the capsules at a rate of about 5° C. per about 10 to about 15 min.

Another embodiment described herein is a method for manufacturing an abuse-deterrent pharmaceutical composition comprising (a) heating one or more flowability enhancers to about 55° C. to about 70° C. under nitrogen; (b) adding one or more antioxidants to the flowability enhancer and mixing at about 50 to about 300 RPM until dissolved; (c) cooling the mixture of step b to about 25° C. to about 35° C. while mixing at about 50 to about 300 RPM; (d) adding one or more API, and one or more ion exchangers, and mixing at about 50 to about 300 RPM for about 30 min, wherein a portion of the one or more API is in a free form and a portion of one or more API is bound to the one or more ion exchanger; (e) adding a viscosity modifier to the mixture of step d and mixing at about 50 to about 300 RPM for about 30 min; (f) deaerating the mixture of step e for at least about 30 min; (g) maintaining the deaerated mixture at a third temperature with continuous mixing at about 50 to about 100 RPM under nitrogen during encapsulation; (h) encapsulating the mixture of step g into soft capsule shells using rotary die encapsulation; (i) drying the capsules; (i) removing processing lubrication with isopropyl alcohol; (j) transferring the capsules to a coating pan operating at about 1-2 RPM at a temperature of about 30° C. to about 35° C.; (k) coating the capsules of step j with a coating composition at about 1-2 RPM until about 10% to about 20% weight gain is achieved; (1) heating the capsules of step k to about 60° C. to about 80° C. for about 30 min to about 90 min at about 1-2 RPM; (m) cooling the capsules of step l to about 30° C. at a rate of about 2° C. to about 10° C. per each about 5 min to about 20 min period while maintaining about 1-2 RPM; (n) cooling the capsules of step m from about 30° C. to room temperature (ca. 25° C.) while maintaining about 1-2 RPM; (o) printing labels on the capsule; and (p) packaging the capsules. In one aspect described herein, the coating and annealing process are conducted in a coating pan.

In one embodiment, the methods for preparing the abuse-deterrent pharmaceutical compositions described herein comprise heating the flowability enhancer or a mixture comprising the flowability enhancer to a first temperature. In one aspect, the first temperature is about 40° C. to about 170° C., including each integer within the specified range. In another aspect, the first temperature is about 120° C. to about 170° C., including each integer within the specified range. In another aspect, the first temperature is about 40° C. to about 90° C., including each integer within the specified range. In another aspect, the first temperature is about 40° C., about 45° C., about 50° C., about 55° C., about 60° C., about 65° C., about 70° C., about 75° C., about 80° C., about 90° C., about 100° C., about 110° C., about 120° C., about 130° C., about 140° C., about 150° C., about 160° C., or about 170° C.

In another embodiment, the methods for preparing the abuse-deterrent pharmaceutical compositions described herein comprise cooling the flowability enhancer or a mixture comprising the flowability enhancer to a second temperature. In one aspect, the second temperature is about 25° C. to about 100° C., including each integer within the specified range. In another aspect, the second temperature is about 25° C. to about 50° C., including each integer within the specified range. In another aspect, the second temperature is about 40° C. to about 90° C., including each integer within the specified range. In another aspect, the second temperature is about 40° C. to about 90° C., including each integer within the specified range. In another aspect, the second temperature is about 25° C., about 30° C., about 35° C., about 40° C., about 45° C., about 50° C., about 55° C., about 60° C., about 65° C., about 70° C., about 75° C., about 80° C., about 90° C., or about 100° C.

In another embodiment, the methods for preparing the abuse-deterrent pharmaceutical compositions described herein comprise cooling the flowability enhancer or a mixture comprising the flowability enhancer to a third temperature. In one aspect, the third temperature is about 25° C. to about 100° C., including each integer within the specified range. In another aspect, the third temperature is about 25° C. to about 50° C., including each integer within the specified range. In another aspect, the third temperature is about 40° C. to about 90° C., including each integer within the specified range. In another aspect, the third temperature is about 40° C. to about 90° C., including each integer within the specified range. In another aspect, the third temperature is about 25° C., about 30° C., about 35° C., about 40° C., about 45° C., about 50° C., about 55° C., about 60° C., about 65° C., about 70° C., about 75° C., about 80° C., about 90° C., or about 100° C.

In another embodiment, the methods for preparing the abuse-deterrent pharmaceutical compositions described herein comprise annealing the pharmaceutical composition comprising a soft or capsule shell and a matrix fill as described herein at specified temperature for a period of time. In one aspect, the temperature ranges from about 45° C. to about 120° C., including each integer within the specified range. In another aspect, the temperature ranges from about 55° C. to about 85° C., including each integer within the specified range. In another aspect, the temperature is about 45° C., about 50° C., about 55° C., about 60° C., about 65° C., about 70° C., about 75° C., about 80° C., about 90° C., about 100° C., about 110° C., or about 120° C. In another aspect, the annealing time ranges from about 10 minutes to about 160 minutes, including each integer within the specified range. In another aspect, the annealing time ranges from about 1 minute to about 80 minutes, including each integer within the specified range. In another aspect, the annealing time ranges from about 40 minutes to about 80 minutes, including each integer within the specified range. In another aspect, the annealing time is about 1 min, about 3 min, about 6 min, about 9 min, about 12 min, about 15 min, about 20 min, about 25 min, about 30 min, about 35 min, about 40 min, about 45 min, about 50 min, about 55 min, about 60 min, about 70 min, about 80 min, about 90 min, about 100 min, about 110 min, about 120 min, about 130 min, about 140 min, about 150 min, or about 160 min.

In another embodiment, the abuse-deterrent pharmaceutical composition described herein provides a dosage of an API described herein for administration to a subject. The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

In one embodiment, the dosage may be administered to a human in need of management of moderate to severe chronic pain and neuropathic pain associated with diabetic peripheral neuropathy (DPN), when a continuous, persistent (around-the-clock) opioid analgesic is needed for an extended period of time.

The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition, including but not limited to, pain.

In one embodiment, the pharmaceutical composition described herein is administered in multiple dosages simultaneously to achieve a desired dose. For example, two or more identical dosages are administered at one time to achieve a desired dose. Two 40 mg dosage forms may be administered simultaneously to provide 80 mg. Likewise, three 40 mg dosage forms or four 30 mg dosage forms may be administered simultaneously to provide 120 mg. In another embodiment, two or more different dosages are administered at one time. Such dual or different simultaneous doses can be used to provide an effective dose of the pharmaceutical composition to a subject in need thereof.

In one embodiment, the abuse-deterrent oral composition described herein, comprises one or more active pharmaceutical ingredients in an amount of about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, or even more.

In another embodiment, the abuse-deterrent oral composition described herein, comprises one or more active pharmaceutical ingredients in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg; about 250 mg to about 500 mg, about 260 mg to about 500 mg, about 270 mg to about 500 mg, about 280 mg to about 500 mg, about 290 mg to about 500 mg, about 300 mg to about 500 mg, about 310 mg to about 500 mg, about 320 mg to about 500 mg, about 330 mg to about 500 mg, about 340 mg to about 500 mg, about 350 mg to about 500 mg, about 360 mg to about 500 mg, about 370 mg to about 500 mg, about 380 mg to about 500 mg, about 390 mg to about 500 mg, about 400 mg to about 500 mg, about 410 mg to about 500 mg, about 420 mg to about 500 mg, about 430 mg to about 500 mg, about 440 mg to about 500 mg, about 450 mg to about 500 mg, about 460 mg to about 500 mg, about 470 mg to about 500 mg, about 480 mg to about 500 mg, or about 490 mg to about 500 mg.

In one embodiment described herein, the abuse-deterrent oral composition described herein may comprise an API load (e.g., a drug load of one or more active pharmaceutical ingredients) of about 1% to about 90%, including each integer within the specified range. In one embodiment, the drug load can comprise about 1%, about 2%, about 2.5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or even higher. In one aspect, the drug load is about 3%. In one aspect, the drug load is about 5%. In one aspect, the drug load is about 6%. In one aspect, the drug load is about 9%. In one aspect, the drug load is about 10%. In one aspect, the drug load is about 12%. In one aspect, the drug load is about 15%. In one aspect, the drug load is about 20%. In one aspect, the drug load is about 25%. In one aspect, the drug load is about 30%. In one aspect, the drug load is about 35%. In one aspect, the drug load is about 40%. In one aspect, the drug load is about 50%. In one aspect, the drug load is about 60%. In one aspect, the drug load is about 28%. In one aspect, the drug load is about 32%. In one aspect, the drug load is about 44%. In one embodiment, the drug load is about 48%.

In one embodiment described herein, the pharmaceutical composition comprises an API in complex with one or more ion exchangers, wherein the ion exchangers comprise a predetermined binding capacity of ionic groups of the ion exchanger to which the API is bound. It is preferred that the ion exchanger has a binding capacity of at least about 25%, more preferably about 50% or higher. Binding capacity is measured for the API is the amount of the API that is removed from a suitably concentrated solution of the API.

In one aspect, about 1% to about 99% of the binding capacity of the ion exchanger comprises one or more API. In one aspect, at least about 1% of the binding capacity of the ion exchanger comprises one or more API. In one aspect, at least about 5% of the binding capacity of the ion exchanger comprises one or more API. In one aspect, at least about 10% of the binding capacity of the ion exchanger comprises one or more API. In one aspect, at least about 15% of the binding capacity of the ion exchanger comprises one or more API. In one aspect, at least about 20% of the binding capacity of the ion exchanger comprises one or more API. In one aspect, at least about 25% of the binding capacity of the ion exchanger comprises one or more API. In one aspect, at least about 30% of the binding capacity of the ion exchanger comprises one or more API. In one aspect, at least about 35% of the binding capacity of the ion exchanger comprises one or more API. In one aspect, at least about 40% of the binding capacity of the ion exchanger comprises one or more API. In one aspect, at least about 45% of the binding capacity of the ion exchanger comprises one or more API. In one aspect, at least about 50% of the binding capacity of the ion exchanger comprises one or more API. In one aspect, at least about 55% of the binding capacity of the ion exchanger comprises one or more API. In one aspect, at least about 60% of the binding capacity of the ion exchanger comprises one or more API. In one aspect, at least about 65% of the binding capacity of the ion exchanger comprises one or more API. In one aspect, at least about 70% of the binding capacity of the ion exchanger comprises one or more API. In one aspect, at least about 75% of the binding capacity of the ion exchanger comprises one or more API. In one aspect, at least about 80% of the binding capacity of the ion exchanger comprises one or more API. In one aspect, at least about 85% of the binding capacity of the ion exchanger comprises one or more API. In one aspect, at least about 90% of the binding capacity of the ion exchanger comprises one or more API. In one aspect, at least about 95% of the binding capacity of the ion exchanger comprises one or more API. In one aspect, at least about 99% of the binding capacity of the ion exchanger comprises one or more API. In one aspect, at least about 100% of the binding capacity of the ion exchanger comprises one or more API.

In one embodiment, a portion of one or more API is in the free form and another portion is bound to the ion exchanger. In another embodiment, about 0.1% by mass of one or more API is in the free form and 99.9% by mass of one or more API is in the bound form. In one aspect, about 0.1% to about 99% by mass of one or more API is in the free form and 0.1% to about 99% by mass of one or more API is in the bound form. In one aspect, about 0.1% by mass of one or more API is in the free form and 99.9% by mass of one or more API is in the bound form. In one aspect, about 1% by mass of one or more API is in the free form and 99% by mass of one or more API is in the bound form. In one aspect, about 5% by mass of one or more API is in the free form and 95% by mass of one or more API is in the bound form. In one aspect, about 10% by mass of one or more API is in the free form and 90% by mass of one or more API is in the bound form. In one aspect, about 15% by mass of the API is in the free form and 85% by mass of one or more API is in the bound form. In one aspect, about 20% by mass of one or more API is in the free form and 80% by mass of the API is in the bound form. In one aspect, about 25% by mass of one or more API is in the free form and 75% by mass of one or more API is in the bound form. In one aspect, about 30% by mass of one or more API is in the free form and 70% by mass of one or more API is in the bound form. In one aspect, about 35% by mass of one or more API is in the free form and 65% by mass of one or more API is in the bound form. In one aspect, about 40% by mass of one or more API is in the free form and 60% by mass of one or more API is in the bound form. In one aspect, about 45% by mass of one or more API is in the free form and 55% by mass of one or more API is in the bound form. In one aspect, about 50% by mass of one or more API is in the free form and 50% by mass of one or more API is in the bound form. In one aspect, about 55% by mass of one or more API is in the free form and 45% by mass of one or more API is in the bound form. In one aspect, about 60% by mass of one or more API is in the free form and 40% by mass of one or more API is in the bound form. In one aspect, about 65% by mass of one or more API is in the free form and 35% by mass of one or more API is in the bound form. In one aspect, about 70% by mass of one or more API is in the free form and 30% by mass of one or more API is in the bound form. In one aspect, about 75% by mass of one or more API is in the free form and 25% by mass of one or more API is in the bound form. In one aspect, about 80% by mass of one or more API is in the free form and 20% by mass of one or more API is in the bound form. In one aspect, about 85% by mass of one or more API is in the free form and 15% by mass of one or more API is in the bound form. In one aspect, about 90% by mass of one or more API is in the free form and 10% by mass of one or more API is in the bound form. In one aspect, about 95% by mass of one or more API is in the free form and 5% by mass of one or more API is in the bound form. In one aspect, about 90% by mass of one or more API is in the free form and 10% by mass of one or more API is in the bound form. In one aspect, about 95% by mass of one or more API is in the free form and 5% by mass of one or more API is in the bound form. In one aspect, about 99% by mass of one or more API is in the free form and 1% by mass of one or more API is in the bound form.

In one embodiment, the API is oxycodone, hydrocodone or codeine, or a salt, ether, ester, variant, or derivative thereof. In one embodiment, the API is oxycodone. In one embodiment, the API is oxycodone hydrochloride. In another embodiment, the API is hydrocodone. See Prescribing Information for OxyContin® ER 04/2014 (Purdue Pharma LP; available at www.purduepharma.com) and Zohydro® ER 01/2015 (Zogenix® Inc.; available at: www.zogenix.com), which are incorporated by reference herein for such teachings.

In another embodiment, the API may comprise oxycodone, hydrocodone, or codeine and an additional API. In one aspect, the additional API prevents opioid abuse when an excess of opioid is used. In another aspect, the additional API reduces or prevents opioid induced side effects.

In one embodiment, the API comprises oxycodone hydrochoride. The oxycodone may comprise trace amounts of impurities from the manufacturing process. In one embodiment described herein, the oxycodone hydrochloride comprises greater than 25 ppm of 14-hydroxycodeinone, but less than 100 ppm. In another embodiment the oxycodone hydrochloride comprises about 50 ppm of 14-hydroxycodeinone. In another embodiment the oxycodone hydrochloride comprises about 90 ppm of 14-hydroxycodeinone. In another embodiment the oxycodone hydrochloride comprises <100 ppm of 14-hydroxycodeinone.

In one embodiment, the abuse-deterrent oral composition described herein comprises a dose of opioid analgesic. In one aspect, the dose of opioid analgesic is about 5 mg. In one aspect, the dose of opioid analgesic is about 10 mg. In one aspect, the dose of opioid analgesic is about 20 mg. In another aspect, the dose of opioid analgesic is about 30 mg. In another aspect, the dose of opioid analgesic is about 40 mg. In another aspect, the dose of opioid analgesic is about 50 mg. In another aspect, the dose of opioid analgesic is about 60 mg. In another aspect, the dose of opioid analgesic is about 70 mg. In another aspect, the dose of opioid analgesic is about 80 mg. In another aspect, the dose of opioid analgesic is about 90 mg. In another aspect, the dose of opioid analgesic is about 100 mg. In another aspect, the dose of opioid analgesic is about 120 mg. In another aspect, the dose of opioid analgesic is about 140 mg. In another aspect, the dose of opioid analgesic is about 160 mg. In another aspect, the dose of opioid analgesic is about 180 mg. In another aspect, the dose of opioid analgesic is about 200 mg.

In one embodiment, the abuse-deterrent oral composition described herein comprises a dose of oxycodone. In one aspect, the dose of oxycodone is about 5 mg. In one aspect, the dose of oxycodone is about 10 mg. In another aspect, the dose of oxycodone is about 15 mg. In another aspect, the dose of oxycodone is about 20 mg. In another aspect, the dose of oxycodone is about 30 mg. In another aspect, the dose of oxycodone is about 40 mg. In another aspect, the dose of oxycodone is about 50 mg. In another aspect, the dose of oxycodone is about 60 mg. In another aspect, the dose of oxycodone is about 70 mg. In another aspect, the dose of oxycodone is about 80 mg. In another aspect, the dose of oxycodone is about 100 mg. In another aspect, the dose of oxycodone is about 120 mg. In another aspect, the dose of oxycodone is about 140 mg. In another aspect, the dose of oxycodone is about 160 mg. In another aspect, the dose of oxycodone is about 180 mg. In another aspect, the dose of oxycodone is about 200 mg.

In another embodiment, the total dosage of oxycodone administered in a 24-hour period is about 20 mg to about 600 mg per 24-hour period. In one aspect, the total dosage of oxycodone or hydrocodone administered in a 24-hour period is about 50 mg to about 250 mg per 24-hour period. The dosage can contain a total amount of oxycodone effective for treatment, amelioration, prophylaxis, or reducing the onset of or symptoms of pain.

In one embodiment, the recommended dosage is based upon the condition of the subject in need thereof. The subject can comprise a human or mammal in need thereof. In one aspect, the need is defined as a painful condition or perception of pain. In one embodiment, the perception of pain is described as a numerical scale. In one aspect, this numerical scale indicates 0 for no pain, 1-3 suggestive of mild pain; annoying or nagging pain that does not affect the activities of daily life, 4-6 for moderate pain that interferes significantly with the activities of daily life, and 7-10 for severe pain that is disabling for which the activities of daily life are not possible. Another aspect described herein comprises orally administering a maximal dosage of about 10 mg to about 120 mg of oxycodone every 24 hours for humans or mammals with a pain of 1-3. Another aspect described herein comprises orally administering a maximal dosage of about 80 mg to about 400 mg of oxycodone every 24 hours for humans or mammals with a pain of 4-6. Another aspect described herein comprises orally administering a maximal dosage of 120 mg to about 600 mg of oxycodone every 24 hours for humans or mammals with a pain of 7-10. In one aspect, the level of pain is assessed by observing the human or mammal.

Another aspect described herein comprises orally administering a delayed release dosage of about 10 mg of oxycodone every 12 hours for a human or mammal with a pain of 1-3. Another aspect described herein comprises orally administering a delayed release dosage of about 30 mg of oxycodone 1 every 12 hours for a human or mammal with a pain of 4-6. Another aspect described herein comprises orally administering a delayed release dosage of about 80 mg of oxycodone every 12 hours for a human or mammal with a pain of 7-10. Another aspect described herein comprises increasing the delayed release dosage of oxycodone by 10 mg increments every 24 hours to a maximal daily dosage of 600 mg if pain of any type is not ameliorated in the human or mammal in need thereof. Another aspect described herein comprises decreasing the dosage of oxycodone as needed every 24 hours if pain of any type has decreased or has been ameliorated in the human or mammal in need thereof.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of opioid analgesic is 10 mg to about 40 mg. In one aspect, an initial dose of about 10 mg to about 40 mg is suitable for a subject that not tolerant of an opioid. In one aspect, the initial dose is about 10 mg of opioid analgesic. In another aspect, the initial dose is about 20 mg of opioid analgesic. In another aspect, the initial dose is about 30 mg of opioid analgesic. In another aspect, the initial dose is about 40 mg of opioid analgesic. In another aspect, the dose of opioid analgesic may be maintained and given every 8 to 12 hours. In another aspect, the dose of opioid analgesic may be increased by about 10 mg to about 20 mg every 8 hrs to 12 hrs until pain relief occurs.

In another embodiment, the initial dosage of opioid analgesic is 40 mg to about 80 mg. In one aspect, an initial dose of about 40 mg to about 80 mg is suitable for a subject that has an opioid tolerant phenotype. In one aspect, the initial dose is about 40 mg of opioid analgesic. In another aspect, the initial dose is about 50 mg of opioid analgesic. In another aspect, the initial dose is about 60 mg of opioid analgesic. In another aspect, the initial dose is about 70 mg of opioid analgesic. In another aspect, the initial dose is about 80 mg of opioid analgesic. In another aspect, the dose of opioid analgesic may be maintained and given every 8 to 12 hours. In another aspect, the dose of opioid analgesic may be increased by about 10 mg to about 20 mg every 8 hrs to 12 hrs until pain relief occurs.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of oxycodone is 10 mg to about 40 mg. In one aspect, an initial dose of about 10 mg to about 40 mg is suitable for a subject that not tolerant of an opioid and a dose. In one aspect, the initial dose is about 10 mg of oxycodone. In another aspect, the initial dose is about 20 mg of oxycodone. In another aspect, the initial dose is about 20 mg of oxycodone. In another aspect, the initial dose is about 30 mg of oxycodone. In another aspect, the initial dose is about 40 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until pain relief occurs.

In another embodiment, the initial dosage of oxycodone is 40 mg to about 160 mg. In one aspect, an initial dose of about 40 mg to about 80 mg is suitable for a subject that has an opioid tolerant phenotype. In one aspect, the initial dose is about 40 mg of oxycodone. In another aspect, the initial dose is about 50 mg of oxycodone. In another aspect, the initial dose is about 60 mg of oxycodone. In another aspect, the initial dose is about 70 mg of oxycodone. In another aspect, the initial dose is about 80 mg of oxycodone. In another aspect, the initial dose is about 100 mg of oxycodone. In another aspect, the initial dose is about 120 mg of oxycodone. In another aspect, the initial dose is about 140 mg of oxycodone. In another aspect, the initial dose is about 160 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until pain relief occurs.

Additionally, the abuse-deterrent pharmaceutical compositions described herein may be useful for the treatment of pain stemming from, including but not limited to, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, trauma, or granuloma annulare.

Another embodiment described herein is an abuse-deterrent pharmaceutical composition as described herein for administration to a subject having pain, comprising a therapeutically effective amount of one or more active pharmaceutical ingredients, wherein the subject achieves a reduction of pain relative to baseline without substantially experiencing one or more side effects including, but not limited to, headache, vertigo, somnolence, nausea, constipation, vomiting, xerostomia, fatigue, pruritus, eructation, heartburn, abdominal discomfort, or loss of appetite.

Another embodiment described herein is an abuse-deterrent pharmaceutical composition as described herein for administration to a subject having pain, comprising a therapeutically effective amount of one or more active pharmaceutical ingredients exhibiting an in vitro dissolution rate at pH 1.2 comprising about 35% to about 95% dissolution after about 60 minutes to about 480 minutes including each integer within the specified ranges of dissolution and time. In one aspect, the in vitro dissolution rate at pH 1.2 is about 35% after about 60 min, about 50% after about 120 min, about 70% after about 240 min, about 85% after about 480 min.

Another embodiment described herein is an abuse-deterrent pharmaceutical composition as described herein for administration to a subject having pain, comprising a therapeutically effective amount of one or more active pharmaceutical ingredients exhibiting an in vitro dissolution rate at pH 1.2 comprising about 15% to about 95% dissolution after about 60 minutes to about 480 minutes including each integer within the specified ranges of dissolution and time. In one aspect, the in vitro dissolution rate at pH 1.2 is about 10% after about 60 min, about 20% after about 90 minutes, about 50% after about 120 min, about 70% after about 240 min, about 85% after about 480 min.

In another embodiment, the abuse-deterrent pharmaceutical composition comprising an abuse-deterrent matrix as described herein reduces the dissolution and extraction of an API. Suitable non-limiting examples of extraction methods comprise incubating the abuse-deterrent pharmaceutical composition in boiling conditions, in aqueous solutions of alcohol, and in distilled water. These methods may be used in conjunction with additional means of agitating, for example, with paddles, dipping, vigorous shaking, physical manipulations, and the like.

In another embodiment, the abuse-deterrent pharmaceutical composition as described herein has an in vitro dissolution rate under boiling conditions in an aqueous media (e.g., a temperature of about 90° C. to about 120° C.) is less than about 35% to about 60% after about 10 minutes to about 45 minutes, including each integer within the specified ranges of dissolution and time. In one aspect, the in vitro dissolution rate of the controlled release pharmaceutical composition under boiling conditions in an aqueous media is less than about 50% after about 5 minutes. In another aspect, the in vitro dissolution rate of the controlled release pharmaceutical composition under boiling conditions in an aqueous media is less than about 50% after about 10 minutes. In another aspect, the in vitro dissolution rate of the controlled release pharmaceutical composition under boiling conditions in an aqueous media is less than about 50% after about 20 minutes. In another aspect, the in vitro dissolution rate of the controlled release pharmaceutical composition under boiling conditions in an aqueous media is less than about 50% after about 30 minutes. In another aspect, the in vitro dissolution rate of the controlled release pharmaceutical composition under boiling conditions in an aqueous media is less than about 60% after about 45 minutes.

In another embodiment, the abuse-deterrent controlled release pharmaceutical composition as described herein has an in vitro dissolution rate in an aqueous alcohol solution (e.g., an aqueous solution of ethanol of 80%) of less than about 20% to about 50% after about 30 minutes to about 360 minutes, including each integer within the specified ranges of dissolution and time. In one aspect, the in vitro dissolution rate of the controlled release pharmaceutical composition in an aqueous alcohol solution is less than about 10% after about 30 minutes. In another aspect, the in vitro dissolution rate of the controlled release pharmaceutical composition in an aqueous alcohol solution is less than about 20% after about 60 minutes. In another aspect, the in vitro dissolution rate of the controlled release pharmaceutical composition in an aqueous alcohol solution is less than about 50% after about 60 minutes. In another aspect, the in vitro dissolution rate of the controlled release pharmaceutical composition in an aqueous alcohol solution is less than about 50% after about 120 minutes. In another aspect, the in vitro dissolution rate of the controlled release pharmaceutical composition in an aqueous alcohol solution is less than about 50% after about 180 minutes. In another aspect, the in vitro dissolution rate of the controlled release pharmaceutical composition in an aqueous alcohol solution is less than about 50% after about 360 minutes.

Another embodiment described herein is an abuse-deterrent pharmaceutical composition as described herein comprising a therapeutically effective amount of one or more active pharmaceutical ingredients for administration to a subject having pain, exhibiting an in vitro dissolution rate at pH 1.2 of about 35% to about 95% after about 60 minutes to about 480 minutes, an in vitro dissolution rate under boiling conditions less than about 35% to about 60% after about 10 minutes to about 45 minutes, and an in vitro dissolution rate in an aqueous alcohol solution of less than about 20% to about 50% after about 30 minutes to about 360 minutes.

Figure 2:
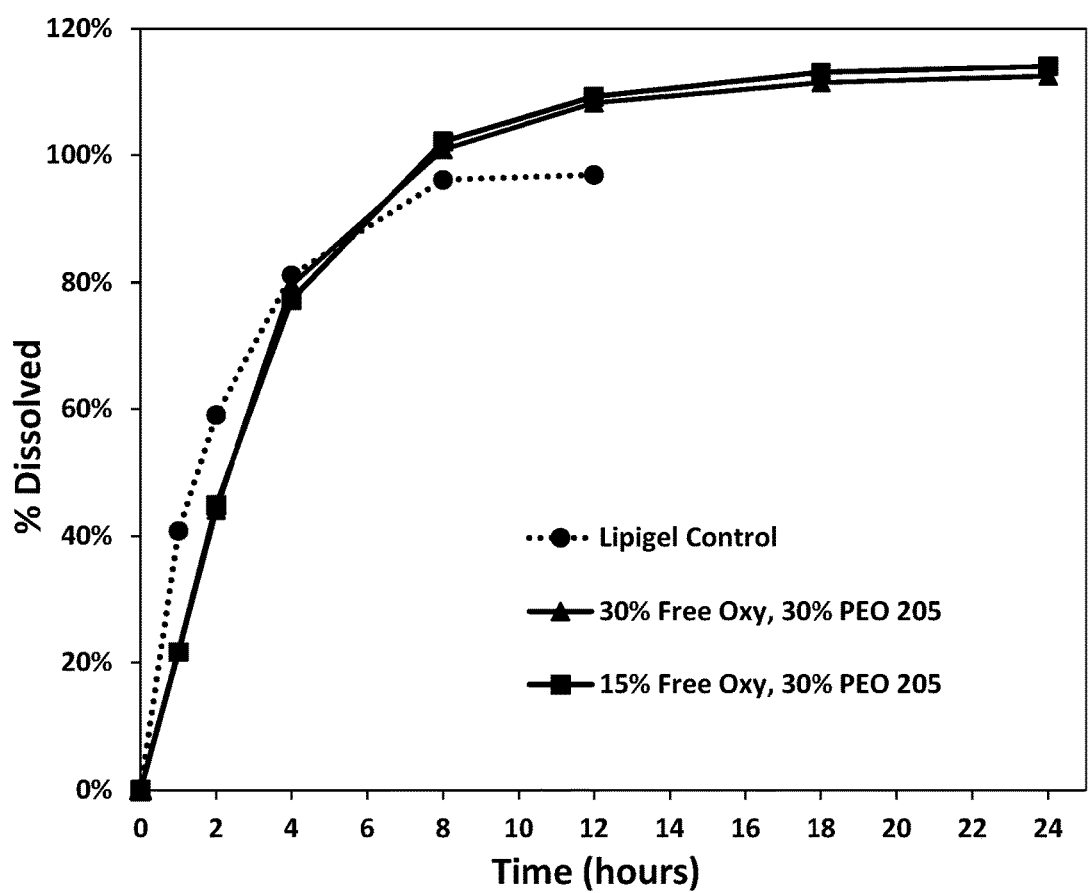
FIG. 2. Percent release of oxycodone from test abuse deterrent pharmaceutical compositions Formulation 5 and Formulation 6, having differing amounts of free oxycodone are compared to the percent release of oxycodone from a reference abuse deterrent pharmaceutical composition.
Figure 3:
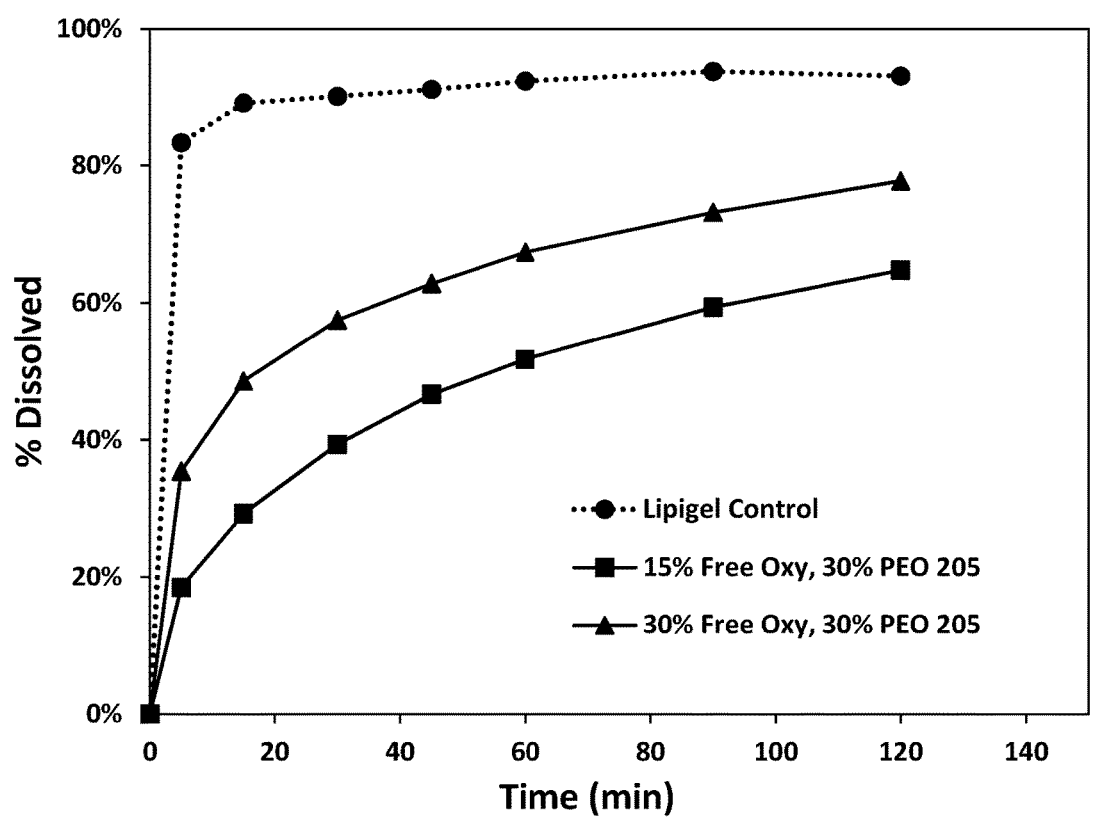
FIG. 3. Percent release of oxycodone from physically manipulated (ground with a coffee grinder) annealed test abuse deterrent pharmaceutical compositions, Formulation 5 and Formulation 6 are compared to a reference abuse deterrent pharmaceutical composition.

Another embodiment described herein is an abuse-deterrent pharmaceutical composition as described herein comprising a therapeutically effective amount of one or more active pharmaceutical ingredients for administration to a subject having pain, exhibiting an in vitro dissolution rate as described herein in any one of FIGS. 1-3.

Another embodiment described herein is a method for orally administering a dosage form of an abuse-deterrent pharmaceutical composition comprising an API described herein for the treatment, amelioration, prophylaxis, or reducing the onset of or symptoms of pain.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, wherein the pharmaceutical composition exhibits an in vitro dissolution rate at pH 1.2, of about 35% to about 95% after about 60 minutes to about 480 minutes, an in vitro dissolution rate under boiling conditions less than about 35% to about 60% after about 10 minutes to about 45 minutes, and an in vitro dissolution rate in an aqueous alcohol solution of less than about 20% to about 50% after about 30 minutes to about 360 minutes.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, exhibiting an in vitro dissolution rate as described herein or shown in any one of FIG. 1-3.

Another embodiment described herein is a method for treating an individual having pain, with a pharmaceutical composition described herein comprising an abuse-deterrent matrix described herein comprising a dosage of about 10 mg of oxycodone to about 80 mg of oxycodone, wherein subjects administered a single dosage exhibit a mean plasma oxycodone $C_{max}$ of about 10 ng/mL to about 150 ng/mL, including each integer within the specified range. In one aspect, the composition is provided in a dosage form containing a total amount of about 10 mg of oxycodone, wherein subjects administered a single dosage exhibit a mean plasma oxycodone $C_{max}$ of about 10 ng/mL. In another aspect, the composition is provided in a dosage form containing a total amount of about 20 mg of oxycodone, wherein subjects administered a single dosage exhibit a mean plasma oxycodone $C_{max}$ of about 20 ng/mL. In another aspect, the composition is provided in a dosage form containing a total amount of about 40 mg of oxycodone, wherein subjects administered a single dosage exhibit a mean plasma oxycodone $C_{max}$ of about 40 ng/mL. In another aspect, the composition is provided in a dosage form containing a total amount of about 80 mg of oxycodone, wherein subjects administered a single dosage exhibit a mean plasma oxycodone $C_{max}$ of about 100 ng/mL.

Another embodiment described herein is a method for treating an individual having pain, with a pharmaceutical composition described herein comprising an abuse-deterrent matrix described herein comprising a dosage of about 10 mg of oxycodone to about 80 mg of oxycodone, wherein subjects administered a single dosage exhibit a mean plasma oxycodone $AUC_{0\to\infty}$ of about 100 h·mg/L to about 1000 h·mg/L, including each integer within the specified range. In one aspect, the composition is provided in a dosage form containing a total amount of about 10 mg of an oxycodone, wherein subjects administered a single dosage exhibit a mean plasma oxycodone $AUC_{0\to\infty}$ of about 100 h·mg/L. In another aspect, the composition is provided in a dosage form containing a total amount of about 20 mg of oxycodone, wherein subjects administered a single dosage exhibit a mean plasma oxycodone $AUC_{0\to\infty}$ of about 200 h·mg/L. In another aspect, the composition is provided in a dosage form containing a total amount of about 40 mg of oxycodone, wherein subjects administered a single dosage exhibit a mean plasma oxycodone $AUGC_{0\to\infty}$ of about 400 h·mg/L. In another aspect, the composition is provided in a dosage form containing a total amount of about 80 mg of oxycodone, wherein subjects administered a single dosage exhibit a mean plasma oxycodone $AUC_{0\to\infty}$ of about 1000 h·mg/L.

Another embodiment described herein is a method for treating an individual having pain, with a pharmaceutical composition described herein comprising an abuse-deterrent matrix described herein comprising a dosage of about 10 mg of oxycodone to about 80 mg of oxycodone, wherein subjects administered a single dosage exhibits a $T_{max}$ of about 1 hr to about 8 hrs, including each integer within the specified range. In one aspect, the composition is provided in a dosage form containing a total amount of about 10 mg to about 80 mg of oxycodone, wherein subjects administered a single dosage exhibit a $T_{max}$ of about 1 hr, about 1.5 hrs, about 2 hrs, about 2.5 hrs, about 3 hrs, about 3.5 hrs, about 4 hrs, 4.5 hrs, 5 hrs, 5.5 hrs, 6 hrs, 6.5 hrs, 7 hrs, 7.5 hrs, or about 8 hrs.

Another embodiment described herein is a method for treating an individual having pain, with a pharmaceutical composition described herein comprising an abuse-deterrent matrix described herein comprising a dosage of about 10 mg of opioid analgesic to about 80 mg of opioid analgesic, wherein subjects administered a single dosage exhibit a mean plasma opioid analgesic $C_{max}$ of about 10 ng/mL to about 120 ng/mL, including each integer within the specified range. In one aspect, the composition is provided in a dosage form containing a total amount of about 10 mg of an opioid analgesic, wherein subjects administered a single dosage exhibit a mean plasma opioid analgesic $C_{max}$ of about 20 ng/mL. In another aspect, the composition is provided in a dosage form containing a total amount of about 20 mg of opioid analgesic, wherein subjects administered a single dosage exhibit a mean plasma opioid analgesic $C_{max}$ of about 30 ng/mL. In another aspect, the composition is provided in a dosage form containing a total amount of about 30 mg of opioid analgesic, wherein subjects administered a single dosage exhibit a mean plasma opioid analgesic $C_{max}$ of about 40 ng/mL. In another aspect, the composition is provided in a dosage form containing a total amount of about 40 mg of opioid analgesic, wherein subjects administered a single dosage exhibit a mean plasma opioid analgesic $C_{max}$ of about 60 ng/mL. In another aspect, the composition is provided in a dosage form containing a total amount of about 80 mg of opioid analgesic, wherein subjects administered a single dosage exhibit a mean plasma opioid analgesic $C_{max}$ of about 120 ng/mL.

Another embodiment described herein is a method for treating an individual having pain, with a pharmaceutical composition described herein comprising an abuse-deterrent matrix described herein comprising a dosage of about 10 mg of opioid analgesic to about 80 mg of opioid analgesic, wherein subjects administered a single dosage exhibit a mean plasma opioid analgesic $AUC_{0\to\infty}$ of about 100 h·mg/L to about 1600 h·mg/L, including each integer within the specified range. In one aspect, the composition is provided in a dosage form containing a total amount of about 10 mg of an opioid analgesic, wherein subjects administered a single dosage exhibit a mean plasma opioid analgesic $AUC_{0\to\infty}$ of about 150 h·mg/L. In another aspect, the composition is provided in a dosage form containing a total amount of about 20 mg of opioid analgesic, wherein subjects administered a single dosage exhibit a mean plasma opioid analgesic $AUC_{0\to\infty}$ of about 400 h·mg/L. In another aspect, the composition is provided in a dosage form containing a total amount of about 40 mg of opioid analgesic, wherein subjects administered a single dosage exhibit a mean plasma opioid analgesic $AUC_{0\to\infty}$ of about 850 h·mg/L. In another aspect, the composition is provided in a dosage form containing a total amount of about 80 mg of opioid analgesic, wherein subjects administered a single dosage exhibit a mean plasma opioid analgesic $AUC_{0\to\infty}$ of about 1600 h·mg/L.

Another embodiment described herein is a method for treating an individual having pain, with a pharmaceutical composition described herein comprising an abuse-deterrent matrix described herein comprising a dosage of about 10 mg of opioid analgesic to about 80 mg of opioid analgesic, wherein subjects administered a single dosage exhibits a $T_{max}$ of about 3 hrs to about 8 hrs, including each integer within the specified range. In one aspect, the composition is provided in a dosage form containing a total amount of about 10 mg to about 80 mg of opioid analgesic, wherein subjects administered a single dosage exhibit a $T_{max}$ of about 3 hrs, about 4 hrs, about 5 hrs, about 6 hrs, about 7 hrs, or about 8 hrs.

Another embodiment described herein is a method for treating, retarding the progression of, prophylaxis of, delaying the onset of, ameliorating, or reducing the symptoms of pain comprising the administration of a therapeutically effective amount of one or more abuse-deterrent pharmaceutical compositions described herein to a subject with pain, wherein the administration is sufficient to achieve a reduction pain relative to baseline in the subject without substantially inducing one or more side effects including, but not limited to, headache, vertigo, somnolence, nausea, constipation, vomiting, xerostomia, fatigue, pruritus, eructation, heartburn, abdominal discomfort, or loss of appetite.

Another embodiment described herein is a method for treating, retarding the progression of, prophylaxis of, delaying the onset of, ameliorating, or reducing the symptoms of pain comprising the administration of a therapeutically effective amount of one or more abuse-deterrent pharmaceutical compositions described herein to a subject with pain, wherein the administration is sufficient to achieve a reduction pain relative to baseline in the subject without substantially inducing one or more side effects including, but not limited to, opioid use, such as, for example, opioid induced bowel dysfunction, opioid induced constipation, gastrointestinal dysfunction (e.g., inhibition of intestinal motility, constipation, GI sphincter constriction), nausea, emesis (vomiting), biliary spasm, colic, dysphoria, pruritus, urinary retention, depression of respiration, papillary constriction, cardiovascular effects, chest wall rigidity and cough suppression, depression of stress response, and immune suppression associated with use of narcotic analgesia, etc., or combinations thereof.

In another embodiment, the abuse-deterrent pharmaceutical composition described herein is contained and dispensed from a tamper evident packaging. The term "tamper evident" or "tamper resistant" refers to a packaging of any kind that readily displays or allows for an individual to observe any physical interference or manipulation of said packaging. The tamper evident packaging provides reasonable evidence to consumers that tampering has occurred. The tamper evident packaging additionally contains appropriate labeling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, warnings, or other appropriate information.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

In one embodiment described herein, the percent dissolution of oxycodone from the abuse deterrent controlled release matrix compositions of Table 4, generated by the methods described herein and encapsulated in a hard shell capsule as described herein were tested. The percent dissolution of oxycodone was determined by measuring the amount of oxycodone released from the test and reference abuse deterrent compositions in fasted state simulated gastric fluid (FaSSGF) at pH 1.2 for twelve hours according to USP specifications using Apparatus III at 30 dpm. The dissolution and release profiles for pharmaceutical compositions comprising the test abuse deterrent matrix compositions described in Table 4 are shown in Table 5 and FIG. 1.

TABLE 4

Abuse-Deterrent Compositions

| Component | Formulation 1 Mass (mg) | Formulation 1 Mass Percent (%) | Formulation F2 Mass (mg) | Formulation F2 Mass Percent (%) | Formulation F3 Mass (mg) | Formulation F3 Mass Percent (%) | Formulation F4 Mass (mg) | Formulation F4 Mass Percent (%) |
|---|---|---|---|---|---|---|---|---|
| Maisine ™ 35-1 | 199.59 | 57.03 | 199.59 | 57.03 | — | — | 222.0 | 63.4 |
| Polyethylene oxide (PEO 205) | 105.0 | 29.30 | — | — | — | — | — | — |
| Polyethylene oxide (PEO 301) | — | — | 105.0 | 30 | — | — | 115.9 | 33.1 |
| BHA | 1.1 | 0.31 | 1.1 | 0.31 | — | — | 1.1 | 0.31 |
| BHT | 0.44 | 0.11 | 0.44 | 0.11 | — | — | 0.40 | 0.11 |
| IRP69F Beads | 33.7 | 9.7 | 33.7 | 9.7 | 33.9 | 77.2 | — | — |
| Bound Oxycodone | 10 | 2.9 | 10 | 2.9 | 10 | 22.8 | — | — |
| Free Oxycodone | 0 | — | 0 | — | — | — | 10.6 | 3.0 |
| TOTAL | 350 | 100% | 350 | 100% | 350 | 100% | 350 | 100% |
| Ratio of PEO:Maisine ™ 35-1 | 1:1.9 | | 1:1.9 | | — | | 1:1.9 | |
| Ratio of API:PEO | 1:10.5 | | 1:10.5 | | — | | 1:10.9 | |

TABLE 5

Dissolution Profiles for Abuse-Deterrent Compositions

Percent Dissolved/Released (%)

| Time (hr) | Formulation 1 | Formulation 2 | Formulation 3 | Formulation 4 |
|---|---|---|---|---|
| 0 | 0 | 0 | 0 | 0 |
| 1 | 5 | 2 | 58 | 41 |
| 2 | 23 | 5 | 71 | 59 |
| 4 | 60 | 16 | 88 | 81 |
| 8 | 87 | 42 | 98 | 96 |
| 12 | 103 | 67 | 103 | 97 |

As shown in FIG. 1, test pharmaceutical compositions comprising the abuse deterrent matrix according to Formulation 1 and Formulation 2 of Table 4 demonstrated lower dissolution percent of oxycodone compared to abuse deterrent pharmaceutical compositions of Formulation 3 and Formulation 4 of Table 4.

A difference in dissolution and release profile of oxycodone from abuse-deterrent pharmaceutical compositions was observed between pharmaceutical compositions Formulation 1 and Formulation 2, and the composition of Formulation 3 in Table 4 that was not annealed. As shown in FIG. 1, the annealed test pharmaceutical compositions comprising the abuse deterrent matrix according to Formulation 1 and Formulation 2 of Table 4 exhibit lower dissolution percent of oxycodone under aqueous boiling conditions compared to the oxycodone abuse deterrent composition of Formulation 3, which was not annealed. The presence of an ion exchanger in the abuse-deterrent pharmaceutical composition impacted the dissolution of oxycodone from the pharmaceutical composition as shown in FIG. 1. The pharmaceutical composition of Formulation 4 in Table 4 that was annealed but lacking an ion exchanger exhibited a higher dissolution percent as compared to the compositions Formulation 1 and Formulation 2, both of which were annealed and included an ion exchanger in its composition. Without being bound by any theory, this result suggests that the annealing procedure listed in Example 2 may be one contributor to the abuse deterrent properties of the compositions described herein.

FIG. 1 further shows the effect of release modifiers PEO 301 and PEO 205 on the dissolution and release profiles of oxycodone percent release in abuse-deterrent pharmaceutical compositions of Formulation 1 and Formulation 2. As shown in FIG. 1 and Table 5, the oxycodone dissolution was lower in the test pharmaceutical composition comprising the abuse deterrent matrix according to Formulation 2 in Table 4, comprising PEO 301 as compared to Formulation 1 in Table 4, comprising PEO 205. About twice as much of Oxycodone was dissolved (87% vs. 42%) in a test pharmaceutical composition comprising the abuse deterrent matrix according to Formulation 1 (PEO 205) than in a test pharmaceutical composition comprising the abuse deterrent matrix according to Formulation 2 (PEO 301), as shown in FIG. 1 and Table 5.

Example 2

In one embodiment described herein, the percent dissolution of oxycodone from the abuse deterrent controlled release matrix compositions in Table 5 that were encapsulated in a hard shell capsule as described herein was determined. The percent dissolution of oxycodone was determined by measuring the amount of oxycodone released from the test and reference abuse deterrent compositions in fasted state simulated gastric fluid (FaSSGF) at pH 1.2 for twelve hours according to USP specifications using Apparatus III at 30 dpm. The dissolution and release profiles for pharmaceutical compositions comprising the test abuse deterrent matrix compositions described in Table 6 are shown in Table 7 and FIG. 2.

TABLE 6

Abuse-Deterrent Compositions

| Component | Formulation 5 Mass (mg) | Formulation 5 Mass Percent (%) | Formulation 6 Mass (mg) | Formulation 6 Mass Percent (%) | Formulation 7 Mass (mg) | Formulation 7 Mass Percent (%) |
|---|---|---|---|---|---|---|
| Maisine ™ 35-1 | 209.8 | 59.9 | 239.7 | 68.5 | 222 | 63.4 |
| Polyethylene oxide (PEO 205) | 105.0 | 30.0 | 70.0 | 20.0 | 115.9 | 33.1 |

TABLE 6-continued

Abuse-Deterrent Compositions

| | Formulation 5 | | Formulation 6 | | Formulation 7 | |
|---|---|---|---|---|---|---|
| Component | Mass (mg) | Mass Percent (%) | Mass (mg) | Mass Percent (%) | Mass (mg) | Mass Percent (%) |
| BHA | 1.1 | 0.31 | 1.1 | 0.3 | 1.1 | 0.3 |
| BHT | 0.4 | 0.13 | 0.44 | 0.13 | 0.4 | 0.1 |
| IRP69F Beads | 23.7 | 6.8 | 28.8 | 8.2 | 0 | 0 |
| Oxycodone (bound to ion exchanger) | 7.0 | 2.0 | 8.5 | 2.4 | 0 | 0 |
| Oxycodone (free) | 3.0 | 0.9 | 1.5 | 0.4 | 10.6 | 3.0 |
| TOTAL | 350 | 100 | 350 | 100 | 350 | 100 |

TABLE 7

Dissolution Profiles for Abuse-Deterrent Compositions

| | Percent Dissolved/Released (%) | | |
|---|---|---|---|
| Time (Hour) | Formulation 5 | Formulation 6 | Formulation 7 |
| 0 | 0 | 0 | 0 |
| 1 | 22 | 22 | 41 |
| 2 | 44 | 45 | 59 |
| 4 | 80 | 77 | 81 |
| 8 | 101 | 102 | 96 |
| 12 | 108 | 109 | 97 |

As shown in FIG. 2, test pharmaceutical compositions comprising the abuse deterrent matrix according to Formulation 5 and Formulation 6 in Table 6 demonstrated lower dissolution percent of oxycodone compared to abuse deterrent pharmaceutical composition of Formulation 7 in Table 6 which did not include an ion exchanger.

The inclusion of an ion exchanger in the abuse-deterrent pharmaceutical composition impacted the dissolution of oxycodone from the pharmaceutical composition as shown in FIG. 2. The pharmaceutical composition in Formulation 7 in Table 6 that was annealed but lacking an ion exchanger exhibited a higher dissolution percent during the first two hours of testing, as compared to the compositions Formulation 5 and Formulation 6, both of which were annealed and included an ion exchanger in the composition. About twice as much of oxycodone was dissolved in one hour (41% vs. 22%) in a test pharmaceutical composition comprising the abuse deterrent matrix according to Formulation 7 than in test pharmaceutical composition comprising the abuse deterrent matrix according to Formulation 5 and Formulation 6, as shown in FIG. 2 and Table 7. This result suggests that the binding of oxycodone to the ion exchanger listed in Table 6 may be one contributor to the abuse deterrent properties of the compositions described herein.

FIG. 2 further shows that at the level of binding of the oxycodone to the ion exchanger had no effect on dissolution of oxycodone. As shown in FIG. 2 and Table 7, the oxycodone dissolution was comparable for compositions Formulation 5 and Formulation 6 of Table 6, where 70% and 85% of the oxycodone was bound to the ion exchanger, respectively.

Example 3

In another embodiment described herein, the abuse deterrent properties of a pharmaceutical composition comprising the different abuse deterrent matrix formulations (Formulations 5-7) in Table 6 were tested. These compositions were manipulated by subjecting them to a variety of common physical manipulations, including crushing, grating, grinding and cutting and compared to a similarly manipulated commercially available reference abuse deterrent formulations. The test formulations were highly resistant to crushing with a hammer due to the matrix having rubbery, semi-solid, slippery characteristics. By comparison, a reference abuse deterrent formulation was easily crushed into powder like smaller pieces by a hammer or a mortar and pestle. The smaller pieces of the reference formulation were then easily converted to a powder using a mortar and pestle, which likely could be snorted. In contrast, the test formulations could be cut into smaller pieces with a cheese grater, coffee grinder, or other sharp cutting tools, but these smaller pieces would not form a powder suitable for insufflation.

TABLE 8

Dissolution Profiles for Manipulated Abuse-deterrent Compositions

| | Percent Dissolved (%) | | |
|---|---|---|---|
| Time (min) | Formulation 5 | Formulation 6 | Formulation 7 |
| 0 | 0 | 0 | 0 |
| 5 | 35 | 19 | 83 |
| 15 | 49 | 29 | 89 |
| 30 | 57 | 39 | 90 |
| 45 | 63 | 47 | 91 |
| 60 | 67 | 52 | 92 |
| 90 | 73 | 59 | 94 |
| 120 | 78 | 65 | 93 |

In an embodiment, the percent dissolution of oxycodone from manipulated abuse deterrent controlled release matrix compositions Formulation 5, Formulation 6 and Formulation 7 in Table 6 that were encapsulated in a hard shell capsule as described herein was determined. The samples are subjected to grinding in a coffee grinder for fifteen seconds, followed by a ten second pause, and then ground for an additional fifteen seconds. An amount of each formulation corresponding to the approximate weight of each of the intact compositions was used in the study. An intact prototype with the composition of Formulation 7 in Table 6 was used as a reference for comparison of dissolution rate, the composition of this reference test sample did not include an ion exchanger. The percent dissolution of oxycodone was determined by measuring the amount of oxycodone released from the test and reference abuse deterrent compositions in fasted state simulated gastric fluid (FaSSGF) at pH 1.2 for two hours and in fasted state simulated intestinal fluid (FaSSIF) at pH 6.8 for twelve hours according to USP specifications using Apparatus III at 30 dpm. The dissolution and release profiles for pharmaceutical compositions comprising the test abuse deterrent matrix compositions described in Table 6 are shown in Table 8 and FIG. 3.

As shown in FIG. 3, manipulated test pharmaceutical compositions comprising the abuse deterrent matrix according to Formulation 5 and Formulation 6 of Table 6 demonstrated lower dissolution percent of oxycodone compared to the reference abuse deterrent pharmaceutical composition Formulation 7 in Table 6. The inclusion of an ion exchanger in the abuse-deterrent pharmaceutical composition impacted the dissolution of oxycodone from the pharmaceutical composition as shown in FIG. 3. The pharmaceutical composition in Formulation 7 in Table 6 that was annealed but lacking an ion exchanger exhibited a higher dissolution percent during the first five minutes of testing, as compared to the compositions Formulation 5 and Formulation 6. About two to four times as much of Oxycodone was dissolved in the abuse deterrent pharmaceutical composition Formulation 7 in Table 6 than in test pharmaceutical compositions in Formulation 5 and Formulation 6 as shown in FIG. 3 and in Table 8, 83% vs. 35% and 19% dissolution was observed for abuse-deterrent compositions Formulation 7 vs. Formulation 5 and Formulation 6 in Table 6, respectively. These results suggest that the binding of oxycodone to the ion exchanger listed in Table 6 is a contributor to the abuse deterrent properties of the compositions described herein.

FIG. 3 further shows that the amount of free oxycodone influenced the dissolution profile of oxycodone. As shown in FIG. 3 and Table 8, oxycodone dissolution was lower for the composition of Formulation 6 of Table 6, where the amount of free oxycodone was 15%, as opposed to the composition of Formulation 5 where 30% oxycodone was free in the composition of Formulation 6 in Table 6.

Example 4

In one embodiment described herein, exemplary abuse-deterrent controlled release matrix have the compositions of Tables 9-10, including all possible iterations of the specified ranges that provide 100% for the total weight percentage, including or excluding optional excipients. In one embodiment described herein, an exemplary abuse-deterrent controlled release matrix has the composition in Tables 9-10, including all possible iterations of the specified ranges that provide for exemplary abuse-deterrent controlled release matrix compositions comprising PEO 205 or alternatively PEO 301, and 10 mg of drug, wherein, an amount of the drug bound to ion exchanger ranges from about 2 mg to about 8 mg (from about 0.5% to about 2.5%). Abuse-deterrent dosage forms are prepared using the compositions in Tables 9-10, and are encapsulated in a soft capsule with a polyvinyl alcohol coating as a moisture barrier. The dosage forms are annealed in a coating pan after coating at 60-70° C. for 30 to 90 min and then slowly cooled to room temperature (dropping about 5° C. every 5 to 15 min).

TABLE 9

Abuse-Deterrent Compositions

| Component | Formulation 8 Mass (mg) | Formulation 8 Mass % | Formulation 9 Mass (mg) | Formulation 9 Mass % | Formulation 10 Mass (mg) | Formulation 10 Mass % |
|---|---|---|---|---|---|---|
| Maisine 35-1 | 209.8 | 59.9 | 209.8 | 59.9 | 209.8 | 59.9 |
| PEO 205 or PEO 301 | 105.0 | 30.0 | 105.0 | 30.0 | 105.0 | 30.0 |
| BHA | 1.1 | 0.3 | 1.1 | 0.3 | 1.1 | 0.3 |
| BHT | 0.4 | 0.1 | 0.4 | 0.1 | 0.4 | 0.1 |
| IEX (IRP69F Resin) | 23.7 | 6.8 | 23.7 | 6.8 | 23.7 | 6.8 |
| Bound Oxycodone HCl | 8.0 | 2.3 | 9.0 | 2.6 | 6.0 | 1.7 |
| Free Oxycodone HCl | 2.0 | 0.6 | 1.0 | 0.3 | 4.0 | 1.1 |
| TOTAL | 350.0 | 100.0% | 350.0 | 100.0% | 350.0 | 100.0% |
| IEX-Oxy Complex | 31.7 | 9.1% | 32.7 | 9.3% | 29.7 | 8.5% |
| Total Oxycodone HCl | 10.0 | 2.9% | 10.0 | 2.9% | 10.0 | 2.9% |
| Ratio of IEX:Oxy (total) | 2.4 | 2.4 | 2.4 | 2.4 | 2.4 | 2.4 |
| Ratio of IEX:Oxy (bound) | 3.0 | 3.0 | 2.6 | 2.6 | 4.0 | 4.0 |
| Ratio of IEX:Oxy (Free) | 11.9 | 11.9 | 23.7 | 23.7 | 5.9 | 5.9 |
| Ratio of Components:Oxy | 34.0 | 34.0 | 34.0 | 34.0 | 34.0 | 34.0 |

TABLE 10

Abuse-Deterrent Compositions

| Component | Formulation 11 Mass (mg) | Formulation 11 Mass % | Formulation 12 Mass (mg) | Formulation 12 Mass % | Formulation 13 Mass (mg) | Formulation 13 Mass % |
|---|---|---|---|---|---|---|
| Maisine 35-1 | 209.8 | 59.9 | 209.8 | 59.9 | 209.8 | 59.9 |
| PEO 205 or PEO 301 | 105.0 | 30.0 | 105.0 | 30.0 | 105.0 | 30.0 |
| BHA | 1.1 | 0.3 | 1.1 | 0.3 | 1.1 | 0.3 |
| BHT | 0.4 | 0.1 | 0.4 | 0.1 | 0.4 | 0.1 |
| IEX (IRP69F Resin) | 23.7 | 6.8 | 23.7 | 6.8 | 23.7 | 6.8 |
| Bound Oxycodone HCl | 5.0 | 1.4 | 4.0 | 1.1 | 2.0 | 0.6 |
| Free Oxycodone HCl | 5.0 | 1.4 | 6.0 | 1.7 | 8.0 | 2.3 |
| TOTAL | 350.0 | 100.0% | 350.0 | 100.0% | 350.0 | 100.0% |
| Resin-Oxy Complex | 28.7 | 8.2% | 27.7 | 7.9 | 25.7 | 7.3% |
| Total Oxycodone HCl | 10.0 | 2.9% | 10.0 | 2.9 | 10.0 | 2.9% |
| Ratio of IEX:Oxy (total) | 2.4 | 2.4 | 2.4 | 2.4 | 2.4 | 2.4 |
| Ratio of IEX:Oxy (bound) | 4.7 | 4.7 | 5.9 | 5.9 | 11.9 | 11.9 |
| Ratio of IEX:Oxy (Free) | 4.7 | 4.7 | 4.0 | 4.0 | 3.0 | 3.0 |
| Ratio of Components:Oxy | 34.0 | 34.0 | 34.0 | 34.0 | 34.0 | 34.0 |

Example 5

In one embodiment described herein, an exemplary abuse-deterrent controlled release matrix has the composition in Tables 11-12, including all possible iterations of the specified ranges that provide for exemplary abuse-deterrent controlled release matrix compositions comprising 10 mg of drug, wherein, an amount of the drug bound to the ion exchanger ranges from about 2 mg to about 9.5 mg. Abuse-deterrent dosage forms are prepared using the compositions in Tables 11-12, and can be encapsulated in a soft capsule shell with a polyvinyl alcohol coating as a moisture barrier. The dosage forms can be annealed in a coating pan after coating at 60-70° C. for 30 to 90 min and then slowly cooled to room temperature (dropping about 5° C. every 5 to 15 min).

TABLE 11

Abuse-Deterrent Compositions

| Component | Formulation 14 Mass (mg) | Formulation 14 Mass % | Formulation 15 Mass (mg) | Formulation 15 Mass % | Formulation 16 Mass (mg) | Formulation 16 Mass % |
|---|---|---|---|---|---|---|
| Maisine 35-1 | 239.7 | 68.5 | 239.7 | 68.5 | 239.7 | 68.5 |
| PEO 205 | 70.0 | 20.0 | 70.0 | 20.0 | 70.0 | 20.0 |
| BHA | 1.1 | 0.3 | 1.1 | 0.3 | 1.1 | 0.3 |
| BHT | 0.4 | 0.1 | 0.4 | 0.1 | 0.4 | 0.1 |
| IRP69F Resin | 28.8 | 8.2 | 28.8 | 8.2 | 28.8 | 8.2 |
| Bound Oxycodone | 9.5 | 2.7 | 8.0 | 2.3 | 7.0 | 2.0 |
| Free Oxycodone HCl | 0.5 | 0.1 | 2.0 | 0.6 | 3.0 | 0.9 |
| TOTAL | 350.0 | 100.0% | 350.0 | 100.0% | 350.0 | 100.0% |
| Resin-Oxy Complex | 38.3 | 10.9% | 36.8 | 10.5% | 35.8 | 10.2% |
| Total Oxycodone | 10.0 | 2.9% | 10.0 | 2.9% | 10.0 | 2.9% |
| Ratio of IEX:Oxy (total) | 2.9 | 2.9 | 2.9 | 2.9 | 2.9 | 2.9 |
| Ratio of IEX:Oxy (bound) | 3.0 | 3.0 | 3.6 | 3.6 | 4.1 | 4.1 |
| Ratio of IEX:Oxy (Free) | 57.6 | 57.6 | 14.4 | 14.4 | 9.6 | 9.6 |
| Ratio of Components:Oxy | 34.0 | 34.0 | 34.0 | 34.0 | 34.0 | 34.0 |

TABLE 12

Abuse-Deterrent Compositions

| Component | Formulation 17 Mass (mg) | Formulation 17 Mass % | Formulation 18 Mass (mg) | Formulation 18 Mass % | Formulation 19 Mass (mg) | Formulation 19 Mass % |
|---|---|---|---|---|---|---|
| Maisine 35-1 | 239.7 | 68.5 | 239.7 | 68.5 | 239.7 | 68.5 |
| PEO 205 | 70.0 | 20.0 | 70.0 | 20.0 | 70.0 | 20.0 |
| BHA | 1.1 | 0.3 | 1.1 | 0.3 | 1.1 | 0.3 |
| BHT | 0.4 | 0.1 | 0.4 | 0.1 | 0.4 | 0.1 |
| IRP69F Resin | 28.8 | 8.2 | 28.8 | 8.2 | 28.8 | 8.2 |
| Bound Oxycodone | 5.0 | 1.4 | 3.0 | 0.9 | 2.0 | 0.6 |
| Free Oxycodone HCl | 5.0 | 1.4 | 7.0 | 2.0 | 8.0 | 2.3 |
| TOTAL | 350.0 | 100.0% | 350.0 | 100.0% | 350.0 | 100.0% |
| Resin-Oxy Complex | 33.8 | 9.7% | 31.8 | 9.1% | 30.8 | 8.8% |
| Total Oxycodone | 10.0 | 2.9% | 10.0 | 2.9% | 10.0 | 2.9% |
| Ratio of IEX:Oxy (total) | 2.9 | 2.9 | 2.9 | 2.9 | 2.9 | 2.9 |
| Ratio of IEX:Oxy (bound) | 5.8 | 5.8 | 9.6 | 9.6 | 14.4 | 14.4 |
| Ratio of IEX:Oxy (Free) | 5.8 | 5.8 | 4.1 | 4.1 | 3.6 | 3.6 |
| Ratio of Components:Oxy | 34.0 | 34.0 | 34.0 | 34.0 | 34.0 | 34.0 |

Example 6

In one embodiment described herein, exemplary abuse-deterrent controlled release matrix have the compositions of Tables 13-16, including all possible iterations of the specified ranges that provide 100% for the total weight percentage, including or excluding optional excipients. In one embodiment described herein, an exemplary abuse-deterrent controlled release matrix has the composition in Tables 13-16, including all possible iterations of the specified ranges that provide for exemplary abuse-deterrent controlled release matrix compositions comprising 10 mg of drug, wherein the ratios of bound and free drug are held constant but the amount of PEO ranges from about 11% to about 35%. Without being bound to the exemplary formulations as shown in Tables 13-16, the composition may comprise a PEO other than 205, such as PEO 301, for example. Abuse-deterrent dosage forms are prepared using the compositions in Tables 13-16, and can be encapsulated in a soft capsule shell with a polyvinyl alcohol coating as a moisture barrier. The dosage forms can be annealed in a coating pan after coating at 60-70° C. for 30 to 90 min and then slowly cooled to room temperature (dropping about 5° C. every 5 to 15 min).

TABLE 13

Abuse-Deterrent Compositions

| Component | Formulation 20 Mass (mg) | Formulation 20 Mass | Formulation 21 Mass (mg) | Formulation 21 Mass % | Formulation 22 Mass (mg) | Formulation 22 Mass % |
|---|---|---|---|---|---|---|
| Maisine 35-1 | 229.8 | 65.6 | 224.8 | 64.2 | 214.8 | 61.4 |
| PEO 205 | 85.0 | 24.3 | 90.0 | 25.7 | 100.0 | 28.6 |
| BHA | 1.1 | 0.3 | 1.1 | 0.3 | 1.1 | 0.3 |
| BHT | 0.4 | 0.1 | 0.4 | 0.1 | 0.4 | 0.1 |
| IRP69F Resin | 23.7 | 6.8 | 23.7 | 6.8 | 23.7 | 6.8 |
| Bound Oxycodone | 7.0 | 2.0 | 7.0 | 2.0 | 7.0 | 2.0 |
| Free Oxycodone HCl | 3.0 | 0.9 | 3.0 | 0.9 | 3.0 | 0.9 |
| TOTAL | 350.0 | 100.0% | 350.0 | 100.0% | 350.0 | 100.0% |
| Resin-Oxy Complex | 30.7 | 8.8% | 30.7 | 8.8% | 30.7 | 8.8% |
| Total Oxycodone | 10.0 | 2.9% | 10.0 | 2.9% | 10.0 | 2.9% |
| Ratio of IEX:Oxy (total) | 2.4 | 2.4 | 2.4 | 2.4 | 2.4 | 2.4 |
| Ratio of IEX:Oxy (bound) | 3.4 | 3.4 | 3.4 | 3.4 | 3.4 | 3.4 |
| Ratio of IEX:Oxy (Free) | 7.9 | 7.9 | 7.9 | 7.9 | 7.9 | 7.9 |
| Ratio of Components:Oxy | 34.0 | 34.0 | 34.0 | 34.0 | 34.0 | 34.0 |

TABLE 14

Abuse-Deterrent Compositions

| Component | Formulation 23 Mass (mg) | Formulation 23 Mass % | Formulation 24 Mass (mg) | Formulation 24 Mass % |
|---|---|---|---|---|
| Maisine 35-1 | 204.8 | 58.5 | 194.8 | 55.6 |
| PEO 205 | 110.0 | 31.4 | 120.0 | 34.3 |
| BHA | 1.1 | 0.3 | 1.1 | 0.3 |
| BHT | 0.4 | 0.1 | 0.4 | 0.1 |
| IRP69F Resin | 23.7 | 6.8 | 23.7 | 6.8 |
| Bound Oxycodone | 7.0 | 2.0 | 7.0 | 2.0 |
| Free Oxycodone HCl | 3.0 | 0.9 | 3.0 | 0.9 |
| TOTAL | 350.0 | 100.0% | 350.0 | 100.0% |
| Resin-Oxy Complex | 30.7 | 8.8% | 30.7 | 8.8% |
| Total Oxycodone | 10.0 | 2.9% | 10.0 | 2.9% |
| Ratio of IEX:Oxy (total) | 2.4 | 2.4 | 2.4 | 2.4 |
| Ratio of IEX:Oxy (bound) | 3.4 | 3.4 | 3.4 | 3.4 |
| Ratio of IEX:Oxy (Free) | 7.9 | 7.9 | 7.9 | 7.9 |
| Ratio of Components:Oxy | 34.0 | 34.0 | 34.0 | 34.0 |

TABLE 15

Abuse-Deterrent Compositions

| Component | Formulation 25 Mass (mg) | Formulation 25 Mass % | Formulation 26 Mass (mg) | Formulation 26 Mass % | Formulation 27 Mass (mg) | Formulation 27 Mass % |
|---|---|---|---|---|---|---|
| Maisine 35-1 | 249.7 | 71.3 | 259.7 | 74.2 | 269.7 | 77.0 |
| PEO 205 | 60.0 | 17.1 | 50.0 | 14.3 | 40.0 | 11.4 |
| BHA | 1.1 | 0.3 | 1.1 | 0.3 | 1.1 | 0.3 |
| BHT | 0.4 | 0.1 | 0.4 | 0.1 | 0.4 | 0.1 |
| IRP69F Resin | 28.8 | 8.2 | 28.8 | 8.2 | 28.8 | 8.2 |

TABLE 15-continued

Abuse-Deterrent Compositions

| Component | Formulation 25 Mass (mg) | Formulation 25 Mass % | Formulation 26 Mass (mg) | Formulation 26 Mass % | Formulation 27 Mass (mg) | Formulation 27 Mass % |
|---|---|---|---|---|---|---|
| Bound Oxycodone | 8.5 | 2.4 | 8.5 | 2.4 | 8.5 | 2.4 |
| Free Oxycodone HCl | 1.5 | 0.4 | 1.5 | 0.4 | 1.5 | 0.4 |
| TOTAL | 350.0 | 100.0% | 350.0 | 100.0% | 350.0 | 100.0% |
| Resin-Oxy Complex | 37.3 | 10.7% | 37.3 | 10.7% | 37.3 | 10.7% |
| Total Oxycodone | 10.0 | 2.9% | 10.0 | 2.9% | 10.0 | 2.9% |
| Ratio of IEX:Oxy (total) | 2.9 | 2.9 | 2.9 | 2.9 | 2.9 | 2.9 |
| Ratio of IEX:Oxy (bound) | 3.4 | 3.4 | 3.4 | 3.4 | 3.4 | 3.4 |
| Ratio of IEX:Oxy (Free) | 19.2 | 19.2 | 19.2 | 19.2 | 19.2 | 19.2 |
| Ratio of Components:Oxy | 34.0 | 34.0 | 34.0 | 34.0 | 34.0 | 34.0 |

TABLE 16

Abuse-Deterrent Compositions

| Component | Formulation 28 Mass (mg) | Formulation 28 Mass % | Formulation 29 Mass (mg) | Formulation 29 Mass % |
|---|---|---|---|---|
| Maisine 35-1 | 239.7 | 68.5 | 229.7 | 65.6 |
| PEO 205 | 70.0 | 20.0 | 80.0 | 22.9 |
| BHA | 1.1 | 0.3 | 1.1 | 0.3 |
| BHT | 0.4 | 0.1 | 0.4 | 0.1 |
| IRP69F Resin | 28.8 | 8.2 | 28.8 | 8.2 |
| Bound Oxycodone | 8.5 | 2.4 | 8.5 | 2.4 |
| Free Oxycodone HCl | 1.5 | 0.4 | 1.5 | 0.4 |
| TOTAL | 350.0 | 100.0% | 350.0 | 100.0% |
| Resin-Oxy Complex | 37.3 | 10.7% | 37.3 | 10.7% |
| Total Oxycodone | 10.0 | 2.9% | 10.0 | 2.9% |
| Ratio of IEX:Oxy (total) | 2.9 | 2.9 | 2.9 | 2.9 |
| Ratio of IEX:Oxy (bound) | 3.4 | 3.4 | 3.4 | 3.4 |
| Ratio of IEX:Oxy (Free) | 19.2 | 19.2 | 19.2 | 19.2 |
| Ratio of Components:Oxy | 34.0 | 34.0 | 34.0 | 34.0 |

Example 8

In one embodiment described herein, exemplary abuse-deterrent controlled release matrix have the compositions of Tables 17-19, including all possible iterations of the specified ranges that provide 100% for the total weight percentage, including or excluding optional excipients. In one embodiment described herein, an exemplary abuse-deterrent controlled release matrix has the composition in Tables 17-19, including all possible iterations of the specified ranges that provide for exemplary abuse-deterrent controlled release matrix compositions comprising 10 mg of drug, wherein, the ratio of free and bound drug is held constant but the PEO used in the composition is varied, as shown in Tables 17-19, the compositions comprise a combination of PEO 205 and PEO 301. Abuse-deterrent dosage forms are prepared using the compositions in Tables 17-19, and can be encapsulated in a soft capsule shell with a polyvinyl alcohol coating as a moisture barrier. The dosage forms can be annealed in a coating pan after coating at 60-70° C. for 30 to 90 min and then slowly cooled to room temperature (dropping about 5° C. every 5 to 15 min).

TABLE 17

Abuse-Deterrent Compositions

| Component | Formulation 30 Mass (mg) | Formulation 30 Mass % | Formulation 31 Mass (mg) | Formulation 31 Mass % | Formulation 32 Mass (mg) | Formulation 32 Mass % |
|---|---|---|---|---|---|---|
| Maisine 35-1 | 209.8 | 59.9 | 209.8 | 59.9 | 209.8 | 59.9 |
| PEO 205 | 95.0 | 27.1 | 85.0 | 24.3 | 75.0 | 21.4 |
| PEO 301 | 10.0 | 2.9 | 20.0 | 5.7 | 30.0 | 8.6 |
| BHA | 1.1 | 0.3 | 1.1 | 0.3 | 1.1 | 0.3 |
| BHT | 0.4 | 0.1 | 0.4 | 0.1 | 0.4 | 0.1 |
| IRP69F Resin | 23.7 | 6.8 | 23.7 | 6.8 | 23.7 | 6.8 |
| Bound Oxycodone | 7.0 | 2.0 | 7.0 | 2.0 | 7.0 | 2.0 |
| Free Oxycodone HCl | 3.0 | 0.9 | 3.0 | 0.9 | 3.0 | 0.9 |
| TOTAL | 350.0 | 100.0% | 350.0 | 100.0% | 350.0 | 100.0% |
| Resin-Oxy Complex | 30.7 | 8.8% | 30.7 | 8.8% | 30.7 | 8.8% |
| Total Oxycodone | 10.0 | 2.9% | 10.0 | 2.9% | 10.0 | 2.9% |
| Ratio of IEX:Oxy (total) | 2.4 | 2.4 | 2.4 | 2.4 | 2.4 | 2.4 |
| Ratio of IEX:Oxy (bound) | 3.0 | 3.0 | 3.0 | 3.0 | 3.0 | 3.0 |
| Ratio of IEX:Oxy (Free) | 11.9 | 11.9 | 11.9 | 11.9 | 11.9 | 11.9 |
| Ratio of Components:Oxy | 34.0 | 34.0 | 34.0 | 34.0 | 34.0 | 34.0 |

TABLE 18

Abuse-Deterrent Compositions

| Component | Formulation 32 Mass (mg) | Formulation 32 Mass % | Formulation 34 Mass (mg) | Formulation 34 Mass % | Formulation 35 Mass (mg) | Formulation 35 Mass % |
|---|---|---|---|---|---|---|
| Maisine 35-1 | 209.8 | 59.9 | 209.8 | 59.9 | 209.8 | 59.9 |
| PEO 205 | 65.0 | 18.6 | 55.0 | 15.7 | 40.0 | 11.4 |
| PEO 301 | 40.0 | 11.4 | 50.0 | 14.3 | 65.0 | 18.6 |
| BHA | 1.1 | 0.3 | 1.1 | 0.3 | 1.1 | 0.3 |
| BHT | 0.4 | 0.1 | 0.4 | 0.1 | 0.4 | 0.1 |
| IRP69F Resin | 23.7 | 6.8 | 23.7 | 6.8 | 23.7 | 6.8 |
| Bound Oxycodone | 7.0 | 2.0 | 7.0 | 2.0 | 7.0 | 2.0 |
| Free Oxycodone HCl | 3.0 | 0.9 | 3.0 | 0.9 | 3.0 | 0.9 |
| TOTAL | 350.0 | 100.0% | 350.0 | 100.0% | 350.0 | 100.0% |
| Resin-Oxy Complex | 30.7 | 8.8% | 30.7 | 8.8% | 30.7 | 8.8% |
| Total Oxycodone | 10.0 | 2.9% | 10.0 | 2.9% | 10.0 | 2.9% |
| Ratio of IEX:Oxy (total) | 2.4 | 2.4 | 2.4 | 2.4 | 2.4 | 2.4 |
| Ratio of IEX:Oxy (bound) | 3.0 | 3.0 | 3.0 | 3.0 | 3.0 | 3.0 |
| Ratio of IEX:Oxy (Free) | 11.9 | 11.9 | 11.9 | 11.9 | 11.9 | 11.9 |
| Ratio of Components:Oxy | 34.0 | 34.0 | 34.0 | 34.0 | 34.0 | 34.0 |

TABLE 19

Abuse-Deterrent Compositions

| Component | Formulation 36 Mass (mg) | Formulation 36 Mass % | Formulation 37 Mass (mg) | Formulation 37 Mass % | Formulation 38 Mass (mg) | Formulation 38 Mass % |
|---|---|---|---|---|---|---|
| Maisine 35-1 | 209.8 | 59.9% | 209.8 | 59.9% | 209.8 | 59.9% |
| PEO 205 | 30.0 | 8.6% | 20.0 | 5.7% | 10.0 | 2.9% |
| PEO 301 | 75.0 | 21.4% | 85.0 | 24.3% | 95.0 | 27.1% |
| BHA | 1.1 | 0.3% | 1.1 | 0.3% | 1.1 | 0.3% |
| BHT | 0.4 | 0.1% | 0.4 | 0.1% | 0.4 | 0.1% |
| IRP69F Resin | 23.7 | 6.8% | 23.7 | 6.8% | 23.7 | 6.8% |

TABLE 19-continued

Abuse-Deterrent Compositions

| Component | Formulation 36 Mass (mg) | Formulation 36 Mass % | Formulation 37 Mass (mg) | Formulation 37 Mass % | Formulation 38 Mass (mg) | Formulation 38 Mass % |
|---|---|---|---|---|---|---|
| Bound Oxycodone | 7.0 | 2.0% | 7.0 | 2.0% | 7.0 | 2.0% |
| Free Oxycodone HCl | 3.0 | 0.9% | 3.0 | 0.9% | 3.0 | 0.9% |
| TOTAL | 350.0 | 100.0% | 350.0 | 100.0% | 350.0 | 100.0% |
| Resin-Oxy Complex | 30.7 | 8.8% | 30.7 | 8.8% | 30.7 | 8.8% |
| Total Oxycodone | 10.0 | 2.9% | 10.0 | 2.9% | 10.0 | 2.9% |
| Ratio of IEX:Oxy (total) | 2.4 | 2.4 | 2.4 | 2.4 | 2.4 | 2.4 |
| Ratio of IEX:Oxy (bound) | 3.0 | 3.0 | 3.0 | 3.0 | 3.0 | 3.0 |
| Ratio of IEX:Oxy (Free) | 11.9 | 11.9 | 11.9 | 11.9 | 11.9 | 11.9 |
| Ratio of Components:Oxy | 34.0 | 34.0 | 34.0 | 34.0 | 34.0 | 34.0 |

What is claimed is:

1. An oral pharmaceutical composition comprising:
   (a) about 50% to about 70% by mass of glyceryl monolinoleate;
   (b) about 2% to 50% by mass ion exchanger;
   (c) about 25% to about 40% by mass of a polyethylene oxide having a molecular weight ($M_v$) of about 1,000,000 to about 7,000,000; and
   (d) about 1% to 20% by mass of one or more active pharmaceutical ingredients (API), wherein 15% or about 30% of the API is in a free form and 70% or about 85% of the API is bound to the ion exchanger.

2. The composition of claim 1, wherein the composition forms an abuse deterrent elastic semi-solid composition after being heated at a temperature of about 50° C. to about 80° C. for a time period of about 10 min to about 180 min and then cooling the composition to room temperature.

3. The composition of claim 1, wherein a greater quantity of API is adsorbed by the ion exchanger when a plurality of dosage forms are simultaneously ingested or successively ingested over about a 4 hour period.

4. The composition of claim 1, wherein the plurality of doses is 2 or greater.

5. The composition of claim 1, wherein the plurality of doses is from 2 to 30.

6. The composition of claim 1, wherein the portion of API bound to the ion exchanger is about 70%.

7. The composition of claim 1, wherein the portion of API bound to the ion exchanger is about 85%.

8. The composition of claim 1, wherein following ingestion of the composition by a subject, the one or more ion exchanger adsorbs a quantity of the one or more API and impedes its release into the subject's systemic circulation.

9. The composition of claim 1, wherein the API comprises oxycodone or a pharmaceutically acceptable salt thereof.

10. The composition of claim 1, further comprising:
    (a) about 0.1% to about 0.4% by mass of BHA; and
    (b) about 0.05% to about 0.1% by mass of BHT.

11. The composition of claim 1, wherein the composition comprises:
    (a) about 50% to about 70% by mass of glyceryl monolinoleate;
    (b) about 2% to 50% by mass ion exchanger;
    (c) about 25% to about 40% by mass of polyethylene oxide having a molecular weight ($M_v$) of about 1,000,000 to about 7,000,000;
    (d) about 0.05% to about 0.4% by mass of BHA;
    (e) about 0.05% to about 0.1% by mass of BHT; and
    (f) about 1% to about 20% of by mass of oxycodone hydrochloride.

12. The composition of claim 1, wherein the composition comprises:
    (a) about 1% to about 30% by mass API; and
    (b) about 20% to 50% by mass ion exchanger.

13. The composition of claim 1, wherein the ion exchanger comprises: polystyrene sulfonate or a salt thereof.

14. The composition of claim 1, wherein the composition comprises:
    (a) about 2% to about 10% by mass API; and
    (b) about 5% to about 50% by mass ion exchanger.

15. The composition of claim 1, wherein the composition is capable of achieving one or more of the following pharmacokinetic parameters:
    (a) a lower $C_{max}$ for the API as compared to an equivalent API dose lacking an ion exchanger;
    (b) a delayed $T_{max}$ for the API as compared to an equivalent API dose lacking an ion exchanger;
    (c) a similar plasma AUC for the API as compared to an equivalent API dose lacking an ion exchanger;
    (d) an extended absorption time for the API as compared to an equivalent API dose lacking an ion exchanger; or
    (e) an extended clearance time for the API as compared to an equivalent API dose lacking an ion exchanger.

16. The composition of claim 1, wherein the composition exhibits an in vitro disintegration or dissolution rate comprises about 50% after about 120 minutes in simulated gastric fluid (pH 1.2) in an USP Apparatus III.

17. The composition of claim 1, wherein the composition is a non-layered semi-solid composition.

18. The composition of claim 1, wherein the API comprises about 5 mg to about 120 mg of oxycodone hydrochloride.

19. The composition of claim 1, wherein the composition comprises an API to ion exchanger mass ratio of about 1:2 to about 1:5.

20. The composition of claim 1, wherein the composition comprises an API to ion exchanger mass ratio of about 1:2 to about 1:3.

* * * * *